US011179097B2

(12) United States Patent
Moskowitz et al.

(10) Patent No.: US 11,179,097 B2
(45) Date of Patent: *Nov. 23, 2021

(54) TACTILE SENSING DEVICE FOR LUMBAR PUNCTURES

(71) Applicant: Texas Medical Center, Houston, TX (US)

(72) Inventors: Nicole C. Moskowitz, Monsey, NY (US); Jessica Traver, Sierra Madre, CA (US); Xavier Garcia-Rojas, The Woodlands, TX (US); Yashar Ganjeh, Chicago, IL (US)

(73) Assignee: TEXAS MEDICAL CENTER, Houston, TX (US)

( * ) Notice: Subject to any disclaimer, the term of this patent is extended or adjusted under 35 U.S.C. 154(b) by 777 days.

This patent is subject to a terminal disclaimer.

(21) Appl. No.: 15/927,664

(22) Filed: Mar. 21, 2018

(65) Prior Publication Data

US 2018/0206781 A1  Jul. 26, 2018

Related U.S. Application Data

(63) Continuation of application No. 15/584,875, filed on May 2, 2017, now Pat. No. 10,004,450.
(Continued)

(51) Int. Cl.
*A61B 5/00* (2006.01)
*A61B 17/34* (2006.01)
(Continued)

(52) U.S. Cl.
CPC .......... *A61B 5/4566* (2013.01); *A61B 5/0053* (2013.01); *A61B 5/4896* (2013.01);
(Continued)

(58) Field of Classification Search
CPC ... A61B 5/4566; A61B 5/0053; A61B 5/4896; A61B 17/3401; A61B 17/3403;
(Continued)

(56) References Cited

U.S. PATENT DOCUMENTS

| 4,919,653 A | 4/1990 | Martinez et al. |
| 5,097,842 A | 3/1992 | Bonn |

(Continued)

FOREIGN PATENT DOCUMENTS

| CN | 101877192 A | 11/2010 |
| CN | 102133096 A | 7/2011 |

(Continued)

OTHER PUBLICATIONS

PCT/US2017/030650 International Search Report and Written Opinion dated Sep. 21, 2017.
(Continued)

*Primary Examiner* — Hien N Nguyen
(74) *Attorney, Agent, or Firm* — Wilson Sonsini Goodrich & Rosati

(57) ABSTRACT

Tactile sensing devices, systems, and methods to image a target tissue location are disclosed. When force is applied to the tactile sensing device, voltage data is detected and visualized on a screen, indicating the target tissue location.

20 Claims, 18 Drawing Sheets

Related U.S. Application Data

(60) Provisional application No. 62/484,354, filed on Apr. 11, 2017, provisional application No. 62/331,279, filed on May 3, 2016.

(51) Int. Cl.
*A61M 5/42* (2006.01)
*A61B 90/00* (2016.01)
*A61B 5/06* (2006.01)
*A61B 17/00* (2006.01)
*A61M 5/46* (2006.01)

(52) U.S. Cl.
CPC ...... *A61B 17/3401* (2013.01); *A61B 17/3403* (2013.01); *A61B 17/3494* (2013.01); *A61M 5/427* (2013.01); *A61B 5/0006* (2013.01); *A61B 5/066* (2013.01); *A61B 5/4504* (2013.01); *A61B 5/4887* (2013.01); *A61B 17/3417* (2013.01); *A61B 17/3468* (2013.01); *A61B 2017/00022* (2013.01); *A61B 2017/00026* (2013.01); *A61B 2017/3405* (2013.01); *A61B 2017/3407* (2013.01); *A61B 2017/3413* (2013.01); *A61B 2090/065* (2016.02); *A61M 5/46* (2013.01); *A61M 2210/1003* (2013.01)

(58) Field of Classification Search
CPC ............... A61B 17/3494; A61B 5/427; A61B 2090/065; A61B 2017/3405; A61B 2017/3407; A61B 5/066; A61B 5/0006; A61B 5/4504; A61B 5/4887; A61B 17/3417; A61B 17/3468; A61B 2017/00022; A61B 2017/00026; A61B 2017/3413; A61M 5/46; A61M 2210/1003
See application file for complete search history.

(56) References Cited

U.S. PATENT DOCUMENTS

| | | |
|---|---|---|
| 5,163,901 A | 11/1992 | Eldor |
| 5,706,815 A | 1/1998 | Sarvazyan et al. |
| 5,785,663 A | 7/1998 | Sarvazyan |
| 5,795,307 A | 8/1998 | Krueger |
| 5,833,633 A | 11/1998 | Sarvazyan |
| 5,833,634 A | 11/1998 | Laird et al. |
| 6,063,031 A | 5/2000 | Cundari et al. |
| 6,142,959 A | 11/2000 | Sarvazyan et al. |
| 6,251,686 B1 | 6/2001 | Studer et al. |
| 6,468,231 B2 | 10/2002 | Sarvazyan et al. |
| 6,500,119 B1 | 12/2002 | West et al. |
| 6,569,108 B2 | 5/2003 | Sarvazyan et al. |
| 6,595,933 B2 | 7/2003 | Sarvazyan et al. |
| 6,620,115 B2 | 9/2003 | Sarvazyan et al. |
| 7,291,109 B1 | 11/2007 | Sarvazyan |
| 7,819,824 B2 | 10/2010 | Sarvazyan et al. |
| 7,922,674 B2 | 4/2011 | Sarvazyan et al. |
| 7,955,278 B1 | 6/2011 | Sarvazyan |
| 8,016,777 B1 | 9/2011 | Egorov et al. |
| 8,052,622 B2 | 11/2011 | Egorov et al. |
| 8,069,735 B1 | 12/2011 | Egorov et al. |
| 8,142,368 B2 | 3/2012 | Egorov et al. |
| 8,187,208 B2 | 5/2012 | Egorov et al. |
| 8,419,659 B2 | 4/2013 | Egorov et al. |
| 8,480,404 B2 | 7/2013 | Savitsky |
| 8,814,807 B2 | 8/2014 | Hulvershorn et al. |
| 9,179,875 B2 | 11/2015 | Hua |
| 10,383,610 B2 | 8/2019 | Moskowitz et al. |
| 2004/0010204 A1 | 1/2004 | Weber et al. |
| 2004/0254503 A1 | 12/2004 | Sarvazyan et al. |
| 2004/0267121 A1 | 12/2004 | Sarvazyan et al. |
| 2004/0267165 A1 | 12/2004 | Sarvazyan et al. |
| 2005/0075665 A1 | 4/2005 | Brenzel et al. |
| 2006/0122555 A1 | 6/2006 | Hochman |
| 2006/0195043 A1 | 8/2006 | Rutherford et al. |
| 2006/0206178 A1 | 9/2006 | Kim |
| 2008/0154154 A1 | 6/2008 | Sarvazyan et al. |
| 2009/0018507 A1 | 1/2009 | Schmitz et al. |
| 2009/0131832 A1 | 5/2009 | Sacristan et al. |
| 2009/0143656 A1* | 6/2009 | Manwaring ............ A61B 5/026 600/324 |
| 2009/0157044 A1 | 6/2009 | Liyanagama et al. |
| 2009/0270759 A1 | 10/2009 | Wilson et al. |
| 2010/0256483 A1 | 10/2010 | Wall et al. |
| 2011/0066078 A1 | 3/2011 | Sarvazyan et al. |
| 2011/0092818 A1 | 4/2011 | Sarvazyan |
| 2011/0166442 A1 | 7/2011 | Sarvazyan |
| 2012/0046531 A1 | 2/2012 | Hua |
| 2012/0143029 A1 | 6/2012 | Silverstein et al. |
| 2012/0296213 A1 | 11/2012 | Mauldin, Jr. et al. |
| 2013/0023880 A1 | 1/2013 | Tramboo et al. |
| 2013/0085413 A1 | 4/2013 | Tsamir et al. |
| 2014/0046186 A1 | 2/2014 | Mauldin, Jr. et al. |
| 2014/0276925 A1 | 9/2014 | Alves et al. |
| 2014/0277045 A1 | 9/2014 | Fazio et al. |
| 2014/0288408 A1 | 9/2014 | Deutsch |
| 2014/0288427 A1 | 9/2014 | Wall |
| 2014/0303494 A1 | 10/2014 | Janicki et al. |
| 2015/0025363 A1 | 1/2015 | Hulvershorn et al. |
| 2015/0245809 A1* | 9/2015 | Hagy .................. A61B 8/4411 600/461 |
| 2015/0342635 A1 | 12/2015 | Tsamir et al. |
| 2015/0359563 A1 | 12/2015 | Kume et al. |
| 2016/0008007 A1 | 1/2016 | Taha |
| 2016/0157816 A1 | 6/2016 | Denny |
| 2016/0270810 A1 | 9/2016 | Vardi et al. |
| 2017/0020540 A1 | 1/2017 | Chou et al. |
| 2017/0319127 A1 | 11/2017 | Moskowitz et al. |
| 2019/0231332 A1 | 8/2019 | Moskowitz et al. |

FOREIGN PATENT DOCUMENTS

| | | |
|---|---|---|
| CN | 104140066 A | 11/2014 |
| CN | 104523297 A | 4/2015 |
| CN | 204318870 U | 5/2015 |
| EP | 0303824 A2 | 2/1989 |
| EP | 2223662 A1 | 9/2010 |
| JP | S62281927 A | 12/1987 |
| WO | WO-9215256 A1 | 9/1992 |
| WO | WO-2007022599 A1 | 3/2007 |
| WO | WO-2007024399 A2 | 3/2007 |
| WO | WO-2009009621 A2 | 1/2009 |
| WO | WO-2009066972 A1 | 5/2009 |
| WO | WO-2010018536 A2 | 2/2010 |
| WO | WO-2011084788 A2 | 7/2011 |
| WO | WO-2011158227 A2 | 12/2011 |
| WO | WO-2013054165 A1 | 4/2013 |
| WO | WO-2013056243 A1 | 4/2013 |
| WO | WO-2014097301 A1 | 6/2014 |
| WO | WO-2015200712 A1 | 12/2015 |
| WO | WO-2016007527 A1 | 1/2016 |
| WO | WO-2016034910 A1 | 3/2016 |
| WO | WO-2018148456 A1 | 8/2018 |
| WO | WO-2019084502 A1 | 5/2019 |

OTHER PUBLICATIONS

U.S. Appl. No. 15/584,875 First Action Interview Office Action Summary dated Oct. 12, 2017.
U.S. Appl. No. 15/584,875 First Action Interview Pilot Program, Pre-Interview Communication dated Jul. 17, 2017.
European Patent Application No. 17793167.2 Extended European Search Report dated Oct. 31, 2019.
International Application No. PCT/US2018/057860 International Search Report and Written Opinion dated Mar. 11, 2019.
PCT/US2018/017487 International Search Report and Written Opinion dated May 21, 2018.

* cited by examiner

TACTILE SENSING DEVICE FOR LUMBAR PUNCTURES

CROSS-REFERENCE

This application is a continuation of U.S. application Ser. No. 15/584,875, filed on May 2, 2017, which claims the benefit of priority to U.S. Provisional Application 62/331,279, filed on May 3, 2016, and U.S. Provisional Application No. 62/484,354, filed Apr. 11, 2017, each of which are incorporated herein by reference in their entireties.

SUMMARY

Disclosed herein, in certain embodiments, are tactile sensing devices, systems, methods, and kits for imaging bone and non-bone structures in an individual in need thereof. In certain embodiments, also described herein are methods for performing a lumbar puncture utilizing the tactile sensing device. In certain embodiments, also described herein are methods for administering a therapeutic to an epidural space of an individual utilizing the tactile sensing device.

Accessing the epidural or subarachnoid space via a lumbar puncture is a technically challenging procedure that is performed quite commonly in the clinic, especially in the Emergency Room. The procedure involves "blindly" landmarking, or landmarking by manually palpating, the lumbar spine, to identify a gap between two spinous processes through which a needle can be inserted into the epidural or subarachnoid space for fluid collection or injection. The "blind" landmarking technique improves with time and practice therefore, physicians with limited experience find the lumbar puncture procedure challenging. Furthermore, regardless of experience, the lumbar puncture procedure becomes difficult to perform with obese patients or patients with a high body mass index (BMI) because their high accumulation of subcutaneous adipose tissue prevents the physician to accurately landmark the lumbar spine via manual palpation. Current landmarking techniques only have a 30% accuracy, making it necessary for an average of >4 attempts to properly puncture the space, and resulting in >25% of patients having traumatic lumbar punctures and >32% of patients left with post-dural puncture headaches (PDPHs). Additionally, elderly patients or pregnant patients have limited flexibility and are unable to maximally flex the hips, knees, and back, as is required during a lumbar puncture procedure in order to increase the opening space between the intervertebral disks. Beyond just landmarking and localization, other functional steps of performing a diagnostic lumbar puncture, where cerebrospinal fluid (CSF) samples are collected and intracranial pressure is measured, are severely inefficient. In order to obtain an intracranial pressure reading, physicians use a two-piece manometer connected to a needle hub by a three-way stopcock, which requires estimation of fluid levels in determining intracranial pressure. To simultaneously balance a manometer and one or more cerebrospinal fluid collection tubes requires significant dexterity and/or sometimes more than one pair of hands. Thus, the risk of CSF spillages is high and further increases the risk of contamination. Accordingly, there is a need for improved devices, methods, systems, and kits to perform a lumbar puncture. There is also a need for improved devices, methods, systems and kits to visualize bone and non-bone structures. In view of these deficiencies in the current state of the art, the subject matter presented herein addresses these and other needs.

Disclosed herein, in certain embodiments, are tactile sensing devices for imaging a target tissue location in an individual in need thereof, comprising: a) a needle guide having a proximal opening and a distal opening, configured for guiding a needle towards the individual; and b) a sensor array comprising at least one sensor configured to detect applied pressure.

Disclosed herein, in certain embodiments, are tactile sensing devices for imaging a target tissue location in an individual in need thereof, comprising: a) a needle guide cartridge comprising at least two needle guides, wherein each needle guide has a side opening and a distal opening, and each needle guide is configured for guiding a needle towards the individual; and b) a sensor array comprising at least one sensor configured to detect applied pressure.

Disclosed herein, in certain embodiments, are tactile sensing devices for imaging a target tissue location in an individual in need thereof, comprising: a) a sensor array comprising at least one sensor configured to detect applied pressure; b) a display screen; and c) a marking tool to mark the target tissue location.

Disclosed herein, in certain embodiments, are tactile sensing devices for imaging a target tissue location in an individual in need thereof, comprising: a) a sensor array comprising at least one sensor configured to detect applied pressure; b) a connection to a display screen; and c) a marking tool to mark the target tissue location.

In some embodiments, the needle guide cartridge allows for the needle to be inserted into the individual at more than one level. In some embodiments, the needle guide allows for the needle to be inserted into the individual at more than one angle. In some embodiments, the angle is a cephalad angle between about −45 degrees to about 45 degrees. In some embodiments, the angle is a 15 degree cephalad angle. In some embodiments, the sensor array is configured to be loaded into a sensor array holder. In some embodiments, the tactile sensing devices further comprise a frame. In some embodiments, the frame further comprises an elongated portion carrying the needle guide, a downwardly elbowed portion serving as a handle, and a sensor array holder positioned distally away from the handle. In some embodiments, the tactile sensing devices further comprise a display screen positioned directly above the sensor array. In some embodiments, the display screen is configured to display the target tissue location and the needle to be inserted into the individual. In some embodiments, the display screen is a computer screen, a mobile device screen, a liquid crystal display (LCD), a thin film transistor liquid crystal display (TFT-LCD), or an organic light emitting diode (OLED) display. In some embodiments, the tactile sensing devices further comprise a needle hub connector that connects to the needle, configured to be inserted through an opening of the needle guide. In some embodiments, the opening of the needle guide is the proximal opening of the needle guide or a knob opening of the needle guide. In some embodiments, the tactile sensing devices further comprise a knob that is coupled to a needle hub connector or extends from a needle hub connector. In some embodiments, the knob protrudes from a side opening or a slit. In some embodiments, the tactile sensing devices further comprise a valve. In some embodiments, the valve is a 3-way valve or a 3-way stopcock valve. In some embodiments, the valve is configured to be inserted through a knob opening of a needle guide. In some embodiments, the valve is fixed onto a needle guide cartridge. In some embodiments, the valve further comprises a needle hub connector, a fluid connector, a fluid port, a pressure gauge connector, a pressure gauge port, or a combination thereof. In some embodiments, the tactile sensing devices further comprise a fluid collection system. In some embodiments, the fluid collection system is a faucet fluid collection system, rail fluid collection system, diaphragm fluid collection system, or spoke fluid collection system. In some embodiments, the faucet fluid collection system comprises at least one collection tube, a central rod extending downwardly from a frame, a faucet base extending downwardly from the central rod, and a rotating handle for generating a rotational movement, said rotating handle coupled to the faucet base, wherein at least one collection tube sits on the faucet base. In some embodiments, the rail fluid collection system comprises a pair of guide rails extending beneath a needle guide cartridge, said guide rails configured to receive a sliding rail platform, said rail platform comprising at least one opening, said opening configured to hold at least one collection tube. In some embodiments, the diaphragm fluid collection system comprises at least one collection tube, at least one diaphragm, at least one rotating band allowing the diaphragm to be opened or closed, and a cap configured to be secured onto a first collection tube. In some embodiments, the spoke fluid collection system comprises a central hub; at least one central hub opening located on a side surface of the central hub, said central hub opening configured to connect to at least one collection tube; and a spoke connector extending outwardly from a front face of the central hub. In some embodiments, the needle is a spinal needle, an epidural needle, or a biopsy needle. In some embodiments, the sensor array is a 6×3 sensor array comprising eighteen sensors. In some embodiments, the sensor array is an 8×4 array comprising thirty two sensors. In some embodiments, the sensor array is secured onto a platform. In some embodiments, the platform comprises projections onto which the sensors are adhered to. In some embodiments, the projections are struts or connectors. In some embodiments, the sensor is covered with a material configured to enhance force feedback. In some embodiments, the sensor is a force-sensitive resistor. In some embodiments, the marking tool is a light, an ink, a hydrogel, a nanoparticle. In some embodiments, the light is a laser light or a light emitting diode (LED). In some embodiments, the ink is a permanent ink, a gentian violent ink, a water-based ink, an oil-based in, a liquid ink, or a gel ink. In some embodiments, the hydrogel further comprises a contrast agent. In some embodiments, the nanoparticle further comprises a contrast agent. In some embodiments, the tactile sensing devices further comprise a multiplexer. In some embodiments, the tactile sensing devices further comprise a voltage divider. In some embodiments, the tactile sensing devices further comprise a voltage source. In some embodiments, the tactile sensing devices further comprise a pressure sensor operatively connected to the tactile sensing device and configured to measure an intracranial pressure. In some embodiments, the pressure sensor is a piezoresistive pressure sensor, a capacitive pressure sensor, an electromagnetic pressure sensor, a piezoelectric pressure sensor, an optical pressure sensor, or a potentiometric pressure sensor.

Disclosed herein, in certain embodiments, are systems for imaging a target tissue location in an individual in need thereof, comprising: a) a tactile sensing device; and b) a computing device comprising: i) at least one processor operatively coupled to the tactile sensing device; ii) a memory device; and iii) a non-transitory computer readable storage medium with a computer program including instructions executable by the processor causing the processor to convert a voltage signal into an image. In some embodiments, the computing device is a microcontroller. In some embodiments, the computing device further comprises a second computer program including instructions executable by the processor that cause the processor to encode the voltage signal into a first computer signal and a second computer signal. In some embodiments, the systems further comprise a transmitter configured to transmit the first computer signal to the computing device. In some embodiments, the systems further comprise a receiver configured to receive the second computer signal from the tactile sensing device. In some embodiments, the first and second computer signals are transmitted remotely, directly, wirelessly, or via a wire. In some embodiments, the first computer signal and the second computer signals are wireless signals. In some embodiments, the computing device is a mobile device. In some embodiments, the computing device further comprises a third computer program including instructions executable by the processor that cause the processor to calculate a projected needle position and display it on the display screen. In some embodiments, the computing device further comprises a fourth computer program including instructions executable by the processor causing the processor to: a) determine, as a first requirement, a location of a target tissue location detected by the tactile sensing device; and b) perform predictive analysis based on application of machine learning to approximate the projected needle position.

Disclosed herein, in certain embodiments, are methods for imaging a target tissue location in an individual in need thereof, comprising: a) placing a tactile sensing device on the individual; b) applying force to the tactile sensing device against the individual; and c) viewing an image of the target tissue location, obtained from voltage signals generated by the tactile sensing device, resulting from the application of force to the tactile sensing device against an individual, on a display screen.

Disclosed herein, in certain embodiments, are methods for generating an image of a target tissue location in an individual in need thereof, comprising: a) collecting a plurality of voltage signals generated by a tactile sensing device, resulting from the application of force to the tactile sensing device against an individual; b) converting the voltage signals into a mathematical array; c) rescaling the mathematical array; and d) transforming the rescaled mathematical array into the image of a target tissue location of the individual.

In some embodiments, the target tissue location is a bone structure. In some embodiments, the bone structure is an articular surface. In some embodiments, the articular surface is a vertebral articulation, an articulation of a first bone of a hand with a second bone of the hand, an elbow joint, a wrist joint, an axillary articulation of a first bone of a shoulder with a second bone of the shoulder, a sternoclavicular joint, a temporomandibular joint, a sacroiliac joint, a hip joint, a knee joint, or an articulation of a first bone of a foot with a second bone of the foot. In some embodiments, the vertebral articulation is a spinous process. In some embodiments, the target tissue location is a subcutaneous tissue, a muscle, a ligament, an adipose tissue, a cyst, a cavity, or a tumor mass. In some embodiments, placing the tactile sensing device on the individual further comprises positioning the tactile sensing device on a bone structure. In some embodiments, the bone structure is a vertebral column of an individual. In some embodiments, collecting the plurality of voltage signals further comprises transmitting the data via a multiplexer. In some embodiments, collecting the plurality of the voltage signals further comprises transmitting the data via a voltage divider. In some embodiments, converting the plurality of the voltage signals comprises acquiring, processing, and transforming the plurality of voltage signals into the image using a computer processor. In some embodiments, the image is a pressure map representing the target tissue location. In some embodiments, the pressure map is overlaid on top of a structural spinal image.

Disclosed herein, in certain embodiments, are methods for performing a lumbar puncture in an individual in need thereof, comprising: a) placing a tactile sensing device on a lumbar region of the individual; b) applying force to the tactile sensing device against the lumbar region; c) viewing an image of vertebral articulations on a display screen; wherein the image is generated by the tactile sensing device resulting from the application of force to the tactile sensing device against the lumbar region; d) localizing two spinous processes on the image; e) identifying a gap between a first spinous process and a second spinous process of the individual; f) using a needle guide to insert a needle between the first and second spinous processes of the individual and into a subarachnoid space; and g) collecting cerebrospinal fluid or administering a therapeutic agent. In some embodiments, the therapeutic agent is an analgesic, an anesthetic, a chemotherapeutic agent, or a contrast agent or dye.

Disclosed herein, in certain embodiments, are methods for administering a therapeutic agent to an epidural space of an individual in need thereof, comprising: a) placing a tactile sensing device on a lumbar region of the individual; b) applying force to the tactile sensing device against the lumbar region; c) viewing an image of vertebral articulations on a display screen; wherein the image is detected by the tactile sensing device resulting from the application of force to the tactile sensing device against the lumbar region; d) localizing two spinous processes on the image; e) identifying a gap between a first spinous process and a second spinous process of the individual; f) using a needle guide to insert a needle between the first and second spinous processes and into the epidural space of the individual; and g) injecting a therapeutic agent into the epidural space. In some embodiments, the therapeutic agent is an analgesic, an anesthetic, a contrast agent or dye, a chemotherapeutic agent, or a steroid. In some embodiments, the first spinous process is a part of L1, L2, L3, or L4 lumbar vertebrae and the second spinous process is a part of L2, L3, L4, or L5 lumbar vertebrae. In some embodiments, the needle is a traumatic or an atraumatic needle. In some embodiments, the methods further comprise using a stylet or a catheter in conjunction with the needle.

Disclosed herein, in certain embodiments, are methods for guiding a first individual performing a lumbar puncture on a second individual in need thereof, comprising: a) placing a tactile sensing device on a lumbar region of the individual; b) applying force to the tactile sensing device against the lumbar region; c) viewing an image of vertebral articulations on a display screen, wherein the image is generated by the tactile sensing device resulting from the application of force to the tactile sensing device against the lumbar region; d) localizing two spinous processes on the image; e) identifying a gap between a first spinous process and a second spinous process of the individual; f) using a needle guide to insert a needle between the first and second spinous processes of the individual and into a subarachnoid space; and g) collecting cerebrospinal fluid or administering a therapeutic agent.

Disclosed herein, in certain embodiments, are methods for guiding a first individual administering a therapeutic agent into an epidural space of a second individual in need thereof, comprising: a) placing a tactile sensing device on a lumbar region of the individual; b) applying force to the tactile sensing device against the lumbar region; c) viewing an image of vertebral articulations on a display screen, wherein the image is generated by the tactile sensing device resulting from the application of force to the tactile sensing device against the lumbar region; d) localizing two spinous processes on the image; e) identifying a gap between a first spinous process and a second spinous process of the individual; f) using a needle guide to insert a needle between the first and second spinous processes and into the epidural space of the individual; and g) injecting a therapeutic agent into the epidural space.

Disclosed herein, in certain embodiments, are methods for imaging a target tissue location in an individual in need thereof, comprising: a) placing a tactile sensing device on the individual; b) applying force to the tactile sensing device against the individual; and c) viewing an image of the target tissue location, obtained from voltage signals generated by the tactile sensing device, resulting from the application of force to the tactile sensing device against an individual, on a display screen.

Disclosed herein, in certain embodiments, are methods for generating an image of a target tissue location in an individual in need thereof, comprising: a) collecting a plurality of voltage signals generated by a tactile sensing device, resulting from the application of force to the tactile sensing device against an individual; b) converting the voltage signals into a mathematical array; c) rescaling the mathematical array; and d) transforming the rescaled mathematical array into the image of a target tissue location of the individual. In some embodiments, the target tissue location is a bone structure. In some embodiments, the bone structure is an articular surface. In some embodiments, the articular surface is a vertebral articulation, an articulation of a first bone of a hand with a second bone of the hand, an elbow joint, a wrist joint, an axillary articulation of a first bone of a shoulder with a second bone of the shoulder, a sternoclavicular joint, a temporomandibular joint, a sacroiliac joint, a hip joint, a knee joint, or an articulation of a first bone of a foot with a second bone of the foot. In some embodiments, a vertebral articulation is a spinous process. In some embodiments, the target tissue location is a subcutaneous tissue, a muscle, a ligament, an adipose tissue, a cyst, a cavity, or a tumor mass. In some embodiments, placing the tactile sensing device on the individual further comprises positioning the tactile sensing device on a bone structure. In some embodiments, the bone structure is a vertebral column of an individual. In some embodiments, the tactile sensing device comprises an array of force-sensitive resistors. In some embodiments, the array of force-sensitive resistors is a 6×3 array comprising eighteen force-sensitive resistors. In some embodiments, the array of force-sensitive resistors is an 8×4 array comprising thirty two force-sensitive resistors. In some embodiments, the array of force-sensitive resistors is secured onto a platform. In some embodiments, the platform comprises projections onto which the force-sensitive resistors are adhered to. In some embodiments, the projections are struts or connectors. In some embodiments, the force-sensitive resistors are covered with a material configured to enhance force feedback. In some embodiments, the material configured to enhance force feedback is a hemispherical rubber disk. In some embodiments, collecting the plurality of voltage signals further comprises transmitting the data via a multiplexer. In some embodiments, collecting the plurality of the voltage signals further comprises transmitting the data via a voltage divider. In some embodiments, converting the plurality of the voltage signals comprises acquiring, processing, and transforming the plurality of voltage signals into the image using a computer processor. In some embodiments, the image is a pressure map representing the target tissue location. In some embodiments, the pressure map is overlaid on top of a structural spinal image.

Disclosed herein, in certain embodiments, are methods for performing a lumbar puncture in an individual in need thereof, comprising: a) placing a tactile sensing device on a lumbar region of the individual; b) applying force to the tactile sensing device against the lumbar region; c) viewing an image of vertebral articulations on a display screen; wherein the image is generated by the tactile sensing device resulting from the application of force to the tactile sensing device against the lumbar region; d) localizing two spinous processes on the image; e) identifying a gap between a first spinous process and a second spinous process of the individual; f) using a needle guide to insert a needle between the first and second spinous processes of the individual and into a subarachnoid space; and g) collecting cerebrospinal fluid or administering a therapeutic agent. In some embodiments, the therapeutic agent is an analgesic, an anesthetic, a chemotherapeutic agent, or a contrast agent or dye.

Disclosed herein, in certain embodiments, are methods for administering a therapeutic agent to an epidural space of an individual in need thereof, comprising: a) placing a tactile sensing device on a lumbar region of the individual; b) applying force to the tactile sensing device against the lumbar region; c) viewing an image of vertebral articulations on a display screen; wherein the image is detected by the tactile sensing device resulting from the application of force to the tactile sensing device against the lumbar region; d) localizing two spinous processes on the image; e) identifying a gap between a first spinous process and a second spinous process of the individual; f) using a needle guide to insert a needle between the first and second spinous processes and into the epidural space of the individual; and g) injecting a therapeutic agent into the epidural space. In some embodiments, the therapeutic agent is an analgesic, an anesthetic, a contrast agent or dye, a chemotherapeutic agent, or a steroid. In some embodiments, the first spinous process is a part of L1, L2, L3, or L4 lumbar vertebrae and the second spinous process is a part of L2, L3, L4, or L5 lumbar vertebrae. In some embodiments, the needle is a traumatic or an atraumatic needle. In some embodiments, the methods further comprise using a stylet or a catheter in conjunction with the needle. In some embodiments, the needle guide is oriented between −45° and 45° cephalad angle and terminating at an opening located on the center of the tactile sensing device, thereby controlling the angle at which the needle is inserted into a human body. In some embodiments, the opening located on the center of the tactile sensing device is an elongated slit. In some embodiments, the needle guide is oriented at a 15° cephalad angle. In some embodiments, the needle guide terminates at a plurality of openings formed by an elongated slit with a plurality of columns. In some embodiments, the methods further comprise using a plurality of needle guides oriented between a −45° and 45° cephalad angle and terminating at a plurality of openings located along the midline of the tactile sensing device, thereby controlling the angle at which the needle is inserted into a human body. In some embodiments, the methods further comprise using a plurality of needle guides oriented at a 15° cephalad angle. In some embodiments, the plurality of needle guides terminates at an opening. In some embodiments, the opening is an elongated slit.

Disclosed herein, in certain embodiments, are methods for guiding a first individual performing a lumbar puncture on a second individual in need thereof, comprising: a) placing a tactile sensing device on a lumbar region of the individual; b) applying force to the tactile sensing device against the lumbar region; c) viewing an image of vertebral articulations on a display screen, wherein the image is generated by the tactile sensing device resulting from the application of force to the tactile sensing device against the lumbar region; d) localizing two spinous processes on the image; e) identifying a gap between a first spinous process and a second spinous process of the individual; f) using a needle guide to insert a needle between the first and second spinous processes of the individual and into a subarachnoid space; and g) collecting cerebrospinal fluid or administering a therapeutic agent.

Disclosed herein, in certain embodiments, are methods for guiding a first individual administering a therapeutic agent into an epidural space of a second individual in need thereof, comprising: a) placing a tactile sensing device on a lumbar region of the individual; b) applying force to the tactile sensing device against the lumbar region; c) viewing an image of vertebral articulations on a display screen, wherein the image is generated by the tactile sensing device resulting from the application of force to the tactile sensing device against the lumbar region; d) localizing two spinous processes on the image; e) identifying a gap between a first spinous process and a second spinous process of the individual; f) using a needle guide to insert a needle between the first and second spinous processes and into the epidural space of the individual; and g) injecting a therapeutic agent into the epidural space.

Disclosed herein, in certain embodiments, are tactile sensing devices for imaging a target tissue location in an individual in need thereof, comprising: a needle guide having a proximal opening and a distal opening, configured for guiding a needle towards the individual; wherein said needle guide allows for the needle to be inserted into the individual at about a 15° cephalad angle; a sensor array comprising at least one sensor configured to output a signal in response to a change in force applied to its surface; and a fluid collection system positioned within a handle, comprising at least one collection tube, a central rod extending downwardly from a frame, a faucet base extending downwardly from the central rod, and a rotating handle for generating rotational movement, said rotating handle coupled to the faucet base, wherein at least one collection tube sits on the faucet base. In some embodiments, the needle guide allows for the needle to be inserted into the individual at a cephalad angle between about 10° and about 20°. In some embodiments, the sensor array is configured to be loaded into a sensor array holder. In some embodiments, the sensor is a force-sensitive resistor. In some embodiments, the tactile sensing devices further comprise a frame. In some embodiments, the frame further comprises an elongated portion carrying the needle guide, a downwardly elbowed portion serving as the handle, and a sensor array holder positioned distally away from the handle. In some embodiments, the signal is converted to a pressure map. In some embodiments, the pressure map represents a target tissue location in an individual. In some embodiments, the pressure map displays a position of a needle at a skin level and a projected position of a needle. In some embodiments, the tactile sensing devices further comprise a 3-way valve configured to be inserted through the proximal opening of the needle guide, and retained within the needle guide, said 3-way valve comprising a needle hub connector, a fluid port, and a pressure gauge connector. In some embodiments, the needle hub connector connects to the needle. In some embodiments, the fluid port is an open port through which a fluid flows freely. In some embodiments, the pressure gauge connector is configured to connect to a pressure sensor. In some embodiments, the pressure sensor measures an intracranial pressure. In some embodiments, the pressure sensor is a piezoresistive pressure sensor, a capacitive pressure sensor, an electromagnetic pressure sensor, a piezoelectric pressure sensor, an optical pressure sensor, or a potentiometric pressure sensor. In some embodiments, the tactile sensing devices further comprise a knob that is coupled to a needle hub connector or extends from a needle hub connector. In some embodiments, the knob protrudes from a side opening or a slit. In some embodiments, the fluid collection system is a faucet fluid collection system, a rail fluid collection system, a diaphragm fluid a collection system, or a spoke fluid collection system.

BRIEF DESCRIPTION OF THE DRAWINGS

The novel features of the subject matter disclosed herein are set forth with particularity in the appended claims. A better understanding of the features and advantages of the subject matter disclosed herein will be obtained by reference to the following detailed description that sets forth illustrative embodiments, in which the principles of the subject matter disclosed herein are utilized, and the accompanying drawings of which:

FIG. 1A shows a front view of the tactile sensing device 1000 with an exemplary output image displayed on its display screen 1032. FIG. 1B shows a cross-section view of the tactile sensing device 1000. FIG. 1C shows a wire frame side view of the tactile sensing device 1000.

FIG. 2A shows a side view of the tactile sensing device 2000 with an exemplary output image displayed on its display screen 2032. FIG. 2B shows a side view of the tactile sensing device 2000. FIG. 2C shows a cross-section view of the tactile sensing device 2000.

FIG. 3A shows a side view of the sensor array 3008. FIG. 3B shows a front view of the sensor array 3008.

FIG. 9A shows voltage values across a single sensor, when the sensor is moved in 1 cm increments, as a function of a force applied (in units of grams). FIG. 9B shows the normalized voltage of a column of 6 sensors for six different trials. A fixed and equal force was applied onto the column of six sensors for each trial.

FIG. 11A is a visual representation of underlying bony landmarks as detected and generated by the tactile sensing device. FIG. 11B illustrates a needle's position at the skin level ("original") and its projected subcutaneous location on a pressure map generated by the tactile sensing device.

DETAILED DESCRIPTION

Figure 1A:
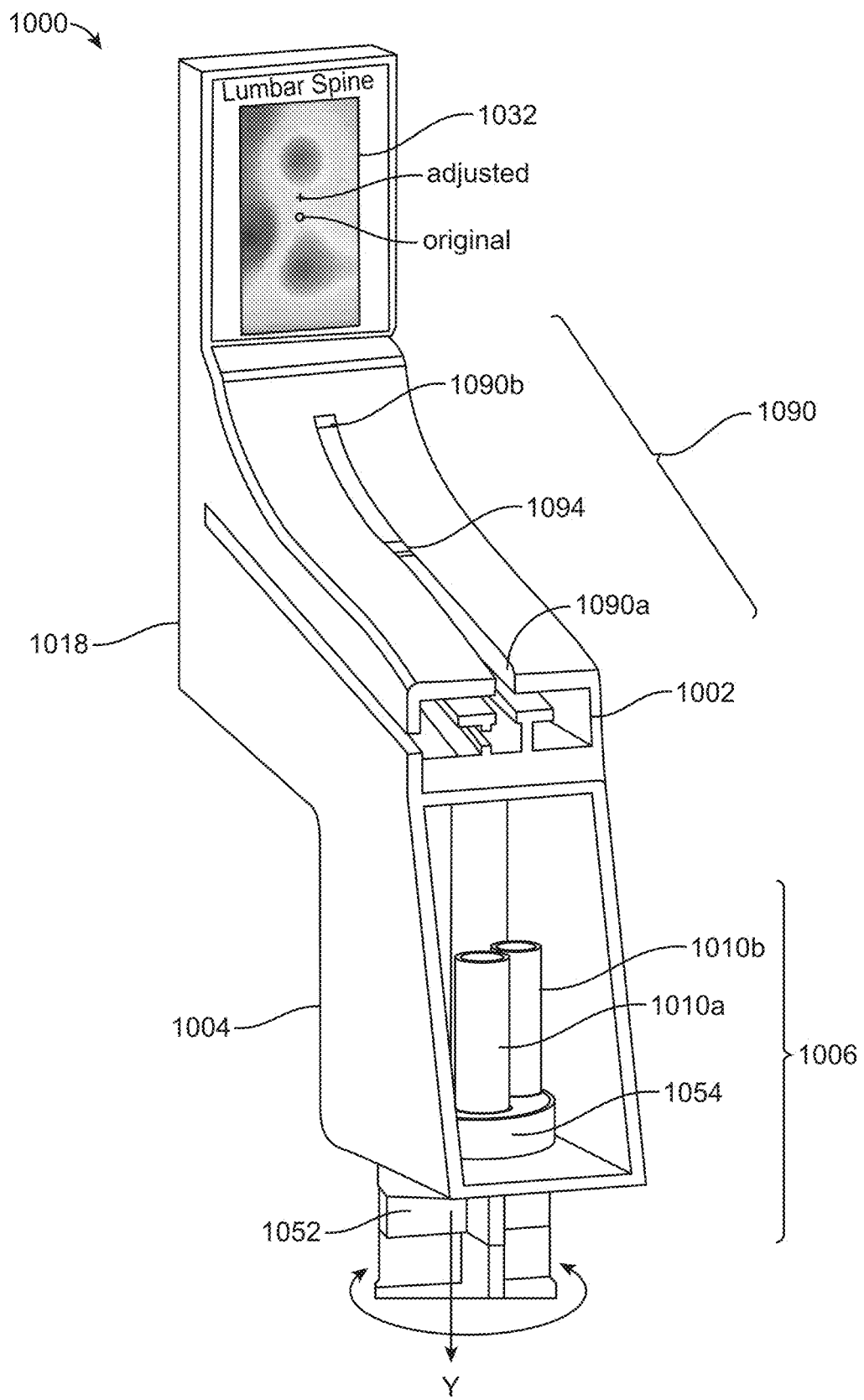
FIGS. 1A-C illustrate a tactile sensing device with a faucet fluid collection system.

While preferred embodiments of the subject matter disclosed herein have been shown and described herein, it will be obvious to those skilled in the art that such embodiments are provided by way of example only. Numerous variations, changes, and substitutions will now occur to those skilled in the art without departing from the subject matter disclosed herein. It should be understood that various alternatives to the embodiments of the subject matter disclosed herein may be employed in practicing the subject matter disclosed herein. It is intended that the following claims define the scope of the subject matter disclosed herein and that methods and structures within the scope of these claims and their equivalents be covered thereby.

Certain Definitions

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" means within an acceptable error range for the particular value as determined by one of ordinary skill in the art, which will depend in part on how the value is measured or determined, e.g., the limitations of the measurement system. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, 0.1%, or 0.05% of a given value or range. In certain embodiments, the term "about" or "approximately" means within 20.0 degrees, 15.0 degrees, 10.0 degrees, 9.0 degrees, 8.0 degrees, 7.0 degrees, 6.0 degrees, 5.0 degrees, 4.0 degrees, 3.0 degrees, 2.0 degrees, 1.0 degrees, 0.9 degrees, 0.8 degrees, 0.7 degrees, 0.6 degrees, 0.5 degrees, 0.4 degrees, 0.3 degrees, 0.2 degrees, 0.1 degrees, 0.09 degrees. 0.08 degrees, 0.07 degrees, 0.06 degrees, 0.05 degrees, 0.04 degrees, 0.03 degrees, 0.02 degrees or 0.01 degrees of a given value or range.

The terms "individual," "patient," or "subject" are used interchangeably. None of the terms require or are limited to situation characterized by the supervision (e.g. constant or intermittent) of a health care worker (e.g. a doctor, a registered nurse, a nurse practitioner, a physician's assistant, an orderly, or a hospice worker).

The terms "user," "health care worker," "doctor," and "physician" are used interchangeably. These terms refer to any person that operates the devices described herein. Additional non-liming examples of a user include "registered nurse," "nurse practitioner," and "physician's assistant."

The terms "intracranial pressure (ICP)" and "cerebrospinal fluid (CSF) pressure" are used interchangeably. ICP is the pressure inside a skull and thus, it is the pressure in the brain tissue and CSF.

The terms "lumbar puncture" and "spinal tap" are used interchangeably herein.

The term "needle hub," as used herein, refers to the hub at one end of a needle that commonly attaches to a syringe. The shaft of the needle is an elongated, slender stem of the needle that extends from the needle hub and is beveled at the end opposite to the needle hub end.

Accessing the epidural or subarachnoid space via a lumbar puncture is a technically challenging procedure that is performed quite commonly in the clinic, especially in the Emergency Room. The procedure involves "blindly" landmarking, or landmarking by manually palpating, the lumbar spine, to identify a gap between two spinous processes through which a needle can be inserted into the epidural or subarachnoid space for fluid collection or injection. The "blind" landmarking technique improves with time and practice therefore, physicians with limited experience find the lumbar puncture procedure challenging. Furthermore, regardless of experience, the lumbar puncture procedure becomes difficult to perform with obese patients or patients with a high body mass index (BMI) because their high accumulation of subcutaneous adipose tissue prevents the physician to accurately landmark the lumbar spine via manual palpation. Current landmarking techniques only have a 30% accuracy, making it necessary for an average of >4 attempts to properly puncture the space, and resulting in >25% of patients having traumatic lumbar punctures and >32% of patients left with post-dural puncture headaches (PDPHs). Additionally, elderly patients or pregnant patients have limited flexibility and are unable to maximally flex the hips, knees, and back, as is required during a lumbar puncture procedure in order to increase the opening space between the intervertebral disks. Beyond just landmarking and localization, other functional steps of performing a diagnostic lumbar puncture, where cerebrospinal fluid (CSF) samples are collected and intracranial pressure is measured, are severely inefficient. In order to obtain an intracranial pressure reading, physicians use a two-piece manometer connected to a needle hub by a three-way stopcock, which requires estimation of fluid levels in determining intracranial pressure. To simultaneously balance a manometer and one or more cerebrospinal fluid collection tubes requires significant dexterity and/or sometimes more than one pair of hands. Thus, the risk of CSF spillages is high and further increases the risk of contamination. Accordingly, there is a need for improved devices, methods, systems, and kits to perform a lumbar puncture. There is also a need for improved devices, methods, systems and kits to visualize bone and non-bone structures. In view of these deficiencies in the current state of the art, the subject matter presented herein addresses these and other needs.

Lumbar Punctures

A lumbar puncture is an invasive procedure performed in a clinical setting for diagnostic or therapeutic purposes. A diagnostic lumbar puncture, also known as "spinal tap," is one of the most commonly invasive tests performed in the clinic. Every year, approximately 400,000 diagnostic lumbar punctures are performed in the United States. During a lumbar puncture, cerebrospinal fluid is collected and in some cases, cerebrospinal fluid (CSF) opening pressure is measured. Therapeutic lumbar punctures are most commonly performed to deliver spinal anesthesia, intrathecal chemotherapeutics, intrathecal pain killers, intrathecal antibiotics, and contrast agents.

In some instances, a lumbar puncture is performed with a patient in a lateral decubitus position or lying down on their side, knees bent, and head in a neutral position. In some instances, a lumbar puncture is performed with a patient upright, seated with the chin down and feet supported. Aseptic technique is used when performing a lumbar puncture. In some instances, to perform a lumbar puncture, a practitioner performs a series of steps including: identifying an intraspineous process space between the $4^{th}$ and $5^{th}$ lumbar vertebrae (L4 and L5), between L3 and L4, or between L2 and L3; cleaning the patient's skin in the lumbar area with iodinated solution, ethanol or isopropyl alcohol, and chlorhexidine; administering a local anesthetic such as, but not limited to, xylocaine or lidocaine, in a manner such that it raises a small bleb on the skin; administering additional local anesthetic, such as lidocaine, to deeper subcutaneous and intraspinous tissues; slowly inserting a spinal needle angling towards the patient's head until the epidural or subarachnoid space is entered.

Diagnostic Lumbar Puncture

During a diagnostic lumbar puncture, a needle is inserted between two lumbar vertebrae and into the spinal canal in order to remove a sample(s) of cerebrospinal fluid (CSF), which surrounds the brain and the spinal cord. In some instances, the CSF is collected and its physical, chemical, microscopic, and infectious properties are inspected. Physical properties of CSF that are checked include: color, turbidity, and viscosity. Chemical components of CSF that are routinely tested for include glucose and proteins. However, additional testing includes: protein electrophoresis to distinguish different types of protein; immunoglobulin G (IgG) detection; myelin basic protein detection; lactic acid detection; lactate dehydrogenase detection; glutamine detection; C-reactive protein detection; tumor markers such as carcinoembryonic antigen (CEA), alpha-fetoprotein (AFP), and human chorionic gonadotropin (hCG); amyloid beta 42 (Aβ42) protein detection; and tau protein detection. Microscopic examination of CSF comprises analyzing the sample for total cell counts including red and white blood cells; additionally, in some instances, a cytology test is performed to determine the presence or absence of abnormal cells such as tumor cells or immature blood cells. Infectious tests performed include: CSF gram stain, culture, and sensitivity test to detect microorganisms and predict best choices for antimicrobial therapy; detection of viruses using polymerase chain reaction (PCR); detection of CSF cryptococcal antigen to detect a fungal infection caused by yeast; detection of specific antibodies; CSF acid-fast bacilli (AFB) test to detect mycobacteria such as *Mycobacterium tuberculosis*; detection of parasites; and CSF syphilis test.

In some instances, diagnostic lumbar punctures are used to diagnose: bacterial, fungal, and viral infections including meningitis, encephalitis, and neurosyphilis or syphilis; bleeding around the brain or spinal cord including subarachnoid hemorrhages; inflammation of the brain, spinal cord, or bone marrow including myelitis; cancer including brain cancer, spinal cord cancer, and leukemia; neurological disorders including demyelinating diseases such as multiple sclerosis and demyelination polyneuropathy, Guillain-Barré syndrome, mitochondrial disorders, leukencephalopathies, paraneoplastic syndromes, Reye syndrome; headaches of unknown cause; and intracranial pressure disorders including pseudotumor cerebri also known as idiopathic intracranial hypertension (IIH), spontaneous intracranial hypotension, and normal pressure hydrocephalus.

Therapeutic Lumbar Puncture

Therapeutic lumbar punctures are performed in the same manner as diagnostic lumbar punctures however, instead of collecting a sample of CSF, a therapeutic agent is delivered to the subarachnoid space. In some embodiments, therapeutic agents delivered via a lumbar puncture include but are not limited to: anesthetics such as bupivacaine, lidocaine, tetracaine, procaine, ropivacaine, levobupivacaine, prilocaine, and cinchocaine; opioids such as morphine, fentanyl, diamorphine, buprenorphine, and pethidine or meperidine; non-opioids such as clonidine; chemotherapeutic agents such as methotrexate, cytarabine, hydrocortisone, and thiotepa; contrast agents or dyes such as iohexol, metrizamide, iopamidol, ioversol, iopromide, iodixanol, iolotran, and iodophenylundecylic acid; anti-spasmodic agents such as baclofen; antibiotics such as gentamicin sulphate; proteins such as idursulfase.

Tactile Sensing Device

Tactile Sensing Device: Device

Disclosed herein, in certain embodiments, are tactile sensing devices for imaging bone and non-bone structures in an individual in need thereof, comprising: a display screen 1032, 2032 to visualize an image of the bone and non-bone structures; and a needle guide 1002, 2002 operatively configured to guide a needle into a target tissue location within the individual, as shown in FIGS. 1A, 1B, 1C, 2A, 2B, and 2C. In some embodiments, the tactile sensing device 1000, 2000 images a first and second bone and non-bone structure.

Sensor Arrays

In some embodiments, the tactile sensing device 1000 comprises an array of sensors 1008. In some embodiments, the sensor array 1008 is a tactile sensor array. In some embodiments, the sensor array 1008 is an ultrasound sensor array. In some embodiments, the sensor array 1008 is an infrared radiation (IR) sensor array. In some embodiments, the sensor array 1008 comprises sensors that are piezoresistive sensors. In some embodiments, the sensor array 1008 comprises sensors are piezoelectric sensors. In some embodiments, the sensor array 1008 comprises sensors that are optical sensors. In some embodiments, the sensor array 1008 comprises sensors that are electromagnetic sensors. In some embodiments, the sensor array 1008 comprises sensors that are capacitive sensors. In some embodiments, the sensor array 1008 comprises sensors that are potentiometric sensors.

In some embodiments, the sensor array 1008 comprises pressure sensors. In some embodiments, the pressure sensors are force-sensitive resistors. Force-sensitive resistors change their resistance in response to a change in force applied to their surface. In some embodiments, the force-sensitive resistors decrease their resistance with an increase in force applied the surface of the sensor. In some embodiments, the sensor array comprises at least one sensor configured to output a signal in response to a change in force applied to its surface. Force-sensitive resistors are two wire devices with a resistance that depends on applied force. In some embodiments, the force-sensitive resistors comprise a voltage divider. In some embodiments, the voltage divider outputs a voltage value that is correlated to the resistance; thus, the output voltage value also changes in response to a force applied to the surface of the sensor. In some embodiments, an increase in voltage indicates an increase in a force applied to the surface of the sensor. In some instances, the force-sensitive resistors output voltage signals. In some embodiments, the array of force-sensitive resistors is a 6×3 array comprising eighteen force-sensitive resistors. In some embodiments, the array of force-sensitive resistors is an 8×4 array comprising thirty two force-sensitive resistors. In some embodiments, the size of the array of force-sensitive resistors is dependent upon the surface area of the individual's body to be examined. In some embodiments, the array of force-sensitive resistors is configured in a way that is sufficient to visualize the bone and non-bone structures in the individual.

Figure 3A:
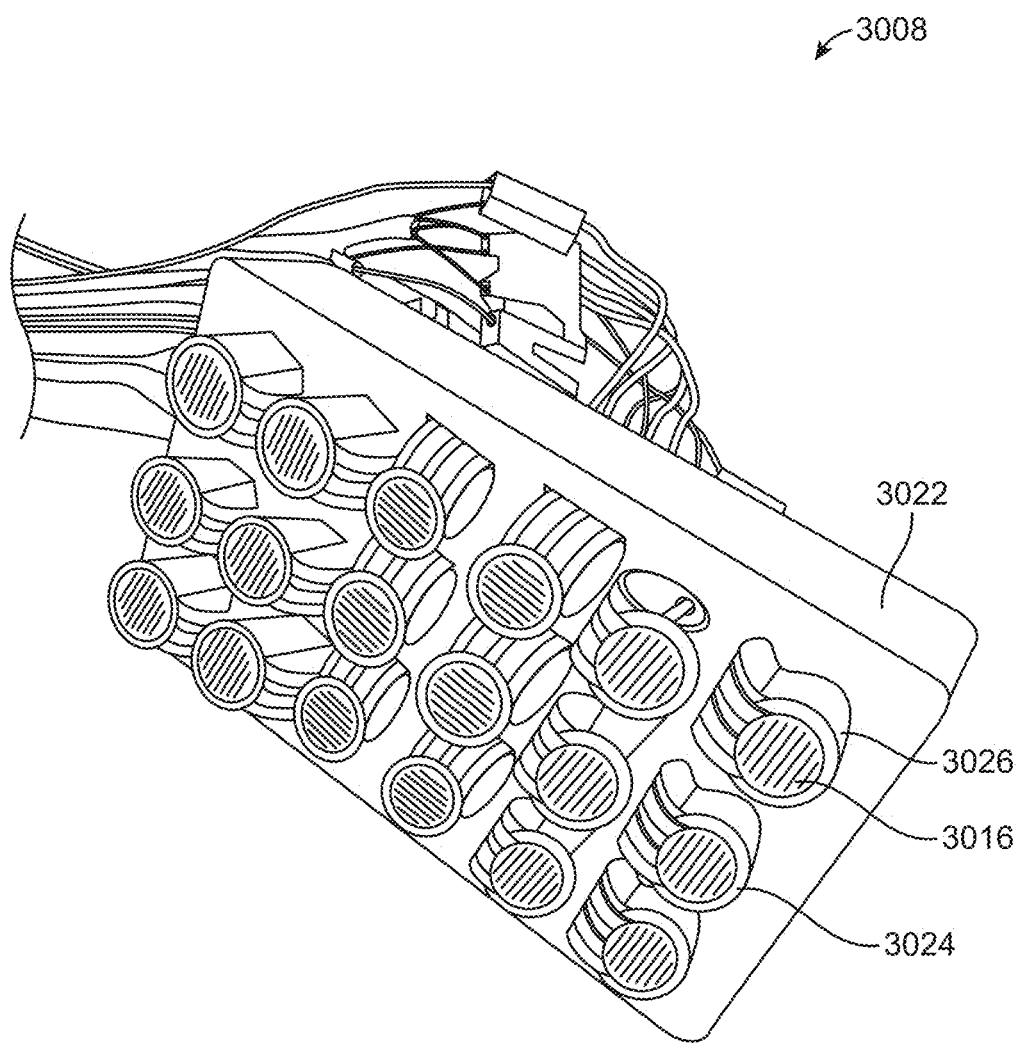
FIGS. 3A-B exemplify a sensor array 3008 of eighteen force-sensitive resistors with silicon disks adhered onto them to enhance force feedback.
Figure 3B:
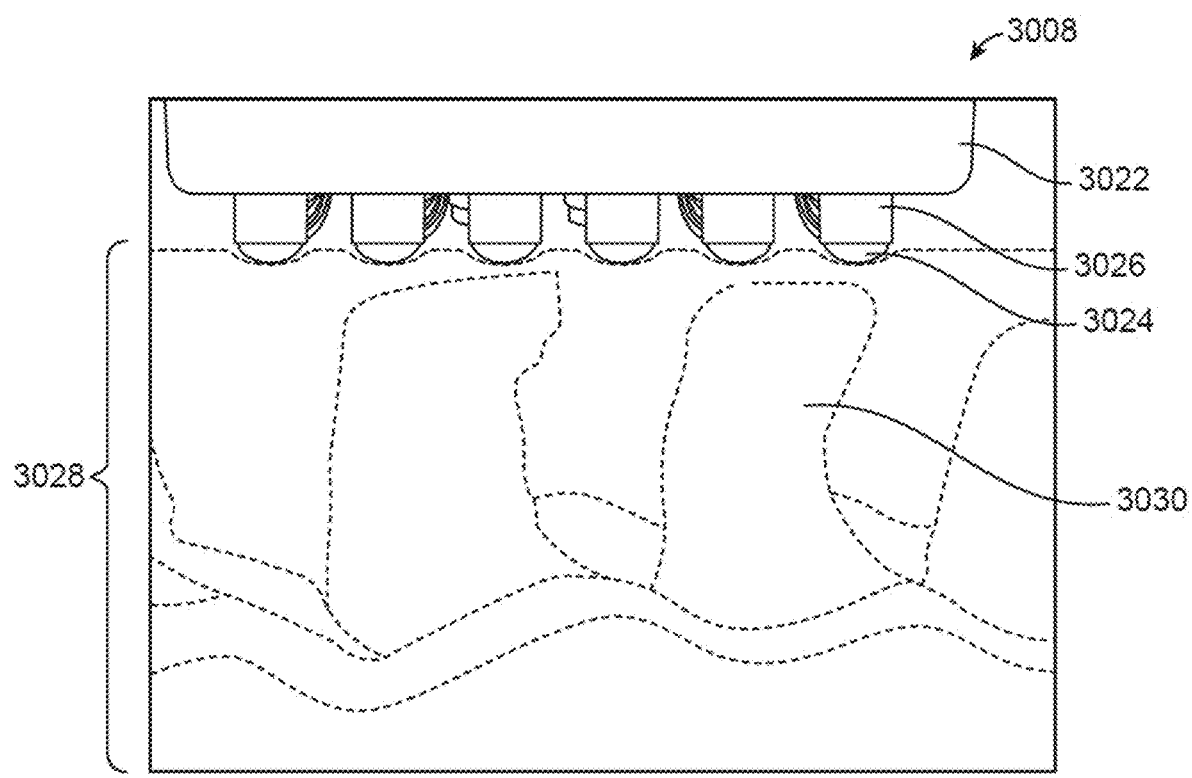

In some embodiments, as shown in FIGS. 3A and 3B, the sensor array 3008 is secured onto a sensor array platform 3022. In some embodiments, the sensor array platform 3022 comprises cylindrical struts 3026 onto which the sensors are adhered to. In some embodiments, the cylindrical struts 3026 onto which the sensors are adhered are connectors. In some embodiments, the cylindrical struts or connectors are not cylindrical, but rather rectangular or square shaped. In some embodiments, the cylindrical struts are spring loaded connectors. In some embodiments, the cylindrical struts 3026 are Pogo pins. In some embodiments, the Pogo pins establish a connection to a printed circuit board (PCT) or between pluralities of PCTs. Non-limiting types of Pogo pins include vertical mount surface mount technology (SMT), vertical type, through hole type, horizontal type, right angle type, cable solder type, or water proof connector type. In some embodiments, the sensor 3016 is covered with a hemispherical disk 3024 configured to enhance force feedback. In some embodiments, the hemispherical disk 3024 covering the force-sensitive resistors is a hemispherical rubber disk. In some embodiments, the rubber material includes, but is not limited to: silicone rubber, natural rubber, acrylonitrile-butadiene rubber, hydrogenated acrylonitrile-butadiene rubber, ethylene propylene diene rubber, fluorocarbon rubber, chloroprene rubber, fluoro silicone rubber, polyacrylate rubber, ethylene acrylic rubber, styrene-butadiene rubber, polyester urethane rubber, or polyether urethane rubber.

Bone and Non-Bone Structures

In some embodiments, the tactile sensing device images a target tissue location. In some embodiments, the desired target tissue location is the bone marrow. In some embodiments, the tactile sensing device images bone and non-bone structures around a target tissue location. In some embodiments, the tactile sensing device images the lumbar vertebrae and the non-bone structures surrounding the lumbar vertebrae. In some embodiments, the tactile sensing device images the sacral vertebrae and the non-bone structures surrounding the sacral vertebrae. In some embodiments, the tactile sensing device images the lumbar and sacral vertebrae and the non-bone structures surrounding the lumbar and sacral vertebrae. In some embodiments, the tactile sensing device images the spinous processes and the non-bone structures surrounding the spinous processes. In some embodiments, the tactile sensing device images the L3 and L4 spinous processes and the non-bone structures surrounding the L3 and L4 spinous processes. In some embodiments, the tactile sensing device images the L5 and L5 spinous processes and the non-bone structures surrounding the L4 and L5 spinous processes. In some embodiments, the tactile sensing device images the L5 and S1 spinous processes and the non-bone structures surrounding the L3 and L4 spinous processes.

In some embodiments, the tactile sensing device 1000, 2000 images a first and second bone and non-bone structures. In some embodiments, the tactile sensing device 1000, 2000 images a plurality of bone and non-bone structures. In some embodiments, a bone structure is a rib. In some embodiments, a bone structure is an articular surface. In some embodiments an articular surface is a vertebral articulation, an articulation of a first bone of a hand with a second bone of the hand, an elbow joint, a wrist joint, an axillary articulation of a first bone of a shoulder with a second bone of the shoulder, a sternoclavicular joint, a temporomandibular joint, a sacroiliac joint, a hip joint, a knee joint, or an articulations of a first bone of a foot with a second bone of the foot. In some instances, a vertebral articulation is a spinous process. In some embodiments, a non-bone structure is subcutaneous tissue, a muscle, a ligament, adipose tissue, a cyst, or a cavity.

Display Screen

As shown in FIGS. 1A, 1B, 1C, 2A, 2B, and 2C, in some embodiments, the tactile sensing device 1000, 2000 comprises a display screen 1032, 2032 to provide visual information to a user. In some embodiments, the display screen 1032, 2032 is operatively connected to the tactile sensing device 1000, 2000. In some embodiments, the display screen 1032, 2032 is a computer screen, a mobile device screen, or a portable device screen. In some embodiments, the display screen 1032, 2032 is a cathode ray tube (CRT). In some embodiments, the display screen 1032, 2032 is a liquid crystal display (LCD). In further embodiments, the display screen 1032, 2032 is a thin film transistor liquid crystal display (TFT-LCD). In some embodiments, the display screen 1032, 2032 is an organic light emitting diode (OLED) display. In various further embodiments, an OLED display is a passive-matrix OLED (PMOLED) or active-matrix OLED (AMOLED) display. In some embodiments, the display screen 1032, 2032 is a plasma display. In other embodiments, the display screen 1032, 2032 is a video projector. In still further embodiments, the display screen 1032, 2032 is a combination of devices such as those disclosed herein.

In some embodiments, the visual information provided to the user via a display screen 1032 is a pressure map representing bone and non-bone structures. In some embodiments, the pressure map is a heat map. In some embodiments, the sensor array comprises at least one sensor configured to output a signal in response to a change in force applied to its surface, wherein the signal is represented as a heat map. In some embodiments, the heat map is a graphical representation of voltage signals wherein the individual voltage output signals are represented as a plurality of colors, color hues, color saturations, graphical patterns, shading, geometrical figures, or any combination thereof. In some embodiments, high voltage output signals are represented in a red-based color and low voltage output signals are represented in blue-based color. In some embodiments, the pressure map is overlaid onto a second image. In some embodiments, the second image is a type of diagnostic image including, but not limited to: radiography image, magnetic resonance imaging (MRI) image, computed tomography (CT) image, nuclear medicine image, ultrasound image, photoacoustic image, or thermography image. In some embodiments, the second image is an image of bone and non-bone structures. In some embodiments, the second image of a bone and non-bone structure is an image of a rib; an articular surface such as, a vertebral articulation, an articulation of a first bone of a hand with a second bone of the hand, an elbow joint, a wrist joint, an axillary articulation of a first bone of a shoulder with a second bone of the shoulder, a sternoclavicular joint, a temporomandibular joint, a sacroiliac joint, a hip joint, a knee joint, or an articulations of a first bone of a foot with a second bone of the foot; non-bone structure is subcutaneous tissue, a muscle, a ligament, adipose tissue, a cyst, or a cavity.

Needle Guide

Figure 1B:
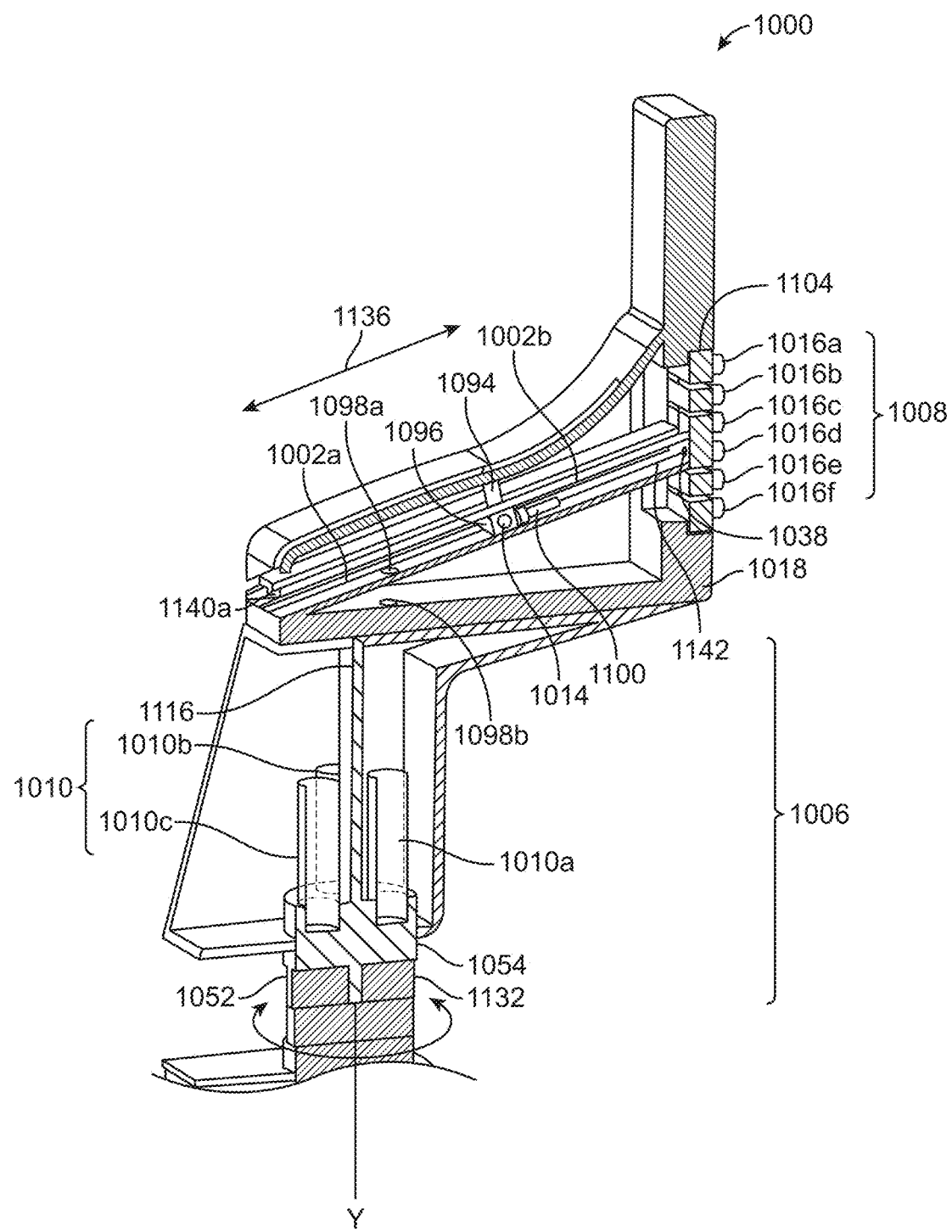
Figure 1C:
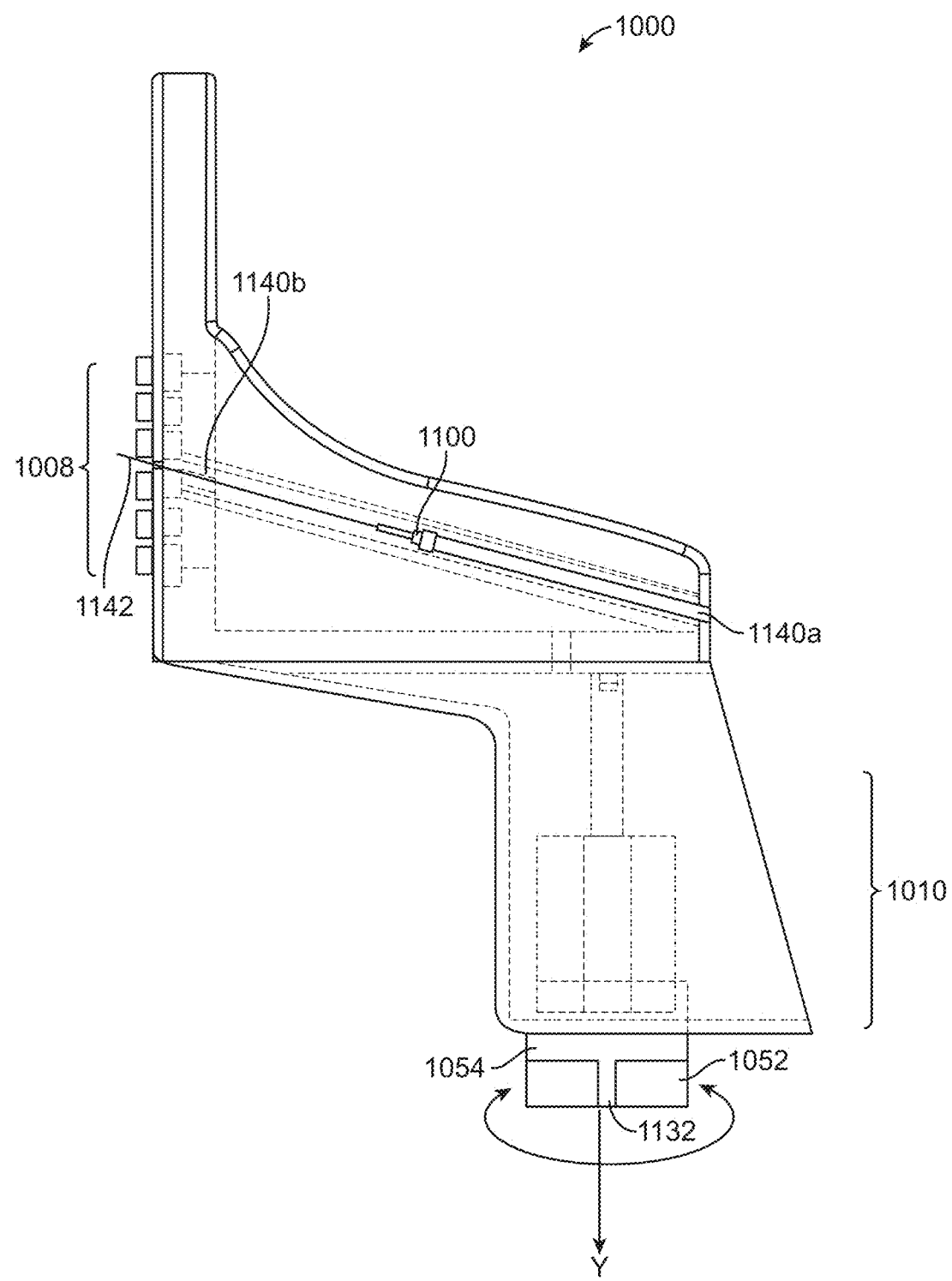

In some embodiments, as shown in FIGS. 1A, 1B, and 1C, a needle guide 1002 is operatively connected to the tactile sensing device 1000. In some embodiments, the needle guide 1002, operatively connected to the tactile sensing device 1000, is used to control the angle and direction of a needle that is inserted into an individual in need thereof. In some embodiments, the needle guide 1002 is oriented between a −45° and 45° cephalad angle, terminating at a needle orifice 1038 located on the center of the sensor array 1008, thereby controlling the angle at which the needle is inserted into a human body. In some embodiments, the needle guide 1002 is oriented between a −45° and 45° cephalad angle, wherein −45° is equivalent to 315°. In some embodiments, the needle guide allows for the needle to be inserted into an individual at a cephalad angle between about 10° and about 20°.

In some embodiments, the needle guide allows for the needle to be inserted into an individual at a cephalad angle between about 0° and about 30°. In some embodiments, the needle guide allows for the needle to be inserted into an individual at a cephalad angle between about 0° and about 50°.

In some embodiments, the needle guide 1002 is oriented between a 0° and 15° cephalad angle. In some embodiments, the needle guide 1002 is oriented between a 15° and 30° cephalad angle. In some embodiments, the needle guide 1002 is oriented between a 30° and 45° cephalad angle. In some embodiments, the needle guide 1002 is oriented between a 45° and 60° cephalad angle. In some embodiments, the needle guide 1002 is oriented between a 0° and −15° cephalad angle. In some embodiments, the needle guide 1002 is oriented between a −15° and −30° cephalad angle. In some embodiments, the needle guide 1002 is oriented between a −30° and −45° cephalad angle. In some embodiments, the needle guide 1002 is oriented between a −45° and −60° cephalad angle. In some embodiments, the needle guide 1002 is oriented at a 0° cephalad angle. In some embodiments, the needle guide 1002 is oriented at a 1° cephalad angle. In some embodiments, the needle guide 1002 is oriented at a 2° cephalad angle. In some embodiments, the needle guide 1002 is oriented at a 3° cephalad angle. In some embodiments, the needle guide 1002 is oriented at a 4° cephalad angle. In some embodiments, the needle guide 1002 is oriented at a 5° cephalad angle. In some embodiments, the needle guide 1002 is oriented at a 6° cephalad angle. In some embodiments, the needle guide 1002 is oriented at a 7° cephalad angle. In some embodiments, the needle guide 1002 is oriented at an 8° cephalad angle. In some embodiments, the needle guide 1002 is oriented at a 9° cephalad angle. In some embodiments, the needle guide 1002 is oriented at a 10° cephalad angle. In some embodiments, the needle guide 1002 is oriented at an 11° cephalad angle. In some embodiments, the needle guide 1002 is oriented at a 12° cephalad angle. In some embodiments, the needle guide 1002 is oriented at a 13° cephalad angle. In some embodiments, the needle guide 1002 is oriented at a 14° cephalad angle. In some embodiments, the needle guide 1002 is oriented at a 15° cephalad angle. In some embodiments, the needle guide 1002 is oriented at a 16° cephalad angle. In some embodiments, the needle guide 1002 is oriented at a 17° cephalad angle. In some embodiments, the needle guide 1002 is oriented at an 18° cephalad angle. In some embodiments, the needle guide 1002 is oriented at a 19° cephalad angle. In some embodiments, the needle guide 1002 is oriented at a 20° cephalad angle. In some embodiments, the needle guide 1002 is oriented at a 21° cephalad angle. In some embodiments, the needle guide 1002 is oriented at a 22° cephalad angle. In some embodiments, the needle guide 1002 is oriented at a 23° cephalad angle. In some embodiments, the needle guide 1002 is oriented at a 24° cephalad angle. In some embodiments, the needle guide 1002 is oriented at a 25° cephalad angle. In some embodiments, the needle guide 1002 is oriented at a 26° cephalad angle. In some embodiments, the needle guide 1002 is oriented at a 27° cephalad angle. In some embodiments, the needle guide 1002 is oriented at a 28° cephalad angle. In some embodiments, the needle guide 1002 is oriented at a 29° cephalad angle. In some embodiments, the needle guide 1002 is oriented at a 30° cephalad angle. In some embodiments, the needle guide 1002 is oriented at a 31° cephalad angle. In some embodiments, the needle guide 1002 is oriented at a 32° cephalad angle. In some embodiments, the needle guide 1002 is oriented at a 33° cephalad angle. In some embodiments, the needle guide 1002 is oriented at a 34° cephalad angle. In some embodiments, the needle guide 1002 is oriented at a 35° cephalad angle. In some embodiments, the needle guide 1002 is oriented at a 36° cephalad angle. In some embodiments, the needle guide 1002 is oriented at a 37° cephalad angle. In some embodiments, the needle guide 1002 is oriented at a 38° cephalad angle. In some embodiments, the needle guide 1002 is oriented at a 39° cephalad angle. In some embodiments, the needle guide 1002 is oriented at a 40° cephalad angle. In some embodiments, the needle guide 1002 is oriented at a 41° cephalad angle. In some embodiments, the needle guide 1002 is oriented at a 42° cephalad angle. In some embodiments, the needle guide 1002 is oriented at a 43° cephalad angle. In some embodiments, the needle guide 1002 is oriented at a 44° cephalad angle. In some embodiments, the needle guide 1002 is oriented at a 45° cephalad angle. In some embodiments, the needle guide 1002 is oriented at a 46° cephalad angle. In some embodiments, the needle guide 1002 is oriented at a 47° cephalad angle. In some embodiments, the needle guide 1002 is oriented at a 48° cephalad angle. In some embodiments, the needle guide 1002 is oriented at a 49° cephalad angle. In some embodiments, the needle guide 1002 is oriented at a 50° cephalad angle. In some embodiments, the needle guide 1002 is oriented at a 51° cephalad angle. In some embodiments, the needle guide 1002 is oriented at a 52° cephalad angle. In some embodiments, the needle guide 1002 is oriented at a 53° cephalad angle. In some embodiments, the needle guide 1002 is oriented at a 54° cephalad angle. In some embodiments, the needle guide 1002 is oriented at a 55° cephalad angle. In some embodiments, the needle guide 1002 is oriented at a 56° cephalad angle. In some embodiments, the needle guide 1002 is oriented at a 57° cephalad angle. In some embodiments, the needle guide 1002 is oriented at a 58° cephalad angle. In some embodiments, the needle guide 1002 is oriented at a 59° cephalad angle. In some embodiments, the needle guide 1002 is oriented at a 60° cephalad angle. In some embodiments, the needle guide 1002 is oriented at a 315° cephalad angle. In some embodiments, the needle guide 1002 is oriented at a 316° cephalad angle. In some embodiments, the needle guide 1002 is oriented at a 317° cephalad angle. In some embodiments, the needle guide 1002 is oriented at a 318° cephalad angle. In some embodiments, the needle guide 1002 is oriented at a 319° cephalad angle. In some embodiments, the needle guide 1002 is oriented at a 320° cephalad angle. In some embodiments, the needle guide 1002 is oriented at a 321° cephalad angle. In some embodiments, the needle guide 1002 is oriented at a 322° cephalad angle. In some embodiments, the needle guide 1002 is oriented at a 323° cephalad angle. In some embodiments, the needle guide 1002 is oriented at a 324° cephalad angle. In some embodiments, the needle guide 1002 is oriented at a 325° cephalad angle. In some embodiments, the needle guide 1002 is oriented at a 326° cephalad angle. In some embodiments, the needle guide 1002 is oriented at a 327° cephalad angle. In some embodiments, the needle guide 1002 is oriented at a 328° cephalad angle. In some embodiments, the needle guide 1002 is oriented at a 329° cephalad angle. In some embodiments, the needle guide 1002 is oriented at a 330° cephalad angle. In some embodiments, the needle guide 1002 is oriented at a 331° cephalad angle. In some embodiments, the needle guide 1002 is oriented at a 332° cephalad angle. In some embodiments, the needle guide 1002 is oriented at a 333° cephalad angle. In some embodiments, the needle guide 1002 is oriented at a 334° cephalad angle. In some embodiments, the needle guide 1002 is oriented at a 335° cephalad angle. In some embodiments, the needle guide 1002 is oriented at a 336° cephalad angle. In some embodiments, the needle guide 1002 is oriented at a 337° cephalad angle. In some embodiments, the needle guide 1002 is oriented at a 338° cephalad angle. In some embodiments, the needle guide 1002 is oriented at a 339° cephalad angle. In some embodiments, the needle guide 1002 is oriented at a 340° cephalad angle. In some embodiments, the needle guide 1002 is oriented at a 341° cephalad angle. In some embodiments, the needle guide 1002 is oriented at a 342° cephalad angle. In some embodiments, the needle guide 1002 is oriented at a 343° cephalad angle. In some embodiments, the needle guide 1002 is oriented at a 344° cephalad angle. In some embodiments, the needle guide 1002 is oriented at a 345° cephalad angle. In some embodiments, the needle guide 1002 is oriented at a 346° cephalad angle. In some embodiments, the needle guide 1002 is oriented at a 347° cephalad angle. In some embodiments, the needle guide 1002 is oriented at a 348° cephalad angle. In some embodiments, the needle guide 1002 is oriented at a 349° cephalad angle. In some embodiments, the needle guide 1002 is oriented at a 350° cephalad angle. In some embodiments, the needle guide 1002 is oriented at a 351° cephalad angle. In some embodiments, the needle guide 1002 is oriented at a 352° cephalad angle. In some embodiments, the needle guide 1002 is oriented at a 353° cephalad angle. In some embodiments, the needle guide 1002 is oriented at a 354° cephalad angle. In some embodiments, the needle guide 1002 is oriented at a 355° cephalad angle. In some embodiments, the needle guide 1002 is oriented at a 356° cephalad angle. In some embodiments, the needle guide 1002 is oriented at a 357° cephalad angle. In some embodiments, the needle guide 1002 is oriented at a 358° cephalad angle. In some embodiments, the needle guide 1002 is oriented at a 359° cephalad angle. In some embodiments, the needle guide 1002 is oriented at a 360° cephalad angle. In some embodiments, the needle orifice 1038 located on the center of the sensor array 1008 is an elongated slit. In some embodiments, the needle guide 1002 terminates at a plurality of openings formed by an elongated slit with a plurality of columns.

Figure 2A:
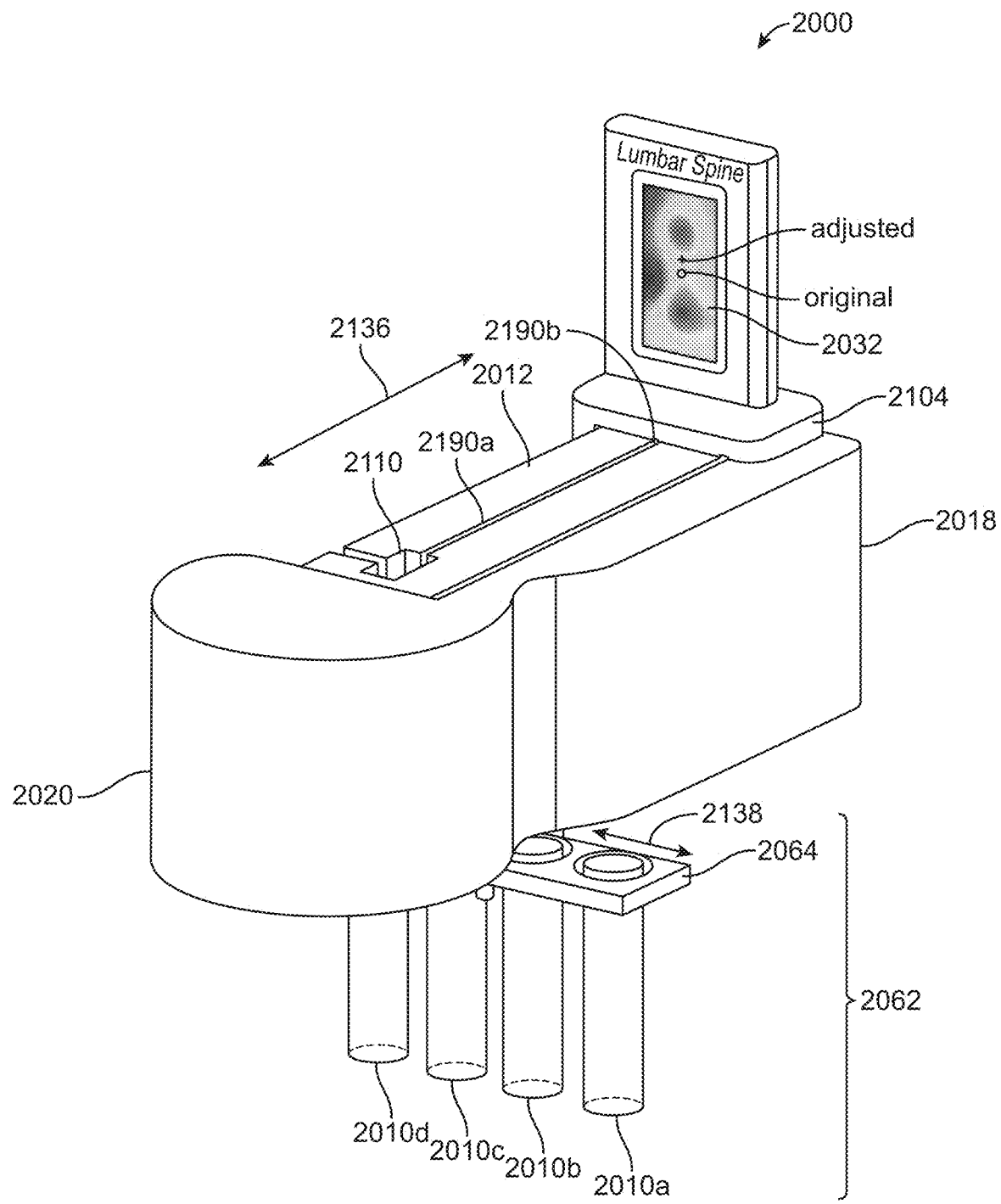
FIGS. 2A-C illustrate another embodiment of a tactile sensing device 2000 comprising multiple needle guides and a gripper 2004.
Figure 2B:
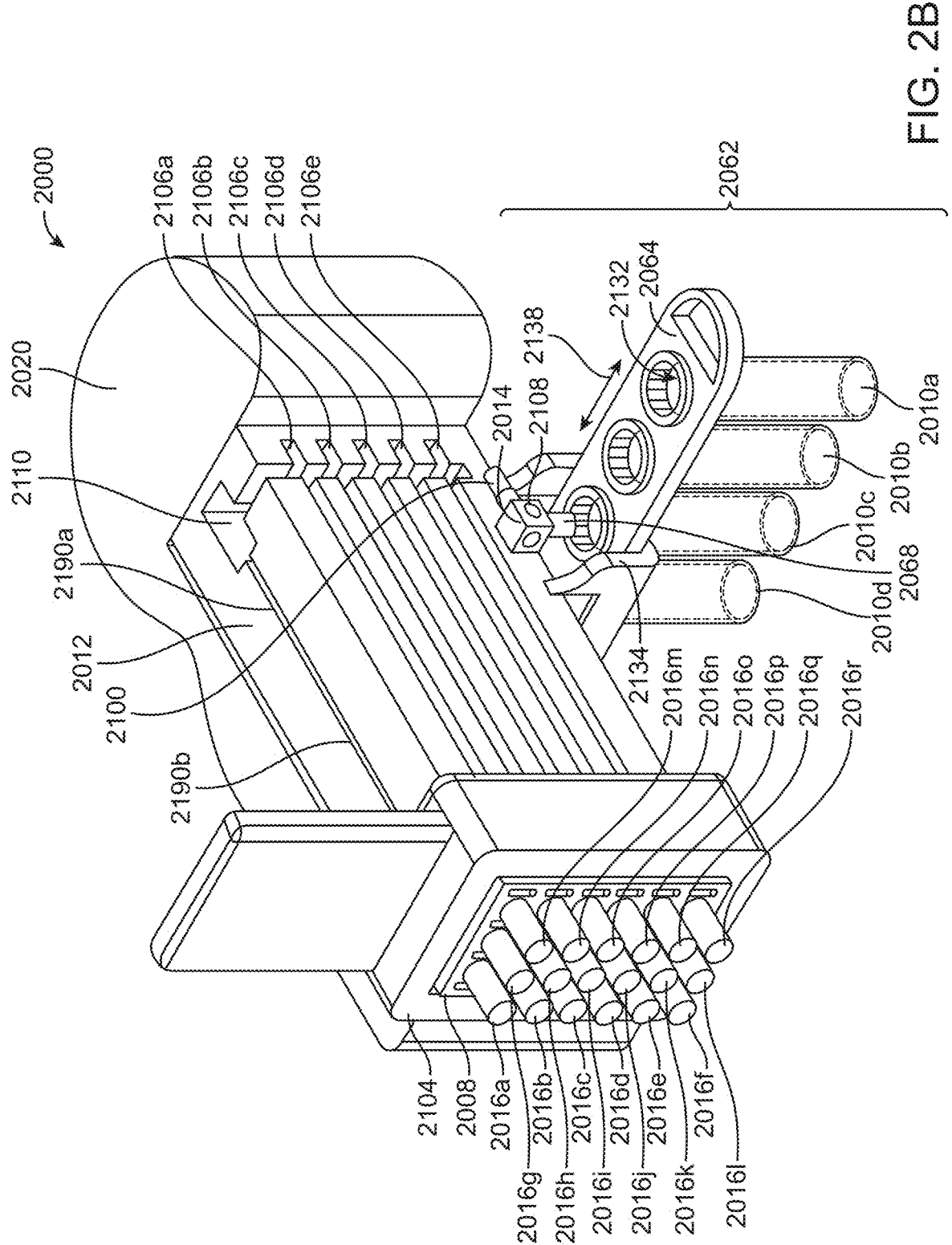
Figure 2C:
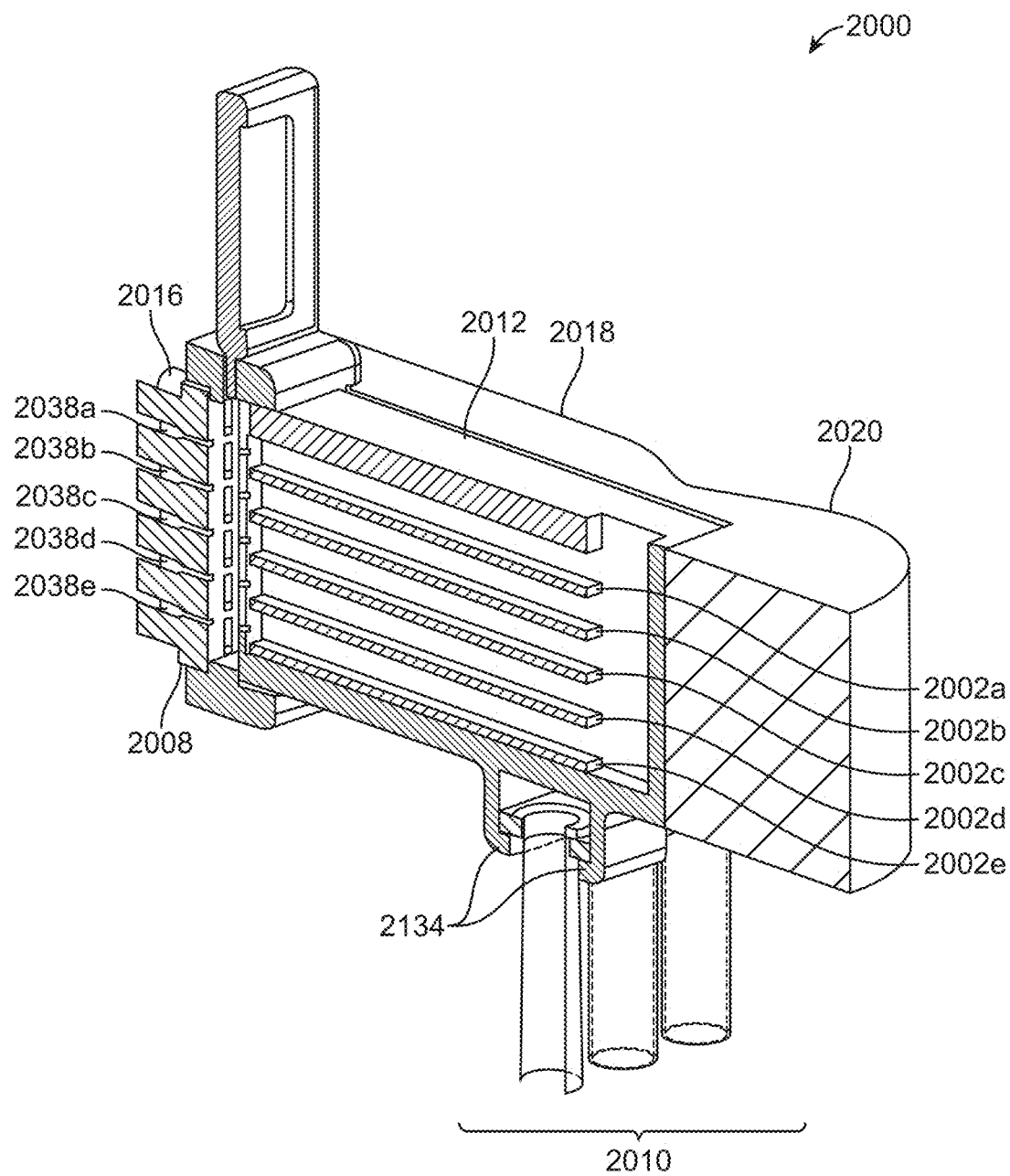

In various further embodiments, as shown in FIGS. 2A, 2B, and 2C, a needle guide cartridge 2012 is operatively connected to the tactile sensing device 2000. In some embodiments, the needle guide cartridge 2012 is oriented between a −45° and 45° cephalad angle, terminating at a needle orifice 2038 located along the midline of the sensor array 2008, thereby controlling the angle at which the needle is inserted into a human body. In some embodiments, the needle guide cartridge 2012 is oriented between a −45° and 45° cephalad angle, wherein −45° is equivalent to 315°. In some embodiments, the needle guide cartridge 2012 is oriented between a 0° and 15° cephalad angle. In some embodiments, the needle guide cartridge 2012 is oriented between a 15° and 30° cephalad angle. In some embodiments, the needle guide cartridge 2012 is oriented between a 30° and 45° cephalad angle. In some embodiments, the needle guide cartridge 2012 is oriented between a 45° and 60° cephalad angle. In some embodiments, the needle guide cartridge 2012 is oriented between a 0° and −15° cephalad angle. In some embodiments, the needle guide cartridge 2012 is oriented between a −15° and −30° cephalad angle. In some embodiments, the needle guide cartridge 2012 is oriented between a −30° and −45° cephalad angle. In some embodiments, the needle guide cartridge 2012 is oriented between a −45° and −60° cephalad angle. In some embodiments, the needle guide cartridge 2012 is oriented at a 0° cephalad angle. In some embodiments, the needle guide cartridge 2012 is oriented at a 1° cephalad angle. In some embodiments, the needle guide cartridge 2012 is oriented at a 2° cephalad angle. In some embodiments, the needle guide cartridge 2012 is oriented at a 3° cephalad angle. In some embodiments, the needle guide cartridge 2012 is oriented at a 4° cephalad angle. In some embodiments, the needle guide cartridge 2012 is oriented at a 5° cephalad angle. In some embodiments, the needle guide cartridge 2012 is oriented at a 6° cephalad angle. In some embodiments, the needle guide cartridge 2012 is oriented at a 7° cephalad angle. In some embodiments, the needle guide cartridge 2012 is oriented at an 8° cephalad angle. In some embodiments, the needle guide cartridge 2012 is oriented at a 9° cephalad angle. In some embodiments, the needle guide cartridge 2012 is oriented at a 10° cephalad angle. In some embodiments, the needle guide cartridge 2012 is oriented at an 11° cephalad angle. In some embodiments, the needle guide cartridge 2012 is oriented at a 12° cephalad angle. In some embodiments, the needle guide cartridge 2012 is oriented at a 13° cephalad angle. In some embodiments, the needle guide cartridge 2012 is oriented at a 14° cephalad angle. In some embodiments, the needle guide cartridge 2012 is oriented at a 15° cephalad angle. In some embodiments, the needle guide cartridge 2012 is oriented at a 16° cephalad angle. In some embodiments, the needle guide cartridge 2012 is oriented at a 17° cephalad angle. In some embodiments, the needle guide cartridge 2012 is oriented at an 18° cephalad angle. In some embodiments, the needle guide cartridge 2012 is oriented at a 19° cephalad angle. In some embodiments, the needle guide cartridge 2012 is oriented at a 20° cephalad angle. In some embodiments, the needle guide cartridge 2012 is oriented at a 21° cephalad angle. In some embodiments, the needle guide cartridge 2012 is oriented at a 22° cephalad angle. In some embodiments, the needle guide cartridge 2012 is oriented at a 23° cephalad angle. In some embodiments, the needle guide cartridge 2012 is oriented at a 24° cephalad angle. In some embodiments, the needle guide cartridge 2012 is oriented at a 25° cephalad angle. In some embodiments, the needle guide cartridge 2012 is oriented at a 26° cephalad angle. In some embodiments, the needle guide cartridge 2012 is oriented at a 27° cephalad angle. In some embodiments, the needle guide cartridge 2012 is oriented at a 28° cephalad angle. In some embodiments, the needle guide cartridge 2012 is oriented at a 29° cephalad angle. In some embodiments, the needle guide cartridge 2012 is oriented at a 30° cephalad angle. In some embodiments, the needle guide cartridge 2012 is oriented at a 31° cephalad angle. In some embodiments, the needle guide cartridge 2012 is oriented at a 32° cephalad angle. In some embodiments, the needle guide cartridge 2012 is oriented at a 33° cephalad angle. In some embodiments, the needle guide cartridge 2012 is oriented at a 34° cephalad angle. In some embodiments, the needle guide cartridge 2012 is oriented at a 35° cephalad angle. In some embodiments, the needle guide cartridge 2012 is oriented at a 36° cephalad angle. In some embodiments, the needle guide cartridge 2012 is oriented at a 37° cephalad angle. In some embodiments, the needle guide cartridge 2012 is oriented at a 38° cephalad angle. In some embodiments, the needle guide cartridge 2012 is oriented at a 39° cephalad angle. In some embodiments, the needle guide cartridge 2012 is oriented at a 40° cephalad angle. In some embodiments, the needle guide cartridge 2012 is oriented at a 41° cephalad angle. In some embodiments, the needle guide cartridge 2012 is oriented at a 42° cephalad angle. In some embodiments, the needle guide cartridge 2012 is oriented at a 43° cephalad angle. In some embodiments, the needle guide cartridge 2012 is oriented at a 44° cephalad angle. In some embodiments, the needle guide cartridge 2012 is oriented at a 45° cephalad angle. In some embodiments, the needle guide cartridge 2012 is oriented at a 46° cephalad angle. In some embodiments, the needle guide cartridge 2012 is oriented at a 47° cephalad angle. In some embodiments, the needle guide cartridge 2012 is oriented at a 48° cephalad angle. In some embodiments, the needle guide cartridge 2012 is oriented at a 49° cephalad angle. In some embodiments, the needle guide cartridge 2012 is oriented at a 50° cephalad angle. In some embodiments, the needle guide cartridge 2012 is oriented at a 51° cephalad angle. In some embodiments, the needle guide cartridge 2012 is oriented at a 52° cephalad angle. In some embodiments, the needle guide cartridge 2012 is oriented at a 53° cephalad angle. In some embodiments, the needle guide cartridge 2012 is oriented at a 54° cephalad angle. In some embodiments, the needle guide cartridge 2012 is oriented at a 55° cephalad angle. In some embodiments, the needle guide cartridge 2012 is oriented at a 56° cephalad angle. In some embodiments, the needle guide cartridge 2012 is oriented at a 57° cephalad angle. In some embodiments, the needle guide cartridge 2012 is oriented at a 58° cephalad angle. In some embodiments, the needle guide cartridge 2012 is oriented at a 59° cephalad angle. In some embodiments, the needle guide cartridge 2012 is oriented at a 60° cephalad angle. In some embodiments, the needle guide cartridge 2012 is oriented at a 315° cephalad angle. In some embodiments, the needle guide cartridge 2012 is oriented at a 316° cephalad angle. In some embodiments, the needle guide cartridge 2012 is oriented at a 317° cephalad angle. In some embodiments, the needle guide cartridge 2012 is oriented at a 318° cephalad angle. In some embodiments, the needle guide cartridge 2012 is oriented at a 319° cephalad angle. In some embodiments, the needle guide cartridge 2012 is oriented at a 320° cephalad angle. In some embodiments, the needle guide cartridge 2012 is oriented at a 321° cephalad angle. In some embodiments, the needle guide cartridge 2012 is oriented at a 322° cephalad angle. In some embodiments, the needle guide cartridge 2012 is oriented at a 323° cephalad angle. In some embodiments, the needle guide cartridge 2012 is oriented at a 324° cephalad angle. In some embodiments, the needle guide cartridge 2012 is oriented at a 325° cephalad angle. In some embodiments, the needle guide cartridge 2012 is oriented at a 326° cephalad angle. In some embodiments, the needle guide cartridge 2012 is oriented at a 327° cephalad angle. In some embodiments, the needle guide cartridge 2012 is oriented at a 328° cephalad angle. In some embodiments, the needle guide cartridge 2012 is oriented at a 329° cephalad angle. In some embodiments, the needle guide cartridge 2012 is oriented at a 330° cephalad angle. In some embodiments, the needle guide cartridge 2012 is oriented at a 331° cephalad angle. In some embodiments, the needle guide cartridge 2012 is oriented at a 332° cephalad angle. In some embodiments, the needle guide cartridge 2012 is oriented at a 333° cephalad angle. In some embodiments, the needle guide cartridge 2012 is oriented at a 334° cephalad angle. In some embodiments, the needle guide cartridge 2012 is oriented at a 335° cephalad angle. In some embodiments, the needle guide cartridge 2012 is oriented at a 336° cephalad angle. In some embodiments, the needle guide cartridge 2012 is oriented at a 337° cephalad angle. In some embodiments, the needle guide cartridge 2012 is oriented at a 338° cephalad angle. In some embodiments, the needle guide cartridge 2012 is oriented at a 339° cephalad angle. In some embodiments, the needle guide cartridge 2012 is oriented at a 340° cephalad angle. In some embodiments, the needle guide cartridge 2012 is oriented at a 341° cephalad angle. In some embodiments, the needle guide cartridge 2012 is oriented at a 342° cephalad angle. In some embodiments, the needle guide cartridge 2012 is oriented at a 343° cephalad angle. In some embodiments, the needle guide cartridge 2012 is oriented at a 344° cephalad angle. In some embodiments, the needle guide cartridge 2012 is oriented at a 345° cephalad angle. In some embodiments, the needle guide cartridge 2012 is oriented at a 346° cephalad angle. In some embodiments, the needle guide cartridge 2012 is oriented at a 347° cephalad angle. In some embodiments, the needle guide cartridge 2012 is oriented at a 348° cephalad angle. In some embodiments, the needle guide cartridge 2012 is oriented at a 349° cephalad angle. In some embodiments, the needle guide cartridge 2012 is oriented at a 350° cephalad angle. In some embodiments, the needle guide cartridge 2012 is oriented at a 351° cephalad angle. In some embodiments, the needle guide cartridge 2012 is oriented at a 352° cephalad angle. In some embodiments, the needle guide cartridge 2012 is oriented at a 353° cephalad angle. In some embodiments, the needle guide cartridge 2012 is oriented at a 354° cephalad angle. In some embodiments, the needle guide cartridge 2012 is oriented at a 355° cephalad angle. In some embodiments, the needle guide cartridge 2012 is oriented at a 356° cephalad angle. In some embodiments, the needle guide cartridge 2012 is oriented at a 357° cephalad angle. In some embodiments, the needle guide cartridge 2012 is oriented at a 358° cephalad angle. In some embodiments, the needle guide cartridge 2012 is oriented at a 359° cephalad angle. In some embodiments, the needle guide cartridge 2012 is oriented at a 360° cephalad angle. In some embodiments, the needle guide cartridge 2012 terminates at an opening. In some embodiments, the needle guide cartridge 2012 terminates at an opening. In some embodiments, the needle orifice 2038 located on the center of the sensor array 2008 is an elongated slit.

Multiplexer

In some embodiments, the tactile sensing device 1000, 2000 further comprises a multiplexer. The multiplexer selects voltage output signals from the sensor 3016 and forwards the selected voltage output signals into a single line. In some embodiments, the multiplexer is an analog multiplexer. In some embodiments, the analog multiplexer is a 16:1 or an 8:1 multiplexer. In some embodiments, the analog multiplexer is a frequency division multiplexer or a wave division multiplexer. In various further embodiments, the multiplexer is a digital multiplexer. In some instances, the digital multiplexer is a time division multiplexer. In some embodiments, the time division multiplexer is a synchronous time division multiplexer or an asynchronous time division multiplexer. In some embodiments, the multiplexer is mounted onto a printed circuit board.

Voltage Divider

In some embodiments, the tactile sensing device further comprises a voltage divider. In some embodiments, the voltage divider is a component of a force-sensitive resistor. In some embodiments, the force-sensitive resistor is coupled to a measuring resistor $R_M$ in a voltage divider. In some embodiments, the output voltage signal from the force-sensitive resistors is read out using a voltage divider. In some embodiments, the output voltage signal read out using the voltage divider is described by Equation 1 below.

$$V_{OUT}=(R_M V_{IN})/(R_M+R_{FSR});\qquad\text{Equation 1:}$$

wherein $V_{OUT}$ is the output voltage signal, $R_M$ is the measuring resistor, $V_{IN}$ is the input voltage signal, and $R_{FSR}$ is the resistance detected by the force-sensitive resistor.

In some embodiments, the voltage divider is a resistive voltage divider, a low-pass RC filter voltage divider, an inductive voltage divider, or a capacitive voltage divider.

Computing Device

In some embodiments, the tactile sensing device 1000, 2000 further comprises a computing device. In some embodiments, the computing device is a microcontroller. In some embodiments, the microcontroller is an 8-bit, 16-bit, or 32-bit microcontroller. In some embodiments, the microcontroller is an 8051 microcontroller, a programmable interface controller (PIC), an AVR or Advanced Virtual RISC microcontroller, or an ARM® microcontroller. In some embodiments, the microcontroller is, by way of non-limiting examples, an Arduino Uno microcontroller or a Raspberry Pi microcontroller.

In some embodiments, the computing device is a desktop computer or a laptop computer. In some embodiments, the computing device is a mobile device. In some embodiments, the mobile device is a smart phone or a smart watch. In some embodiments, the computing device is a portable device. In accordance with the description herein, suitable computing devices further include, by way of non-limiting examples, notebook computers, tablet computers, netbook computers, smart book computers, subnotebook computers, ultra-mobile PCs, handheld computers, personal digital assistants, Internet appliances, smart phones, music players, and portable video game systems. Many mobile smart phones are suitable for use in the systems described herein. Suitable tablet computers include those with booklet, slate, and convertible configurations. Suitable portable video game systems include, by way of non-limiting examples, Nintendo DS™ and Sony® PSP™.

Voltage Source

In some embodiments, the tactile sensing device 1000, 2000 further comprises a voltage source. In some embodiments, the voltage source is a battery. In some embodiments, the voltage source is rechargeable. In some embodiments, the voltage source is removable. In some embodiments, the voltage source includes, but is not limited to: a nickel cadmium (NiCd) battery, nickel-metal hydride (NiMH) battery, a nickel zinc (NiZn) battery, a lead acid battery, a lithium ion battery (Li-ion), or a lithium ion polymer (Li-ion polymer) battery.

Pressure Sensor

A critical component of a lumbar puncture is the recording of intracranial (ICP) pressure, represented by the ultralow pressure of the cerebrospinal fluid. ICP or cerebrospinal fluid pressure is typically in the 8-15 mmHg (10-20 mbar) range. Cerebrospinal fluid pressure is typically determined using a two-piece manometer attached to a 3-way stopcock valve which is connected to a spinal needle.

In some embodiments, the tactile sensing device 1000, 2000 further comprises a pressure sensor operatively connected to the tactile sensing device 1000, 2000 and configured to measure cerebrospinal fluid pressure. In some embodiments, the pressure sensor is operatively connected to the tactile sensing device 2000 via a 3-way valve 2014. In some embodiments, the pressure sensor is an electronic pressure sensor. In some instances, the pressure sensor is a piezoresistive, capacitive, electromagnetic, piezoelectric, optical, or potentiometric pressure sensor. In some embodiments, cerebrospinal fluid pressure measured with the electronic pressure sensor is displayed digitally. In some embodiments, cerebrospinal fluid pressure measured with the electronic pressure sensor is displayed on a display screen 1032 in real-time.

In some embodiments, the electronic pressure sensor is a Honeywell TruStability®, board mount pressure sensor, which is capable of sensing 0-60 mbar. In some embodiments, the electronic pressure sensor is an uncompensated and unamplified piezoresistive silicon pressure sensor. In some embodiments, the electronic pressure sensor is operatively connected to a barbed port. In some embodiments, the barbed port is liquid-compatible and replaces a traditional manometer connected to a 3-way stopcock valve.

Fluid Collection Systems

In some embodiments, the tactile sensing device further comprises a fluid collection system configured to collect a fluid such as cerebrospinal fluid. In some embodiments, the fluid collection system is disposable. In some embodiments, the fluid collection system is a diaphragm fluid collection system 5042. In some embodiments, the fluid collection system is a faucet fluid collection system 1006. In some embodiments, the fluid collection system is a top faucet fluid collection system 6120. In some embodiments, the fluid collection system is a spoke fluid collection system 7058. In some embodiments, the fluid collection system is a rail fluid collection system 8062.

Figure 5:
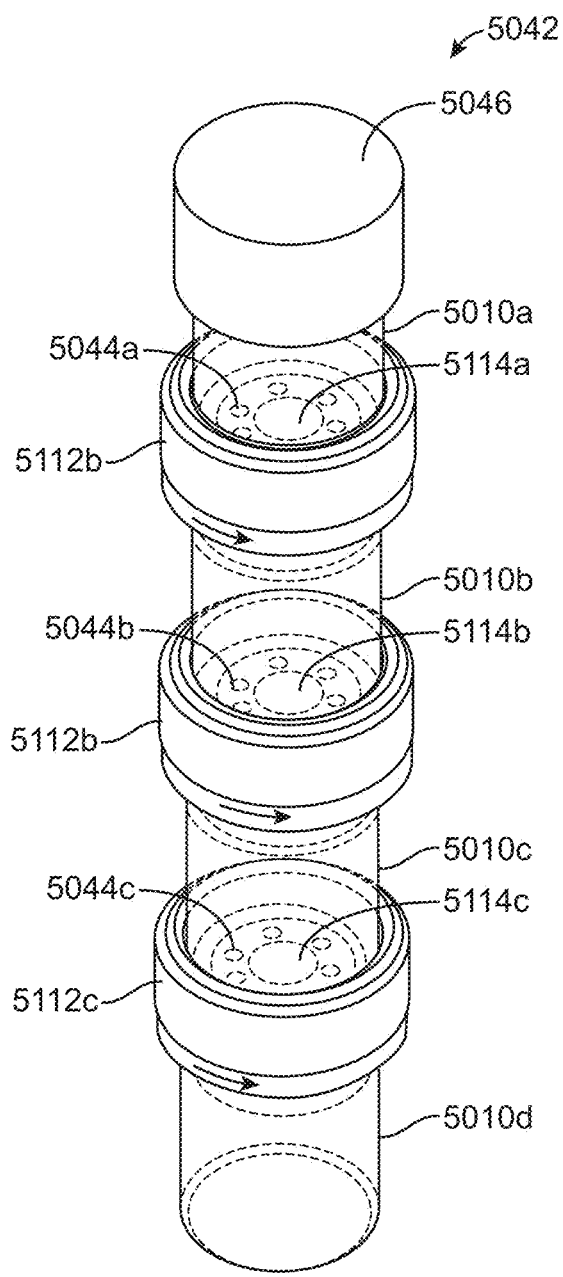
FIG. 5 illustrates a diaphragm fluid collection system of the tactile sensing device.

In some embodiments, tactile sensing device 1000, 2000 comprises a diaphragm fluid collection system 5042, as shown in FIG. 5. In some embodiments, the diaphragm fluid collection system 5042 comprises a set of stackable collection tubes 5010. The first collection tube 5010*a*, the second collection tube 5010*b*, the third collection tube 5010*c*, and the fourth collection tube 5010*d* comprises a first diaphragm 5044*a*, a second diaphragm 5044*b*, and a third diaphragm 5044*c*. To collect a fluid with the diaphragm fluid collection system 5042, a cap 5046 is first threaded off the first collection tube 5010*a*. The stackable collection tubes 5010 are placed under a needle hub, a 3-way valve, or tubing connected to a 3-way valve, with the first diaphragm 5044*a*, the second diaphragm 5044*b*, and the third diaphragm 5044*c* in the open position. Once sufficient fluid is collected in the fourth collection tube 5010*d*, the third diaphragm 5044*c* is closed and the third collection tube 5010*c*, the second collection tube 5010*b*, and the first collection tube 5010*a* are subsequently filled in the same manner.

Figure 6:
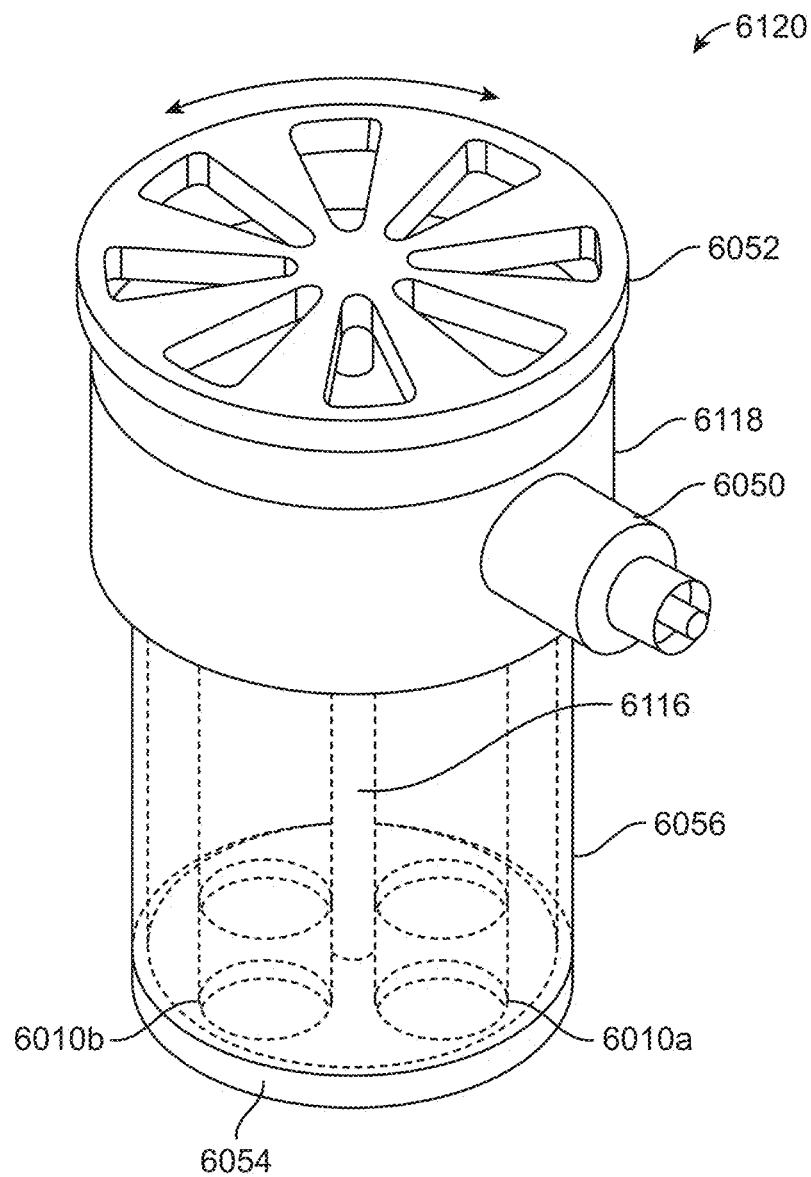
FIG. 6 illustrates a top faucet fluid collection system of the tactile sensing device.

In some embodiments, the fluid collection system operatively connected to the tactile sensing tactile sensing device comprises a top faucet fluid collection system 6120, as shown in FIG. 6. In some embodiments, the top faucet fluid collection system 6120 further comprises a container 6056 into which open collection tubes 6010 are placed. Additionally, the top faucet fluid collection system 6120 further comprises a rotating handle 6052 attached to a faucet base 6054 to which the collection tubes 6010 (1010, as shown in FIG. 1) are connected to. Above the collection tubes 6010, is a plate with a single hole (not shown in FIG. 6) located beneath a faucet connector 6050, which connects directly to a needle hub or a 3-way valve 2014. Once a first collection tube 6010*a* is sufficiently filled with fluid, the rotating handle 6052 is rotated clockwise or counterclockwise to allow for filling of the second collection tube 6010*b*, and the process repeats until all collection tubes 6010 are filled with fluid.

Figure 7:
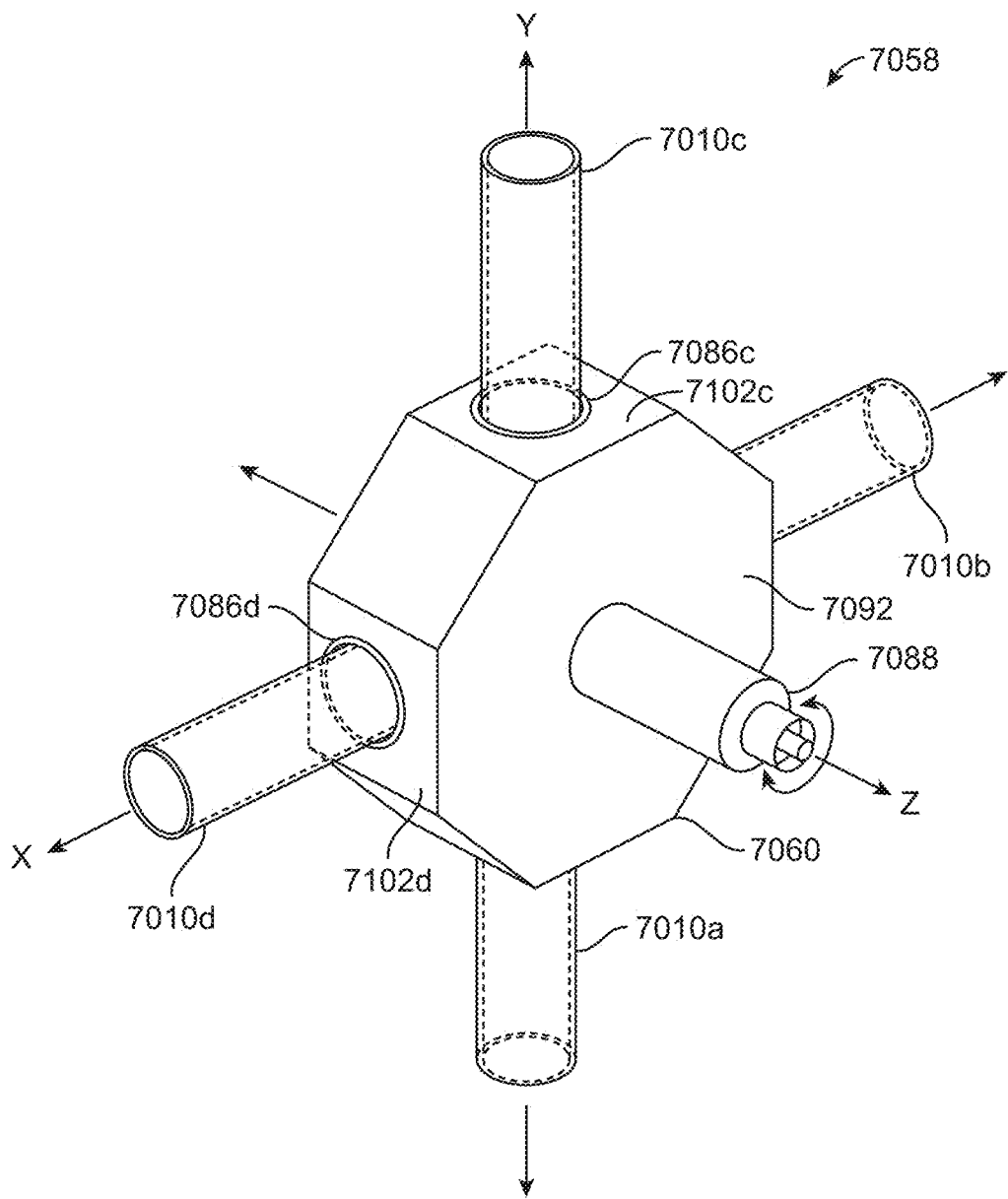
FIG. 7 illustrates a spoke fluid collection system of the tactile sensing device.

In some embodiments, the tactile sensing device comprises a spoke fluid collection system 7058, as shown in FIG. 7. In some embodiments, the spoke fluid collection system 7058 comprises a central hub 7060 with four central hub openings 7086. In some embodiments, the collection tubes 7010 are operatively connected to the central hub 7060. In some embodiments, the collection tubes 7010 are threaded into the central hub openings 7086. In some embodiments, the collection tubes 7010 are snapped into the central hub openings 7086. In some embodiments, the collection tubes 7010 are operatively connected to the central hub openings 7086 via a snap fitting. The spoke fluid collection system 7058 further comprises a spoke connector 7088 connecting the central hub 7060 to a needle hub or a three-way valve. Fluid flows from a needle hub or a three-way valve through the spoke connector 7088 and into a first collection tube 7010*a*. In some embodiments, the fluid exits the spoke connector 7088 and flows only into a first collection tube 7010*a* that is immediately underneath the spoke connector 7088. The spoke fluid collection system 7058 further comprises a knob (not shown in FIG. 7) secured to the back face of the central hub 7060, which is rotated clockwise or counterclockwise to allow for sequential filling of the collection tubes 7010. In some embodiments, the knob either clicks into place or has markings corresponding to four positions, which, when aligned, signals whether a first collection tube 7010*a*, a second collection tube 7010*b*, a third collection tube 7010*c*, or a fourth collection tube 7010*d* is in position to be filled. Once a first collection tube 7010*a* is sufficiently filled, the knob is turned clockwise or counterclockwise to allow a second collection tube 7010*b*, a third collection tube 7010*c*, or a fourth collection tube 7010*d* to be filled. In some embodiments, the central hub openings 7086 comprise gaskets. In some embodiments, the gaskets prevent fluid from spilling or exiting the collection tubes 7010 during or between filling periods.

Figure 8:
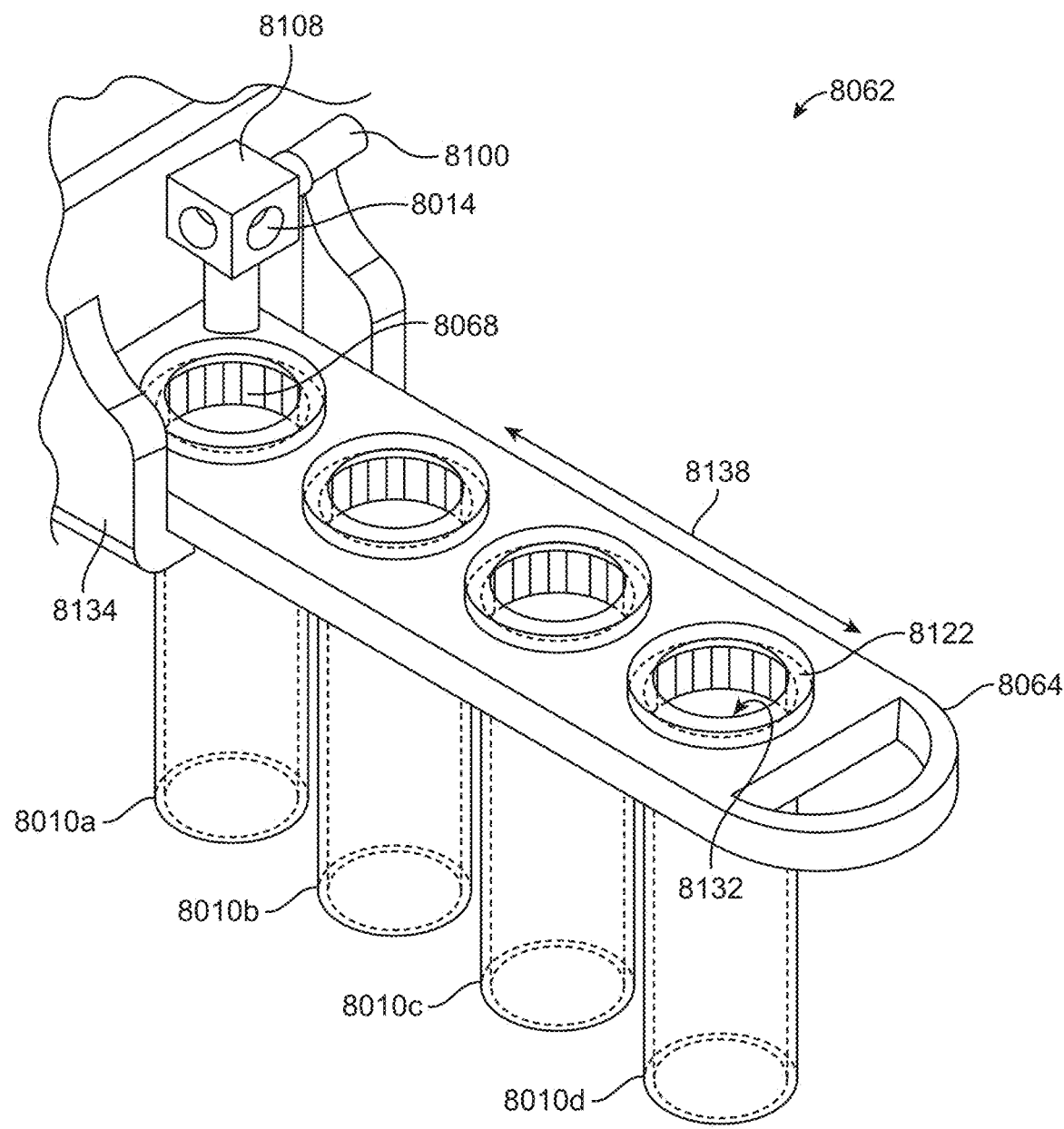
FIG. 8 illustrates a rail fluid collection system of the tactile sensing.

In some embodiments, the tactile sensing device comprises a rail fluid collection system 8062, as shown in FIGS. 2 and 8. In some embodiments, the rail fluid collection system 8062 comprises a rail platform 8064 located beneath a needle hub connector 8100, a fluid connector 8068, or a three-way valve 8014. The rail platform 8064 slides along guide rails 8134, which are operatively connected to the tactile sensing device. In some embodiments, the fluid collection tubes 8010 are placed beneath a fluid connector 8068 to allow for fluid collection. Once fluid begins to flow, the user waits for a first collection tube 8010*a* to fill; then, the user slides the rail platform 8064 containing the collection tubes 8010 to allow for sequential filling of a second collection tube 8010*b*, a third collection tube 8010*c*, and a fourth collection tube 8010*d*.

Frame

In some embodiments, as shown in FIGS. 1A, 1B, 1C, 2A, 2B, and 2C, the tactile sensing device 1000, 2000 comprises a frame 1018. In some embodiments, the frame 1018 is a basic structure that supports the modular components of the tactile sensing device. In some embodiments, the frame 1018 or 2018 holds the modular components of the tactile sensing device. In some embodiments, the frame 1018 or 2018 has a plurality of voids that are filled with a plurality of protrusions from the modular components of the tactile sensing device. In some embodiments, the modular components of the tactile sensing device include a sensor array 1008, 2008, 3008, the diaphragm fluid collection system 5042, the faucet fluid collection system 6048, the spoke fluid collection system 7058, or the rail fluid collection system 8062. In some embodiments, the frame 1018 or 2018 is composed of a metal, plastic, or elastomer material. In some embodiments, the frame 1018 or 2018 is made out of a plastic or elastomer material including, but not limited to: polyethylene; polypropylene; polystyrene; polyester; polylactic acid (PLA); polycarbonate, polyvinyl chloride, polyethersulfone, polyacrylate or acrylic or polymethylmethacrylate (PMMA); polysulfone; polyetheretherketone; thermoplastic elastomers or thermoplastic urethanes; or poly-p-xylylene or parylene.

Handle

In some embodiments, as shown in in FIGS. 1A, 1B, and 1C, the tactile sensing device comprises a handle 1004. In some embodiments, the handle 1004 is operatively connected to the tactile sensing device 1000. In some embodiments, the handle 1004 is a part of the tactile sensing device 1000 by which the tactile sensing device 1000 is held, controlled, carried, maneuvered, or gripped. In some embodiments, the gripper 1004 orients the user's hand in a forward orientation. In some embodiments, as shown in in FIGS. 2A, 2B, and 2C, the tactile sensing device comprises a gripper 2020. In some embodiments, the gripper 2020 is operatively connected to the tactile sensing device 2000. In some embodiments, the gripper 2020 is a part of the tactile sensing device 2000 by which the tactile sensing device 2000 is held, controlled, carried, maneuvered, or gripped. In some embodiments, as shown in FIGS. 2A, 2B, and 2C, the gripper 2020 is ergonomically shaped and configured to enhance application of force to the tactile sensing device 2004. In some embodiments, a fluid collection system is contained within a void inside the handle of the tactile sensing device 1000. In some embodiments, the handle 1004 or gripper 2020 comprises a plastic or elastomer material including, but not limited to: polyethylene; polypropylene; polystyrene; polyester; polylactic acid (PLA); polycarbonate, polyvinyl chloride, polyethersulfone, polyacrylate or acrylic or polymethylmethacrylate (PMMA); polysulfone; polyetheretherketone (PEEK); thermoplastic elastomers or thermoplastic urethanes; or poly-p-xylylene or parylene. In some embodiments, the handle 1004 or gripper 2020 is made out of a rubber material including, but not limited to: silicone rubber, natural rubber, acrylonitrile-butadiene rubber, hydrogenated acrylonitrile-butadiene rubber, ethylene propylene diene rubber, fluorocarbon rubber, chloroprene rubber, fluoro silicone rubber, polyacrylate rubber, ethylene acrylic rubber, styrene-butadiene rubber, polyester urethane rubber, or polyether urethane rubber.

Tactile Sensing Device: Systems

Disclosed herein, in certain embodiments, are systems for imaging bone and non-bone structures in an individual in need thereof, comprising: a tactile sensing device to detect voltage signals resulting from application of force to the tactile sensing device against the individual; a display screen to visualize an image of the bone and non-bone structures obtained from the voltage signals detected by the tactile sensing device; and a computing device comprising: at least one processor operatively coupled to the tactile sensing device; a memory device; and a non-transitory computer readable storage medium with a computer program including instructions executable by the processor causing the processor to convert the voltage signals into the image.

Bone and Non-Bone Structures

In some embodiments, the systems for imaging bone and non-bone structures image a first and second bone and non-bone structures. In some embodiments, the systems for imaging bone and non-bone structures image a plurality of bone and non-bone structures. In some embodiments, a bone structure is a rib. In some embodiments, a bone structure is an articular surface. In some embodiments an articular surface is a vertebral articulation, an articulation of a first bone of a hand with a second bone of the hand, an elbow joint, a wrist joint, an axillary articulation of a first bone of a shoulder with a second bone of the shoulder, a sternoclavicular joint, a temporomandibular joint, a sacroiliac joint, a hip joint, a knee joint, or an articulations of a first bone of a foot with a second bone of the foot. In some instances, a vertebral articulation is a spinous process. In some embodiments, a non-bone structure is subcutaneous tissue, a muscle, a ligament, adipose tissue, a cyst, or a cavity.

Sensor Array

In some embodiments, the tactile sensing device 1000 comprises a sensor array 1008. In some embodiments, the sensor array comprises a plurality of sensors. In some embodiments, the sensors are tactile sensors. In some embodiments, the sensors are force-sensitive resistors. In some embodiments, the force-sensitive resistors change their resistive value in response to a change in applied pressure. In some instances, the force-sensitive resistors output voltage signals. In some embodiments, the array of force-sensitive resistors is a 6×3 array comprising eighteen force-sensitive resistors. In some embodiments, the array of force-sensitive resistors is an 8×4 array comprising thirty two force-sensitive resistors. In some embodiments, the size of the array of force-sensitive resistors is dependent upon the surface area of the individual's body to be examined. In some embodiments, the array of force-sensitive resistors is configured in a way that is sufficient to visualize the bone and non-bone structures in the individual.

In some embodiments, as shown in FIGS. 3A and 3B, the array of force-sensitive resistors is secured onto a sensor array platform 3022. In some embodiments, the sensor array platform 3022 comprises cylindrical struts 3026 onto which the sensors are adhered to. In some embodiments, the cylindrical struts 3026 onto which the sensors are adhered to are struts or connectors of any shape that adequately supports the sensors being used.

Display Screen

As shown in FIGS. 1A, 1B, 1C, 2A, 2B, and 2C, in some embodiments, the tactile sensing device 1000, 2000 comprises a display screen 1032, 2032 to provide visual information to a user. In some embodiments, the display screen 1032 is operatively connected to the tactile sensing device 1000. In some embodiments, the display screen 2032 is operatively connected to the tactile sensing device 2000. In some embodiments, the display screen is a computer screen, a mobile device screen, or a portable device screen. In some embodiments, the display screen is a cathode ray tube (CRT). In some embodiments, the display screen is a liquid crystal display (LCD). In further embodiments, the display screen is a thin film transistor liquid crystal display (TFT-LCD). In some embodiments, the display screen is an organic light emitting diode (OLED) display. In various further embodiments, an OLED display is a passive-matrix OLED (PMOLED) or active-matrix OLED (AMOLED) display. In some embodiments, the display screen is a plasma display. In other embodiments, the display screen is a video projector. In still further embodiments, the display screen is a combination of devices such as those disclosed herein.

In some embodiments, the visual information provided to the user via a display screen is a pressure map representing bone and non-bone structures. In some embodiments, the pressure map is a heat map. In some embodiments, the heat map is a graphical representation of voltage signals wherein the individual voltage output signals are represented as a plurality of colors, color hues, color saturations, graphical patterns, shading, geometrical figures, or any combination thereof.

Computing Device

In some embodiments, the tactile sensing device further comprises a computing device. In some embodiments, the computing device is a microcontroller. In some embodiments, the microcontroller is an 8-bit, 16-bit, or 32-bit microcontroller. In some embodiments, the microcontroller is an 8051 microcontroller, a programmable interface controller (PIC), an AVR or Advanced Virtual RISC microcontroller, or an ARM® microcontroller. In some embodiments, the microcontroller is, by way of non-limiting examples, an Arduino Uno microcontroller or a Raspberry Pi microcontroller.

In some embodiments, the computing device is a microprocessor. In some embodiments, the microprocessor is manufactured by AMD®, Intel®, or ARM®. In some embodiments, the AMD® microprocessors include, but are not limited to: AMD Sempron™, AMD Turion II™, AMD Athlon II™, AMD Sempron™, AMD Phenom II™, AMD A-Series, or AMD FX™. In some embodiments, the Intel® microprocessors include, but are not limited to: Intel Atom™, Intel Celeron™, Intel Pentium™, Intel Core i3™, Intel Core i5™, or Intel Core i7™. In some embodiments, the ARM® microprocessors include, but are not limited to: ARM OMAP 3, ARM MAP 4, ARM OMAP 5, ARM SnapDragon S2, ARM SnapDragon S, ARM SnapDragon S4, ARM Tegra, ARM Tegra 2, ARM Tegra 3, ARM Exynos 3 Single, ARM Exynos 4 Dual, ARM Exynos 4 Quad, ARM Exynos 5 Dual, ARM A4, ARM A5, or ARM A5X.

In some embodiments, the computing device further comprises a memory device. In some embodiments, the processing device includes a memory device. A memory device is one or more physical apparatus used to store data or programs on a temporary basis, a permanent basis, or combinations thereof. In some embodiments, a memory device is volatile and requires power to maintain stored information. In some embodiments, a memory device is non-volatile and retains stored information and does not require power to maintain stored information.

In some embodiments, the computing device further comprises a non-transitory computer readable storage medium with a computer program including instructions executable by the processor causing the processor to convert the voltage signals into an image. In some embodiments, the computer program includes instructions executable by the processor that cause the processor to encode the voltage signals into a first and second computer signals.

In some embodiments, the computer program includes instructions executable by the processor that cause the processor to calculate a projected needle position and display it on the display screen. In some embodiments, the computer program includes instructions executable by the processor that cause the processor to calculate a projected needle position for any potential needle guide when using a tactile sensing device 2000 comprising a needle guide cartridge 2012, as shown in FIGS. 2A, 2B, and 2C. In some embodiments, a needle projection calculation is a trigonometric algorithm. In some embodiments, the trigonometric algorithm determines the depth of the needle once it traverses subcutaneous adipose tissue. In some embodiments, the needle projection calculation is adjusted based on amount of subcutaneous adipose tissue.

In some embodiments, the computer program includes instructions executable by the processor causing the processor to: determine, as a first requirement, a location of a bone detected by the tactile sensing device; ii) determine, as a second requirement, the space between said bone structures; and iii) perform predictive analysis based on application of machine learning. In some embodiments, the predictive analysis performed by the processor enhances the accuracy of a needle projection calculation. In some embodiments, the predictive analysis performed by the processor locates a desired bone and non-bone structure. In some embodiments, the predictive analysis performed by the processor locates a gap between bone and non-bone structures. In some embodiments, the predictive analysis performed by the processor suggests a needle insertion location to the user based on the voltage signals detected by the tactile sensing device.

The computer program is, for example, software, including computer algorithms, computer codes, programs, and data, which manages the device's hardware and provides services for execution of instructions. Suitable computer program languages include, by way of non-limiting examples, C, C++, C#, Objective C, Perl, Scala, Haskell, Go, Arduino C, Python, Java, SQL, JavaScript, PHP, iOS Swift, or Ruby.

In some embodiments, the computing device is a desktop computer or a laptop computer. In some embodiments, the computing device is a mobile device. In some embodiments, the mobile device is a smart phone or a smart watch. In some embodiments, the computing device is a portable device. In accordance with the description herein, suitable computing devices further include, by way of non-limiting examples, notebook computers, tablet computers, netbook computers, smart book computers, subnotebook computers, ultra-mobile PCs, handheld computers, personal digital assistants, Internet appliances, smart phones, music players, and portable video game systems. Many mobile smart phones are suitable for use in the systems described herein. Suitable tablet computers include those with booklet, slate, and convertible configurations. Suitable portable video game systems include, by way of non-limiting examples, Nintendo DS™ and Sony® PSP™.

Signal Transmitter and Receiver

In some embodiments, the processor encodes the voltage signals into a first and second computer signals. In some embodiments, the tactile sensing device comprises a signal transmitter. In some embodiments, the tactile sensing device comprises a signal receiver. In some embodiments, a transmitter is configured to transmit the first computer signal to a computing device. In some embodiments, a receiver is configured to receive the second computer signal from a tactile sensing device. In some embodiments, the first and second computer signals are transmitted via a USB (Universal Serial Bus) cable. In some embodiments, the first and second computer signals are wireless signals.

In some embodiments, the signal receiver is a wireless element. In some embodiments, the signal transmitter is a wireless element. In some embodiments, the wireless element is configured to receive a signal from a computing device, for example, a mobile device. In some embodiments, the signal receiver is a wireless element which is configured to receive a signal from the tactile sensing device. In some embodiments, the wireless element is a wireless network technology. In some embodiments, the wireless network technology is ANT, ANT+, INSTEON, IrDA, Wireless USB, Bluetooth, Z-Wave, or ZigBee, IEEE 802.15.4, 6LoWPAN, or Wi-Fi.

Needles and Needle Guide

In some embodiments, the system further comprises a needle, a needle guide, a stylet, or a catheter. In some embodiments, the needle is an atraumatic, also known as pencil-point type needle, or a traumatic needle, also known as a classic needle or a Quincke type needle. In some embodiments, the system further comprises a spinal needle. In some embodiments, the spinal needle is a Quincke spinal needle, a Whitacre spinal needle, or a Sprotte spinal needle. In some embodiments, the system further comprises an epidural needle. In some embodiments, the epidural needle is a Weiss epidural needle, a Tuohy epidural needle, or a Hustead epidural needle. In some embodiments, the needle incudes, by way of non-limiting examples, a 6-gauge needle, an 8-gaurge needle, a 13-gauge needle, a 15-gauge needle, a 17-gauge needle, an 18-gauge needle, a 19-gauge needle, a 20-gauge needle, a 21-gauge needle, a 22-gauge needle, a 23-gauge needle, a 24-gauge needle, a 25-gauge needle, a 26-gauge needle, a 27-gauge needle, a 28-gauge needle, a 29-gauge needle, a 30-gauge needle, a 31-gauge needle, and a 32-gauge needle. In some embodiments, the needle is a spinal needle ranging between 1-10 inches in length. In some embodiments, the needle contains a stylet, also known as an obturator or an introducer, which is a fine wire, a slender probe, or a solid rod with a metal hub fitted to match a needle's bevel. In diagnostic lumbar punctures, a stylet is withdrawn from the needle to allow cerebrospinal fluid to flow out from the spinal canal and through the needle hub.

In some embodiments, the system further comprises a catheter. In some embodiments, the catheter is an epidural tunneled catheter, which is implanted into the epidural space as a medication delivery port. In some embodiments, the catheter is used to monitor intracranial pressure during a diagnostic lumbar puncture procedure. In some embodiments, the catheter is used as means to continuously remove cerebrospinal fluid and relieve pressure on the brain of a patient suffering from hydrocephalus.

In some embodiments, a needle guide 1002 is operatively connected to the tactile sensing device 1000. In some embodiments, the needle guide 1002, operatively connected to the tactile sensing device 1000, is used to control the angle and direction of a needle that is inserted into an individual in need thereof. In some embodiments, the needle guide 1002 is oriented between a −45° and 45° cephalad angle, terminating at a needle orifice 1038 located on the center of the sensor array 1008, thereby controlling the angle at which the needle is inserted into a human body. In some embodiments, the needle guide 1002 is oriented at a 15° cephalad angle. In some embodiments, the needle orifice 1038 located on the center of the sensor array 1008 is an elongated slit. In some embodiments, the needle guide 1002 terminates at a plurality of openings formed by an elongated slit with a plurality of columns. In various further embodiments, as shown in FIGS. 2A, 2B, and 2C, a needle guide cartridge 2012 is operatively connected to the tactile sensing device 2000. In some embodiments, the needle guide cartridge 2012 is oriented between a −45° and 45° cephalad angle, terminating at needle orifice 2038 located along the midline of the sensor array 2008, thereby controlling the angle at which the needle is inserted into a human body. In some embodiments, the needle guide cartridge 2012 is oriented at a 15° cephalad angle. In some embodiments, the needle guide cartridge 2012 2012 terminates at an opening. In some embodiments, the needle orifice 2038 located on the center of the sensor array 2008 is an elongated slit.

Fluid Collection System

In some embodiments, the system further comprises a fluid collection system operatively connected to the tactile sensing device and configured to collect a fluid such as cerebrospinal fluid. In some embodiments, the fluid collection system is disposable. In some embodiments, the fluid collection system comprises a diaphragm, faucet, top faucet, spoke, or rail design. In some embodiments, the fluid collection system is sterile. In some embodiments, the fluid collection system is modular.

Pressure Sensor

In some embodiments, the system further comprises a pressure sensor operatively connected to the tactile sensing device and configured to measure cerebrospinal fluid pressure. In some embodiments, the pressure sensor is operatively connected to the tactile sensing device via a 3-way valve. In some embodiments, the pressure sensor is an electronic pressure sensor. In some instances, the pressure sensor is a piezoresistive, capacitive, electromagnetic, piezoelectric, optical, or potentiometric pressure sensor. In some embodiments, cerebrospinal fluid pressure measured with the electronic pressure sensor is displayed digitally. In some embodiments, cerebrospinal fluid pressure measured with the electronic pressure sensor is displayed on a display screen in real-time.

Tactile Sensing Device: Uses

Figure 4:
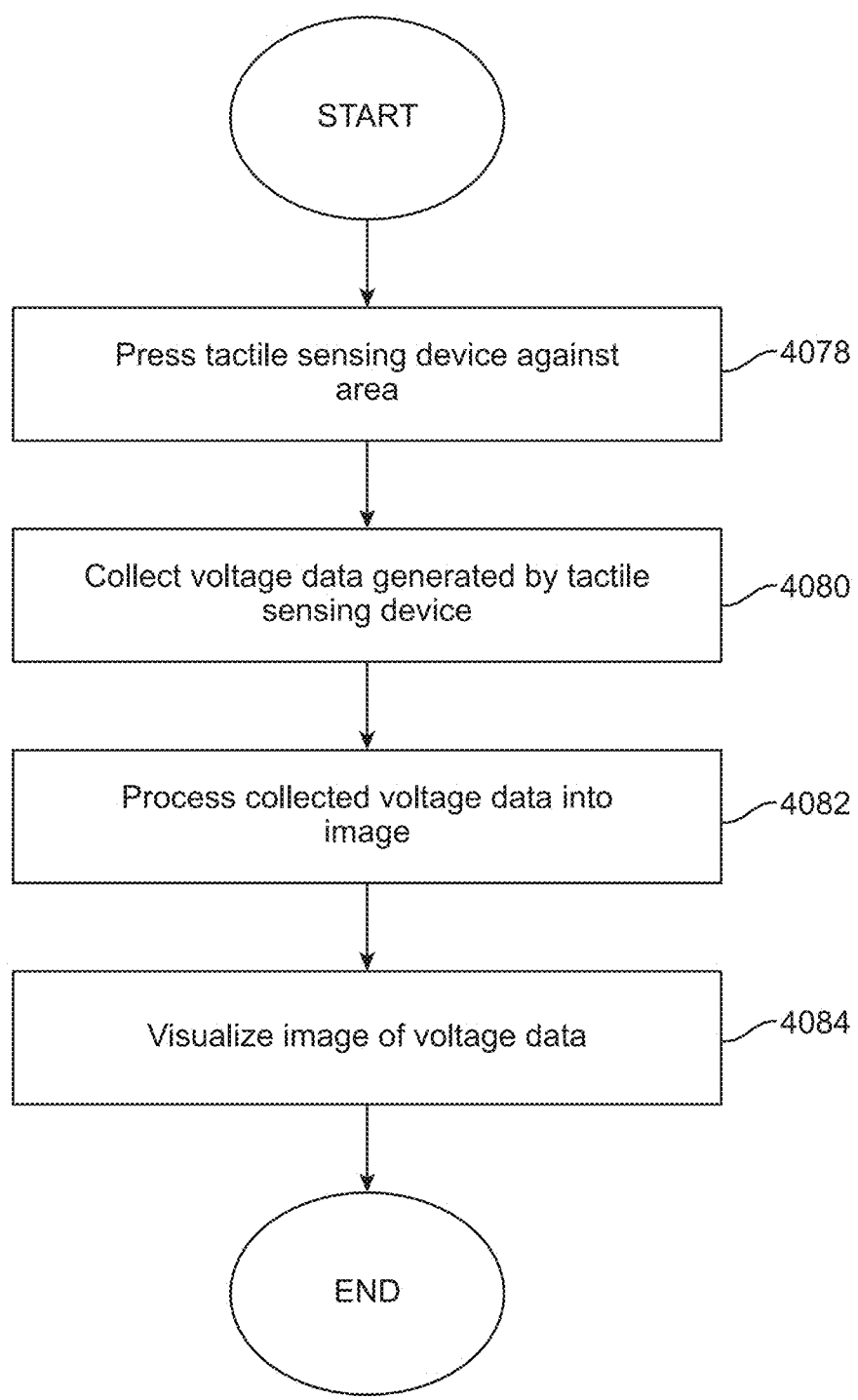
FIG. 4 is an exemplary flowchart illustrating a method of to generate an image with the tactile sensing device.

Disclosed herein, in certain embodiments, are methods for imaging bone and non-bone structures in an individual in need thereof, comprising: placing a tactile sensing device on the individual; applying force to the tactile sensing device against the individual; and viewing an image of bone and non-bone structures, obtained from voltage signals detected by the tactile sensing device, resulting from the application of force to the tactile sensing device against an individual, on a display screen. FIG. 4 exemplifies these methods for imaging bone and non-bone structures in a flowchart. In some embodiments, the process to image bone and non-bone structures with the tactile sensing device during a lumbar puncture begins by having the user identify the midline of the patient by moving the tactile sensing device laterally along the patient's back until the midline is identified. In some embodiments, the midline of the patient is identified when the image of the bone and non-bone structures shows the patient's spine centered on the display screen. In some embodiments, once the tactile sensing device is correctly aligned along the midline of the patient, the user ensures force is applied to the tactile sensing device and against the patient 4078, in order to obtain the most accurate readings. In some embodiments, voltage signals is generated by the tactile sensing device and then collected 4080, as shown in FIG. 4. In some embodiments, the collected voltage signals is processed by a computing device and transformed into an image 4082, which the user visualizes 4084 on the display screen.

Figure 10:
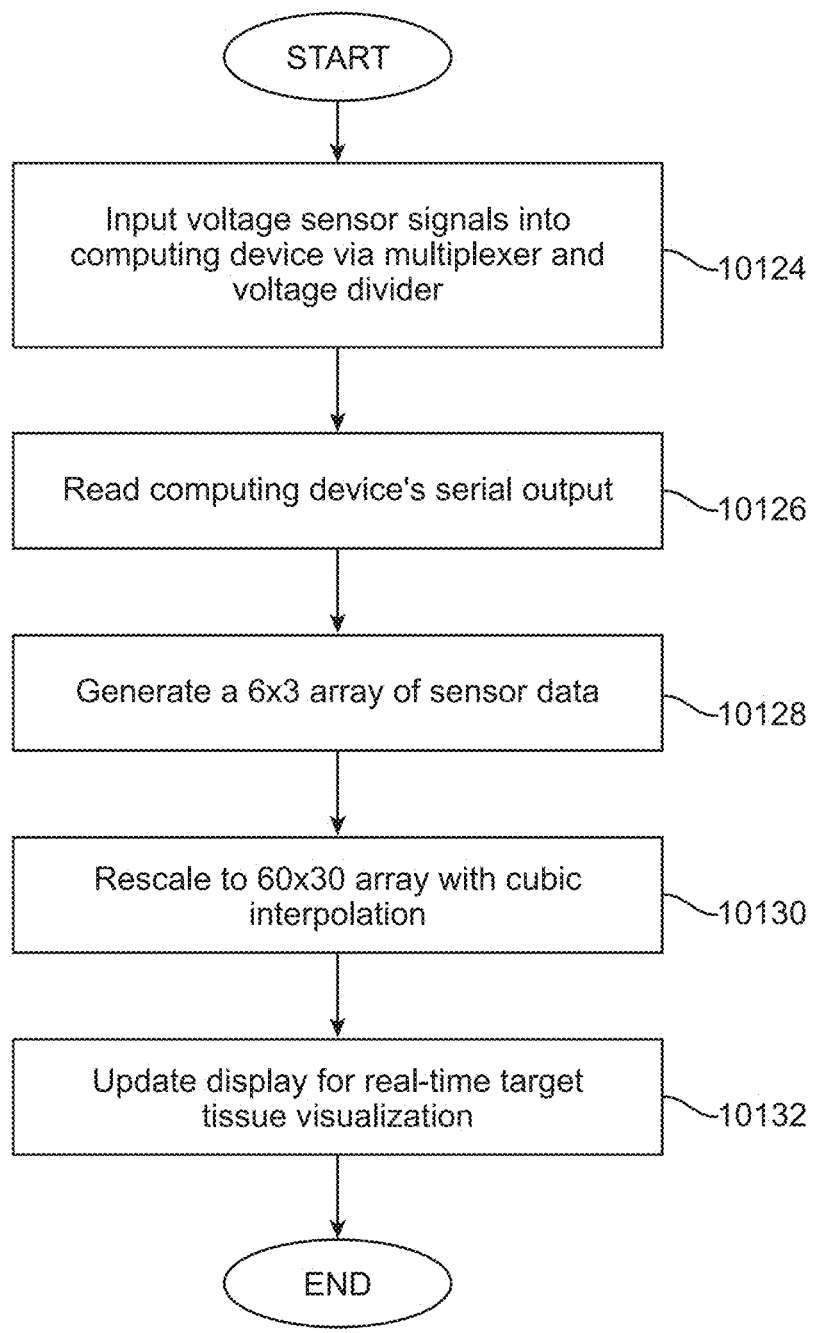
FIG. 10 is an exemplary flowchart illustrating one method for generating an image from voltage signals collected by the tactile sensing device.

Disclosed herein, in certain embodiments, are methods for generating an image of bone and non-bone structures in an individual in need thereof, comprising: collecting voltage signals detected by a tactile sensing device, resulting from the application of force to the tactile sensing device against an individual; converting the voltage signals into a mathematical array; rescaling the mathematical array; and transforming the rescaled mathematical array into an image of bone and non-bone structures of the individual. In some embodiments, converting the voltage signals comprises acquiring, processing, and transforming the signals into the image using a computer processor. FIG. 10 exemplifies these methods for generating an image of bone and non-bone structures in a flowchart. In some embodiments, voltage signals generated by the tactile sensing device are transmitted via a multiplexer and a voltage divider. In some embodiments, voltage signals generated by the tactile sensing device are transmitted via a voltage divider. In some embodiments, the transmitted voltage signals are collected using a computer processor 10124. In some embodiments, the computer processor converts the collected voltage signals into a mathematical array 10126. In some embodiments, the computer processor rescales the mathematical array 10128. In some embodiments, the rescaled mathematical array is transformed into an image 10130 that is displayed in real-time on the display screen.

Bone and Non-Bone Structures

In some embodiments, the methods for imaging bone and non-bone structures comprise imaging a first and second bone and non-bone structures. In some embodiments, the methods for generating an image of bone and non-bone structures comprise generating an image of a first and second bone and non-bone structures. In some embodiments, the methods for imaging bone and non-bone structures image a plurality of bone and non-bone structures. In some embodiments, the methods for generating an image of bone and non-bone structures image a plurality of bone and non-bone structures. In some embodiments, the methods for imaging bone and non-bone structures comprise placing the tactile sensing device on the individual. In some embodiments, placing the tactile sensing device on the individual further comprises positioning the tactile sensing device on a bone structure. In some embodiments, a bone structure is a rib. In some embodiments, a bone structure is an articular surface. In some embodiments an articular surface is a vertebral articulation, an articulation of a first bone of a hand with a second bone of the hand, an elbow joint, a wrist joint, an axillary articulation of a first bone of a shoulder with a second bone of the shoulder, a sternoclavicular joint, a temporomandibular joint, a sacroiliac joint, a hip joint, a knee joint, or an articulations of a first bone of a foot with a second bone of the foot. In some instances, a vertebral articulation is a spinous process. In some embodiments, a non-bone structure is subcutaneous tissue, a muscle, a ligament, adipose tissue, a cyst, or a cavity.

Sensor Array

In some embodiments, the tactile sensing device 1000 comprises a sensor array 1008. In some embodiments, the sensor array comprises tactile sensors. In some embodiments, the tactile sensors are force-sensitive resistors. In some embodiments, the force-sensitive resistors change their resistive value in response to a change in applied pressure. In some instances, the force-sensitive resistors output voltage signals. In some embodiments, the array of force-sensitive resistors is a 6×3 array comprising eighteen force-sensitive resistors. In some embodiments, the array of force-sensitive resistors is an 8×4 array comprising thirty two force-sensitive resistors. In some embodiments, the size of the array of force-sensitive resistors is dependent upon the surface area of the individual's body to be examined. In some embodiments, the array of force-sensitive resistors is configured in a way that is sufficient to visualize the bone and non-bone structures in the individual.

In some embodiments, as shown in FIGS. 3A and 3B, the array of force-sensitive resistors is secured onto a sensor array platform 3022. In some embodiments, the sensor array platform 3022 comprises cylindrical struts 3026 onto which the force-sensitive resistors are adhered to. In some embodiments, the cylindrical struts 3026 onto which the force-sensitive resistors are adhered are connectors. In some embodiments, each sensor 3016 is covered with a material configured to enhance force feedback. In some embodiments, the material covering the force-sensitive resistors is a hemispherical rubber disk.

Multiplexer

In some embodiments, the tactile sensing device further comprises a multiplexer. The multiplexer selects voltage output signals from the force-sensitive resistors and forwards the selected voltage output signals into a single line. In some embodiments, the multiplexer is mounted onto a printed circuit board.

Voltage Divider

In some embodiments, the tactile sensing device further comprises a voltage divider. In some embodiments, the voltage signal output from the force-sensitive resistors is read out using a voltage divider.

Pressure Map

In some embodiments, the image of bone and non-bone structures provided to the user via a display screen is a pressure map representing bone and non-bone structures. In some embodiments, the pressure map is a heat map. In some embodiments, the heat map is a graphical representation of voltage signals wherein the individual voltage output signals are represented as a plurality of colors, color hues, color saturations, graphical patterns, shading, geometrical figures, or any combination thereof. In some embodiments, the pressure map is overlaid onto a second image.

Lumbar Puncture Methods

Disclosed herein, in certain embodiments, are methods for performing a lumbar puncture in an individual in need thereof, comprising: placing a tactile sensing device on a lumbar region of the individual; applying force to the tactile sensing device against the lumbar region; viewing voltage signals, corresponding to vertebral articulations, detected by the tactile sensing device resulting from the application of force to the tactile sensing device against the lumbar region, on a display screen; localizing two spinous processes on the image; identifying a gap between a first spinous process and a second spinous process of the individual; using a needle guide to insert a needle between the first and second spinous processes of the individual and into a subarachnoid space; and collecting cerebrospinal fluid or administering a therapeutic agent.

Epidural Methods

Disclosed herein, in certain embodiments, are methods for administering a therapeutic agent to an epidural space of an individual in need thereof, comprising: placing a tactile sensing device on a lumbar region of the individual; applying force to the tactile sensing device against the lumbar region; viewing voltage signals, corresponding to vertebral articulations, detected by the tactile sensing device resulting from the application of force to the tactile sensing device against the lumbar region, on a display screen; localizing two spinous processes on the image; identifying a gap between a first spinous process and a second spinous process of the individual; using a needle guide to insert a needle between the first and second spinous processes and into the epidural space of the individual; and injecting a therapeutic agent into the epidural space.

Therapeutic Agents

In some embodiments, therapeutic agents are delivered via a lumbar puncture. In some embodiments, therapeutic agents delivered via a lumbar puncture include but are not limited to: anesthetics, analgesics, chemotherapeutic agents, contrast agents or dyes, anti-spasmodic agents, antibiotics, or proteins. In some embodiments, anesthetics delivered via a lumbar puncture include but are not limited to: bupivacaine, lidocaine, tetracaine, procaine, ropivacaine, levobupivacaine, prilocaine, and cinchocaine. In some embodiments, analgesics delivered via a lumbar puncture include but are not limited to: opioids such as morphine, fentanyl, diamorphine, buprenorphine, and pethidine or meperidine; and non-opioids such as clonidine. In some embodiments, chemotherapeutic agents delivered via a lumbar puncture include but are not limited to: methotrexate, cytarabine, hydrocortisone, and thiotepa. In some embodiments, contrast agents or dyes delivered via a lumbar puncture include but are not limited to: iohexol, metrizamide, iopamidol, ioversol, iopromide, iodixanol, iolotran, and iodophenylundecylic acid. In some embodiments, antispasmodic agents delivered via a lumbar puncture include baclofen. In some embodiments, antibiotics delivered via a lumbar puncture include gentamicin sulphate. In some embodiments, proteins delivered via a lumbar puncture include idursulfase.

Spinous Processes

In some embodiments, methods for performing a lumbar puncture in an individual in need thereof comprise using a needle guide to insert a needle between the first and second spinous processes and into the subarachnoid space of the individual. In some embodiments, methods for administering a therapeutic agent to an epidural space of an individual in need thereof comprise using a needle guide to insert a needle between the first and second spinous processes and into the epidural space of the individual. In some embodiments, the first spinous process is a part of the first lumbar vertebra (L1), L2, L3, or L4 lumbar vertebrae and the second spinous process is a part of L2, L3, L4, or L5 lumbar vertebrae. In some further embodiments, the first and spinous process is a part of any cervical, thoracic, lumbar, sacrum, or coccyx vertebrae.

Needles and Needle Guide

In some embodiments, the system further comprises a needle, a needle guide, a stylet, or a catheter. In some embodiments, the needle is an atraumatic, also known as pencil-point type needle, or a traumatic needle, also known as a classic needle or a Quincke type needle. In some embodiments, the system further comprises a spinal needle. In some embodiments, the spinal needle is a Quincke spinal needle, a Whitacre spinal needle, or a Sprotte spinal needle. In some embodiments, the system further comprises an epidural needle. In some embodiments, the epidural needle is a Weiss epidural needle, a Tuohy epidural needle, or a Hustead epidural needle. In some embodiments, the needle incudes, by way of non-limiting examples, a 6-gauge needle, an 8-gaurge needle, a 13-gauge needle, a 15-gauge needle, a 17-gauge needle, an 18-gauge needle, a 19-gauge needle, a 20-gauge needle, a 21-gauge needle, a 22-gauge needle, a 23-gauge needle, a 24-gauge needle, a 25-gauge needle, a 26-gauge needle, a 27-gauge needle, a 28-gauge needle, a 29-gauge needle, a 30-gauge needle, a 31-gauge needle, and a 32-gauge needle. In some embodiments, the needle is a spinal needle ranging between 1-10 inches in length. In some embodiments, the needle contains a stylet, also known as an obturator or an introducer, which is a fine wire, a slender probe, or a solid rod with a metal hub fitted to match a needle's bevel. In diagnostic lumbar punctures, a stylet is withdrawn from the needle to allow cerebrospinal fluid to flow out from the spinal canal and through the needle hub.

In some embodiments, the system further comprises a catheter. In some embodiments, the catheter is an epidural tunneled catheter, which is implanted into the epidural space as a medication delivery port. In some embodiments, the catheter is used to monitor intracranial pressure during a diagnostic lumbar puncture procedure. In some embodiments, the catheter is used as means to continuously remove cerebrospinal fluid and relieve pressure on the brain of a patient suffering from hydrocephalus.

In some embodiments, a needle guide 1002 is operatively connected to the tactile sensing device 1000. In some embodiments, the needle guide 1002, operatively connected to the tactile sensing device 1000, is used to control the angle and direction of a needle that is inserted into an individual in need thereof. In some embodiments, the needle guide 1002 is oriented between a −45° and 45° cephalad angle, terminating at a needle orifice 1038 located on the center of the sensor array 1008, thereby controlling the angle at which the needle is inserted into a human body. In some embodiments, the needle guide 1002 is oriented at a 15° cephalad angle. In some embodiments, the needle orifice 1038 located on the center of the sensor array 1008 is an elongated slit. In some embodiments, the needle guide 1002 terminates at a plurality of openings formed by an elongated slit with a plurality of columns. In various further embodiments, as shown in FIGS. 2A, 2B, and 2C, a needle guide cartridge 2012 is operatively connected to the tactile sensing device 2000. In some embodiments, the needle guide cartridge 2012 is oriented between a −45° and 45° cephalad angle, terminating at a needle orifice 2038 located along the midline of the sensor array 2008, thereby controlling the angle at which the needle is inserted into a human body. In some embodiments, the needle guide cartridge 2012 is oriented at a 15° cephalad angle. In some embodiments, the needle guide cartridge 2012 terminates at an opening. In some embodiments, the needle orifice 2038 located on the center of the sensor array 2008 is an elongated slit.

Guiding Methods

Disclosed herein, in certain embodiments, are methods for guiding a first individual performing a lumbar puncture on a second individual in need thereof, comprising: placing a tactile sensing device on a lumbar region of the individual; applying force to the tactile sensing device against the lumbar region; viewing voltage signals, corresponding to vertebral articulations, detected by the tactile sensing device resulting from the application of force to the tactile sensing device against the lumbar region, on a display screen; localizing two spinous processes on the image; identifying a gap between a first spinous process and a second spinous process of the individual; using a needle guide to insert a needle between the first and second spinous processes of the individual and into a subarachnoid space; and collecting cerebrospinal fluid or administering a therapeutic agent.

Disclosed herein, in certain embodiments, are methods for guiding a first individual administering a therapeutic agent into an epidural space of a second individual in need thereof, comprising: placing a tactile sensing device on a lumbar region of the individual; applying force to the tactile sensing device against the lumbar region; viewing voltage signals, corresponding to vertebral articulations, detected by the tactile sensing device resulting from the application of force to the tactile sensing device against the lumbar region, on a display screen; localizing two spinous processes on the image; identifying a gap between a first spinous process and a second spinous process of the individual; using a needle guide to insert a needle between the first and second spinous processes and into the epidural space of the individual; and injecting a therapeutic agent into the epidural space.

Tactile Sensing Device: Kits

Disclosed herein, in certain embodiments, are kits for performing a diagnostic lumbar puncture in an individual in need thereof, comprising: a tactile sensing device to image bone and non-bone structures in the individual; a computer to process voltage signals detected by the tactile sensing device; a display screen to visualize the bone and non-bone structures; an electronic pressure sensor to measure cerebrospinal fluid pressure; and a fluid collection system to collect cerebrospinal fluid.

Sensor Array

In some embodiments, the tactile sensing device 1000 comprises a sensor array 1008. In some embodiments, the sensor array comprises a plurality of tactile sensors. In some embodiments, the tactile sensors are force-sensitive resistors. In some embodiments, the force-sensitive resistors change their resistive value in response to a change in applied pressure. In some instances, the force-sensitive resistors output voltage signals. In some embodiments, the array of force-sensitive resistors is a 6×3 array comprising eighteen force-sensitive resistors. In some embodiments, the array of force-sensitive resistors is an 8×4 array comprising thirty two force-sensitive resistors. In some embodiments, the size of the array of force-sensitive resistors is dependent upon the surface area of the individual's body to be examined. In some embodiments, the array of force-sensitive resistors is configured in a way that is sufficient to visualize the bone and non-bone structures in the individual. In some embodiments, as shown in FIGS. 3A and 3B, the array of force-sensitive resistors is secured onto a sensor array platform 3022. In some embodiments, the sensor array platform 3022 comprises cylindrical struts 3026 onto which the sensors are adhered to. In some embodiments, the cylindrical struts 3026 onto which the sensors are adhered are connectors. In some embodiments, the force-sensitive resistors are covered with a material configured to enhance force feedback. In some embodiments, the material covering the force-sensitive resistors is a hemispherical rubber disk.

Bone and Non-Bone Structures

In some embodiments, the tactile sensing device images a first and second bone and non-bone structures. In some embodiments, the tactile sensing device images a plurality of bone and non-bone structures. In some embodiments, a bone structure is a rib. In some embodiments, a bone structure is an articular surface. In some embodiments an articular surface is a vertebral articulation, an articulation of a first bone of a hand with a second bone of the hand, an elbow joint, a wrist joint, an axillary articulation of a first bone of a shoulder with a second bone of the shoulder, a sternoclavicular joint, a temporomandibular joint, a sacroiliac joint, a hip joint, a knee joint, or an articulations of a first bone of a foot with a second bone of the foot. In some instances, a vertebral articulation is a spinous process. In some embodiments, a non-bone structure is subcutaneous tissue, a muscle, a ligament, adipose tissue, a cyst, or a cavity.

Computing Device

In some embodiments, the tactile sensing device further comprises a computing device. In some embodiments, the computing device is a microcontroller. In some embodiments, the microcontroller is an 8-bit, 16-bit, or 32-bit microcontroller. In some embodiments, the microcontroller is an 8051 microcontroller, a programmable interface controller (PIC), an AVR or Advanced Virtual RISC microcontroller, or an ARM® microcontroller. In some embodiments, the microcontroller is, by way of non-limiting examples, an Arduino Uno microcontroller or a Raspberry Pi microcontroller.

Display Screen

As shown in FIGS. 1A, 1B, 1C, 2A, 2B, and 2C, in some embodiments, the tactile sensing device 1000, 2000 comprises a display screen 1032, 2032 to provide visual information to a user. In some embodiments, the display screen 1032 is operatively connected to the tactile sensing device 1000. In some embodiments, the display screen 2032 is operatively connected to the tactile sensing device 2000. In some embodiments, the display screen is a computer screen, a mobile device screen, or a portable device screen. In some embodiments, the display screen is a cathode ray tube (CRT). In some embodiments, the display screen is a liquid crystal display (LCD). In further embodiments, the display screen is a thin film transistor liquid crystal display (TFT-LCD). In some embodiments, the display screen is an organic light emitting diode (OLED) display. In various further embodiments, an OLED display is a passive-matrix OLED (PMOLED) or active-matrix OLED (AMOLED) display. In some embodiments, the display screen 1032, 2032 is a plasma display. In other embodiments, the display screen is a video projector. In still further embodiments, the display screen is a combination of devices such as those disclosed herein.

In some embodiments, the visual information provided to the user via a display screen is a pressure map representing bone and non-bone structures. In some embodiments, the pressure map is a heat map. In some embodiments, the heat map is a graphical representation of voltage signals wherein the individual voltage output signals are represented as a plurality of colors, color hues, color saturations, graphical patterns, shading, geometrical figures, or any combination thereof.

Needle Guide

In some embodiments, as shown in FIGS. 1A, 1B, and 1C, a needle guide 1002 is operatively connected to the tactile sensing device 1000. In some embodiments, the needle guide 1002, operatively connected to the tactile sensing device 1000, is used to control the angle and direction of a needle that is inserted into an individual in need thereof. In some embodiments, the needle guide 1002 is oriented between a −45° and 45° cephalad angle, terminating at a needle orifice 1038 located on the center of the sensor array 1008, thereby controlling the angle at which the needle is inserted into a human body. In some embodiments, the needle guide 1002 is oriented at a 15° cephalad angle. In some embodiments, the needle orifice 1038 located on the center of the sensor array 1008 is an elongated slit. In some embodiments, the needle guide 1002 terminates at a plurality of openings formed by an elongated slit with a plurality of columns. In various further embodiments, as shown in FIGS. 2A, 2B, and 2C, a needle guide cartridge 2012 is operatively connected to the tactile sensing device 2000. In some embodiments, the needle guide cartridge 2012 is oriented between a −45° and 45° cephalad angle, terminating at a needle orifice 2038 located along the midline of the sensor array 2008, thereby controlling the angle at which the needle is inserted into a human body. In some embodiments, the needle guide cartridge 2012 is oriented at a 15° cephalad angle. In some embodiments, the needle guide cartridge 2012 terminates at an opening. In some embodiments, the needle orifice 2038 located on the center of the sensor array 2008 is an elongated slit.

Pressure Sensor

In some embodiments, the tactile sensing device further comprises a pressure sensor operatively connected to the tactile sensing device and configured to measure cerebrospinal fluid pressure. In some embodiments, the pressure sensor is operatively connected to the tactile sensing device via a 3-way valve 2014. In some embodiments, the pressure sensor is an electronic pressure sensor. In some instances, the pressure sensor is a piezoresistive, capacitive, electromagnetic, piezoelectric, optical, or potentiometric pressure sensor. In some embodiments, cerebrospinal fluid pressure measured with the electronic pressure sensor is displayed digitally. In some embodiments, cerebrospinal fluid pressure measured with the electronic pressure sensor is displayed on a display screen in real-time.

Fluid Collection System

In some embodiments, the tactile sensing device further comprises a fluid collection system operatively connected to the tactile sensing device and configured to collect a fluid such as cerebrospinal fluid. In some embodiments, the fluid collection system is disposable. In some embodiments, the fluid collection system comprises a diaphragm, faucet, spoke, or rail design. In some embodiments, the fluid collection system is sterile. In some embodiments, the fluid collection system is modular.

FIGS. 1A, 1B, and 1C show an illustration of one embodiment of the tactile sensing device 1000. The tactile sensing device 1000 comprises a sensor array 1008, a display screen 1032, a needle guide 1002, and a faucet fluid collection system 1006. The tactile sensing device further comprises a handle 1004 in the shape of a pistol grip. The handle 1004 is proximal to the user. The tactile sensing device 1000 is configured to image a target tissue location and to guide a needle to a desired target tissue location.

Sensor array 1008 is distal to the user. Sensor array 1008 comprises 18 sensors; only a first sensor 1016a, a second sensor 1016b, a third sensor 1016c, a fourth sensor 1016d, a fifth sensor 1016e, and a sixth sensor 1016f are shown in FIG. 1B. One additional row of six sensors is found adjacent to the right of first sensor 1016a, second sensor 1016b, third sensor 1016c, fourth sensor 1016d, fifth sensor 1016e, and sixth sensor 1016f, and an additional row of six sensors is found adjacent to the left of sensor first sensor 1016a, second sensor 1016b, third sensor 1016c, fourth sensor 1016d, fifth sensor 1016e, and sixth sensor 1016f (not shown in FIGS. 1A, 1B, and 1C). In some embodiments, the sensor array 1008 is a tactile sensor array. In some embodiments, the sensor array 1008 is an ultrasound sensor array. In some embodiments, the sensor array 1008 is an infrared radiation (IR) sensor array. Sensor array 1008 is a sensor array cartridge that is pressed into a sensor array holder 1104, which is located distally, beneath the display screen 1032. Sensors in the sensor array 1008 face away from the user when the sensor array 1008 is loaded into place within the tactile sensing device. In some embodiments, the sensor array 1008 turns on once it is loaded into the sensor array holder 1104. Sensor array holder 1104 is loaded into place in a multitude of ways. Non-limiting examples of loading the sensor array 1008 into the sensor array holder 1104 that are not shown in FIGS. 1A, 1B, and 1C, include: pressing the sensor array 1008 into the sensor array holder 1104, including snap fit features that allow the sensor array 1008 to stay in place once loaded, any magnetic means to hold the sensor array 1008 in place, any mechanical means to hold the sensor array 1008 in place. In some embodiments, a tugging string is used to snap the sensor array 1008 out of the sensor array holder 1104. In some embodiments the sensor array 1008 comprises snap ledges, or other reversible means of loading the sensor array 1008 into the sensor array holder 1104. In some embodiments, the sensor array 1008 remains in place simply because it abuts the ledge of the sensor array holder 1104. In some embodiments, one or more tabs are present on the external surface of the sensor array holder 1104. The tabs are able to be twisted in order to prevent unwanted movement or removal that is distally of the sensor array 1008 relative to the sensor array holder 1104. In addition, the sensor array 1008 is reversibly loaded into the sensor array holder 1104.

The sensors in the sensor array 1008 generate output voltage signals when the user applies a force using the tactile sensing device 1000 onto a surface, for example, onto a tissue of a patient. The sensor array 1008 is operatively connected to the display screen 1032 and a computing device (not shown in FIGS. 1A, 1B, and 1C). The sensor array 1008 relays its output voltage signals to the computing device (not shown in FIGS. 1A, 1B, and 1C), the computing device processes the output voltage signals, and an image of the output voltage signals is visualized on the display screen 1032.

The needle guide 1002 is shaped as a track, and it is configured to accept a needle 1142. The needle guide 1002 includes a proximal opening 1140a and a distal opening 1140b. In some embodiments, the needle guide 1002 is oriented at a 15° cephalad angle. In some embodiments, the needle guide 1002 is oriented between a −45° and 45° cephalad angle. The needle 1142 is inserted into the needle guide 1002 through the proximal opening 1140a and sits on the needle guide 1002. Once inserted into the needle guide 1002, the needle 1142 exits the needle guide 1002 through a needle orifice 1038 located in the sensor array 1008, between the third sensor 1016c and the fourth sensor 1016d.

A 3-way valve 1014 is inserted into the needle guide 1002 through the distal slit 1090b and sits on the needle guide 1002. In some embodiments, the 3-way valve 1014 is connected to a needle via its needle hub prior to insertion into the needle guide 1002. The 3-way valve 1014 is shown in the center of the needle guide 1002 in FIGS. 1B and 1C. The 3-way valve comprises a needle hub connector 1100, a pressure gauge connector 1094, and a fluid port 1096. The needle hub connector 1100 faces distally away from the user, and it is configured to connect to a needle hub. The pressure gauge connector 1094 is oriented upward, and it is configured to connect to a pressure sensor (not shown in FIGS. 1A, 1B, and 1C). In some embodiments, the pressure gauge connector 1094 protrudes through the slit 1090. The fluid port 1096 faces the user, and it is an open port through which fluid flows freely. The fluid port 1096 faces the user, and it is an open port through which fluid, collected from a patient, flows freely. First fluid hole 1098a is located between the 3-way valve 1014 and the proximal needle guide 1002a. Second fluid hole 1098b is located directly beneath first fluid hole 1098a. In some embodiments, cerebrospinal fluid (CSF) flows freely through the fluid port 1096, follows the downward sloping needle guide 1002, flows through the first fluid hole 1098a, flows through the second fluid hole 1098b, and flows into a collection tube 1010a. In some embodiments, fluid collected from a patient flows freely through the fluid port 1096, follows the downward sloping needle guide 1002, flows through the first fluid hole 1098a, flows through the second fluid hole 1098b, and flows into a collection tube 1010a.

In some embodiments, a knob (not shown in FIGS. 1A, 1B, and 1C) is operatively connected to the 3-way valve 1014. In some embodiments, a knob (not shown in FIGS.

1A, 1B, and 1C) is operatively coupled to the tactile sensing device 1000. Non-liming examples of operatively connecting the knob (not shown in FIGS. 1A, 1B, and 1C) include: coupling the knob to the needle hub connector 1100, coupling the knob to the pressure gauge connector 1094, coupling the knob to a pressure gauge (not shown in FIG. 1A, 1B, or 1C) connected to the pressure gauge connector 1094, or coupling the knob to a pressure sensor (not shown in FIG. 1A, 1B, or 1C) connected to the pressure gauge connector 1094. The knob (not shown in FIG. 1A, 1B, or 1C) enables the needle to be reversibly moved towards the sensor array 1008 or away from the sensor array 1008, once the needle 1142 is operatively coupled to the tactile sensing device 1000. The knob (not shown in FIG. 1A, 1B, or 1C) protrudes through the slit 1090 and may be displaced through the length of the slit. In some embodiments, the knob (not shown in FIG. 1A, 1B, or 1C) protrudes through the proximal slit 1090a when the needle 1142 has not been inserted into a patient. In some embodiments, the knob (not shown in FIG. 1A, 1B, or 1C) protrudes through the distal slit 1090b or close to the distal slit 1090b when the user has inserted or is in the process of inserting the needle 1142 into a patient. The direction of the needle movement 1136 is shown in FIG. 1B.

The faucet fluid collection system 1006 comprises a central rod 1116, a faucet base 1054, a rotating handle 1052, and collection tubes 1010. The faucet base 1054 includes an elongated central rod 1116 extending upwardly therefrom. The faucet base 1054 is located directly above, and it is operatively connected to the rotating handle 1052 via a projection 1132. The rotating handle 1052 is able to be rotated clockwise or counterclockwise about an imaginary Y-axis that vertically traverses the central rod 1116. Rotating the rotating handle 1052 enables rotation of the collection tubes 1010. The collection tubes 1010 sit on the faucet base 1054. In some embodiments, the faucet base 1054 comprises individual round receptacles (not shown in FIGS. 1A, 1B, and 1C) that hold and provide support for collections tubes 1010. Collection tubes 1010 comprise a first collection tube 1010a, a second collection tube 1010b, and a third collection tube 1010c, as shown in FIG. 1B. In some embodiments, the faucet fluid collection system 1006 comprises at least one collection tube. In some embodiments, the faucet fluid collection system comprises up to 20 collection tubes. The position of collection tubes 1010 is controlled by the rotation of the rotating handle 1052. Collection tubes 1010 are positioned directly beneath the second fluid hole 1098b when collecting a fluid.

In use, the tactile sensing device 1000 is turned on by the user via the insertion of the sensor array 1008 into the sensor array holder 1114. The user holds the tactile sensing device by the handle 1004 and presses the sensor array 1008 against the patient. The user visualizes underlying bone and/or soft tissue on the display screen 1032. The user inserts a needle into the needle guide 1002 and connects the needle to the 3-way valve 1014 via a needle hub connector 1100. Based on the image on the display screen 1032, the user is able to guide the needle at a 15° cephalad angle into a desired target location in the patient. In some embodiments, the user utilizes the tactile sensing device 1000 to perform a lumbar puncture to collect cerebrospinal fluid (CSF). Collection of CSF is facilitated by the faucet fluid collection system 1006. Further non-limiting examples of fluid collections systems are illustrated in FIGS. 5-8. Once the needle reaches the subarachnoid space, CSF begins to flow from the subarachnoid space, into the needle, through the needle hub, into the needle hub connector 1100, through the 3-way valve 1014, through the fluid port 1096, through the first fluid hole 1098a, through the second fluid hole 1098b, and finally into a first collection tube 1010a. The user optionally monitors the CSF pressure in real time once the needle is in the subarachnoid space by connecting a pressure sensor (not shown in FIGS. 1A, 1B, and 1C) to the 3-way valve 1014 via a pressure gauge connector 1094.

FIGS. 2A, 2B, and 2C illustrate another embodiment of the tactile sensing device 2000. The tactile sensing device 2000 comprises a sensor array 2008, a display screen 2032, a needle guide cartridge 2012, and a rail fluid collection system 2062. The tactile sensing device further comprises a gripper 2020 with a curved shape. The gripper 2020 is proximal to the user. The tactile sensing device 2000 is configured to image a target tissue location and to guide a needle to a desired target tissue location. The tactile sensing device 2000 further enables positioning of a needle at five discrete levels. The tactile sensing device 2000 further enables positioning of a needle at a 15° cephalad angle; this angle is not accurately shown in FIGS. 2A, 2B, and 2C.

Sensor array 2008 is distal to the user. Sensor array 2008 comprises 18 sensors: a first sensor 2016a, a second sensor 2016b, a third sensor 2016c, a fourth sensor 2016d, a fifth sensor 2016e, a sixth sensor 2016f, a seventh sensor 2016g, an eighth sensor 2016h, a ninth sensor 2016i, a tenth sensor 2016j, an eleventh sensor 2016k, a twelfth sensor 2016l, a thirteenth sensor 2016m, a fourteenth sensor 2016n, an fifteenth sensor 2016o, a sixteenth sensor 2016p, a seventeenth sensor 2016q, and an eighteenth sensor 2016r are shown in FIG. 2B. In some embodiments, the sensor array 2008 is a tactile sensor array. Sensor array 2008 is a sensor array cartridge that is loaded into a sensor array holder 2104, which is located distally, beneath the display screen 2032. Sensors in the sensor array 2008 face away from the user when the sensor array 2008 is loaded into place. In some embodiments, the sensor array 2008 turns on once it is loaded into the sensor array holder 2104. The sensor array 2008 is loaded in a multitude of ways, including all the non-limiting examples of loading sensor array 1008 mentioned supra. The sensors in the sensor array 2008 generate output voltage signals when the user applies a force using the tactile sensing device 2000 onto a surface, for example, onto a tissue of a patient. The sensor array 2008 is operatively connected to the display screen 2032 and a computing device (not shown in FIGS. 2A, 2B, and 2C). The sensor array 2008 relays its output voltage signals to the computing device (not shown in FIGS. 2A, 2B, and 2C), the computing device processes the output voltage signals, and an image of the output voltage signals is visualized on the display screen 2032.

The needle guide cartridge 2012 is a modular component. In some embodiments, the needle guide cartridge 2012 is disposable. In some embodiments, the needle guide cartridge 2012 is loaded into place. The needle guide cartridge 2012 comprises a first needle guide 2002a, a second needle guide 2002b, a third needle guide 2002c, a fourth needle guide 2002d, and a fifth needle guide 2002e. The needle guides are shaped like tracks and are configured to accept a needle (needle is not shown in FIGS. 2A, 2B, and 2C). A needle is placed on the needle guide by introducing it from the top, using either a proximal slit 2190a, a distal slit 2190b, a knob opening 2110, or a combination thereof. In some embodiments, a needle is placed on the needle guide by introducing it through a first side opening 2106a, a second side opening 2106b, a third side opening 2106c, a fourth side opening 2106d, or a fifth side opening 2106e. The needle guides are oriented at a 15° cephalad angle. Once inserted into a needle guide, the needle (not shown in FIGS. 2A, 2B, and 2C) exits the needle guide through a needle orifice located in the sensor array 2008. A needle inserted into the first needle guide 2002a exits the sensor array 2008 through the first needle orifice 2038a located in the sensor array 2008. A needle inserted into the second needle guide 2002b exits the sensor array 2008 through the second needle orifice 2038b located in the sensor array 2008. A needle inserted into the third needle guide 2002c exits the sensor array 2008 through the third needle orifice 2038c located in the sensor array 2008. A needle inserted into the fourth needle guide 2002d exits the sensor array 2008 through the fourth needle orifice 2038d located in the sensor array 2008. A needle inserted into the fifth needle guide 2002e exits the sensor array 2008 through the fifth needle orifice 2038e located in the sensor array 2008.

A 3-way valve 2014 is fixed to the needle guide cartridge 2012, below the fifth side opening 2106e, and in between the guide rails 2134. The 3-way valve comprises a needle hub connector 2100, a pressure gauge port 2108, and a fluid connector 2068. The needle hub connector 2100 faces distally away from the user, and it is configured to connect to tubing that further connects to a needle hub (tubing and needle not shown in FIGS. 2A, 2B, and 2C). The pressure gauge port 2108 is oriented away from the needle guide cartridge 2012. The pressure gauge port 2108 is configured to connect to a pressure sensor (not shown in FIGS. 2A, 2B, and 2C). The fluid connector 2068 is configured to connect to tubing. The fluid connector 2068 comprises an opening that is oriented downward in order to lead a fluid into a collection tube. For example, FIG. 2B shows the fluid connector 2068 protruding into a third collection tube 2010c.

The rail fluid collection system 2062 comprises a sliding rail platform 2064 and collection tubes. For example, the rail fluid collection system 2062 includes a first collection tube 2010a, a second collection tube 2010b, a third collection tube 2010c, and a fourth collection tube 2010d. Two guide rails 2134 extend beneath the needle guide cartridge 2012 and receive two longitudinal edges of the sliding rail platform 2064. The sliding rail platform 2064 includes rail platform openings 2132. In some embodiments, the rail platform openings 2132 are circular in shape. The rail platform openings 2132 are configured to hold collection tubes. The position of collection tubes 1010 is controlled by the sliding of rail platform 2064 along the guide rails 2134. Collection tubes 1010 are positioned directly beneath the fluid connector 2068 when collecting a fluid.

FIGS. 3A and 3B illustrate a sensor array 3008. In particular, FIG. 3B illustrates the application of the sensor array 3008 onto artificial lumbar vertebrae 3030. The sensor array 3008 comprises a sensor array platform 3022 that is rectangular in shape. The sensor array platform 3022 comprises a 6×3 array of cylindrical struts 3026 that protrude from the surface of the sensor array platform. In some embodiments, the cylindrical struts 3026 are 5 mm in diameter. In some embodiments, the center-to-center distance between the cylindrical struts 3026 is 11 mm. Each sensor 3016 is adhered onto the top surface of the cylindrical struts 3026. A hemispherical disk 3024 is secured above each adhered sensor 3016. The hemispherical disk 3024 enhances force feedback to each sensor 3016. In some embodiments, the hemispherical disk 3024 is composed of a compressible material. In some embodiments, the hemispherical disk 3024 is composed of a plastic that is soft and pliable at room temperature. In some embodiments, the hemispherical disk 3024 is composed of rubber. In some embodiments, the hemispherical disk 3024 is composed of silicone. In some embodiments, the hemispherical disk 3024 is composed of polyethylene. In some embodiments, the hemispherical disk 3024 is composed of a plastic that is hard and non-pliable at room temperature. In some embodiments, the hemispherical disk 3024 is composed of polystyrene. Non-limiting examples of materials that are used to fabricate the hemispherical disk 3024 include: polypropylene, polyester, polycarbonate, polyvinyl chloride, nylon, poly(methyl methacrylate), polyethylene terephthalate, polyimide, or Bakelite.

FIG. 4 shows a method of using a tactile sensing device to obtain an image. In a step 4078, the tactile sensing device is pressed against an area that is to be imaged and force is applied to the sensor array of the tactile sensing device. In a step 4080, a computing device is provided, and the computing device is operatively connected to the tactile sensing device. The computing device collects voltage signals that are generated by the sensor array of the tactile sensing device after a force is applied onto the surface of the sensors in the sensor array. In a step 4082, the computing device processes the collected voltage signals such that the voltage signals are converted into an image. In a step 4084, the image is displayed on a display screen of the tactile sensing device. In some embodiments, the image displayed is a heat map. In some embodiments, the image displayed provides the user feedback regarding the uniformity of their application of force to the tactile sensing device. In some embodiments, the image displayed includes the approximate position of a needle at the skin surface as well as the approximate depth of a needle. In some embodiments, for example, when the tactile sensing device comprises multiple needle guides as the exemplary embodiment shown in FIGS. 2A, 2B, and 2C, the image displayed includes the approximate positions and depths at all levels corresponding with the multiple needle guides.

FIG. 5 illustrates a flow control diaphragm fluid collection system 5042. The diaphragm fluid collection system 5042 is amenable to be incorporated into the tactile sensing device. The diaphragm fluid collection system 5042 includes a first collection tube 5010a, a second collection tube 5010b, a third collection tube 5010c, and a fourth collection tube 5010d. The collection tubes are stacked vertically, one on top of the other. The first collection tube 5010a is located on top of the second collection tube 5010b, which is located on top of the third collection tube 5010c, which is located on top of the fourth collection tube 5010d. A cap 5046 is configured to be secured on the first collection tube 5010a. Non-limiting examples of configurations to secure the cap 5046 onto the first collection tube 5010a include: threading, snap-fitting into the collection tube's circumference, snap-fitting into a slot, and snug-fitting. The first collection tube 5010a is connected to the second collection tube. The first collection tube 5010a has a first diaphragm 5044a instead of a bottom flat surface. A first rotating band 5112a allows the first diaphragm 5044a to be opened by rotating the first rotating band 5112a counterclockwise. In some embodiments, the first rotating band 5112a allows the first diaphragm 5044a to be opened by rotating the first rotating band 5112a clockwise. A first rotating band 5112a allows the first diaphragm 5044a to be closed by rotating the first rotating band 5112a clockwise. In some embodiments, the first rotating band 5112a allows the first diaphragm 5044a to be closed by rotating the first rotating band 5112a counter-clockwise. When the first diaphragm 5044a is opened, fluid is able to flow through the first aperture 5114a. The second collection tube 5010b includes a second diaphragm 5044b and a second rotating band 5112*b* that controls the opening and closing of the second diaphragm 5044*b* in the same manner as the first collection tube 5010*a* set up. Similarly, the third collection tube 5010*c* includes a third diaphragm 5044*c* and a third rotating band 5112*c* that controls the opening and closing of the third diaphragm 5044*c* in the same manner as already described. The fourth collection tube 5010*d* does not comprise a diaphragm. When the first diaphragm 5044*a*, the second diaphragm 5044*b*, and the third diaphragm 5044*c* are open, fluid flows through the first aperture 5114*a*, the second aperture 5114*b*, and the third aperture 5114*c* and collects inside the fourth collection tube 5010*d*. In this manner, the user is able to control which collection tube the fluid is to be collected in.

In some embodiments, the diaphragm fluid collection system 5042 comprises at least two collection tubes. In some embodiments, the diaphragm fluid collection system 5042 comprises three collection tubes. In some embodiments, the diaphragm fluid collection system 5042 comprises four collection tubes. In some embodiments, the diaphragm fluid collection system 5042 comprises five collection tubes. In some embodiments, the diaphragm fluid collection system 5042 comprises six collection tubes. In some embodiments, the diaphragm fluid collection system 5042 comprises seven collection tubes. In some embodiments, the diaphragm fluid collection system 5042 comprises eight collection tubes. In some embodiments, the diaphragm fluid collection system 5042 comprises nine collection tubes. In some embodiments, the diaphragm fluid collection system 5042 comprises ten collection tubes. In some embodiments, the diaphragm fluid collection system 5042 comprises between ten and fifteen collection tubes. In some embodiments, the diaphragm fluid collection system 5042 comprises between fifteen and twenty collection tubes.

FIG. 6 illustrates a top faucet fluid collection system 6120. In the top faucet fluid collection system 6120, a faucet element or rotating handle 6052 is operatively connected to housing 6118 that serves also as a cap to a container 6056. In some embodiments, a faucet element or rotating handle 6052 is placed at the bottom of a faucet base 6054 (this embodiment is now shown in FIG. 6), similar to the faucet fluid collection system 1006 of FIGS. 1A, 1B, and 1C. The rotating handle 6052 enables the collection tubes to be rotated clockwise or counterclockwise about an imaginary Y-axis that vertically traverses the center of the container 6056. The rotating handle 6052 is reversibly connected to a central rod 6116. The central rod 6116 is permanently connected to the faucet base 6054. Thus, when the central rod 6116 is attached to the rotating handle 6052 and the rotating handle 6052 is rotated, the rotational movement of the rotating handle 6052 enables the simultaneous rotation of the central rod 6116 and the faucet base 6054.

The container 6056 holds a plurality of collection tubes. In FIG. 6, there are a total of four collection tubes, but only a first collection tube 6010*a* and a second collection tube 6010*b* are clearly depicted. The housing 6118 is reversibly connected to the container 6056. Non-limiting examples of configurations to reversibly secure the housing 6118 onto the container 6056 include: threading, snap-fitting into the collection tube's circumference, snap-fitting into a slot, or snug-fitting. In some embodiments, the collection tubes are reversibly secured to the bottom of the container 6056. In some embodiments, the collection tubes are reversibly secured to the faucet base 6054. The user detaches the container 6056 from the housing 6118 and disconnects the central rod 6116 from the rotating handle 6052, in order to access the collection tubes inside the container 6056.

A circular plate is found within the housing 6118 (not shown in FIG. 6), lying parallel to the rotating handle 6052. The circular plate (not shown in FIG. 6) has a single orifice located directly beneath the faucet connector 6050. The faucet connector 6050 extends outwardly from the housing 6118 and is perpendicular to the container 6056. The faucet connector 6050 is configured to connect to a needle hub or tubing. Fluid traveling from a needle hub or from tubing and through the faucet connector 6050 flows through an elbow hollow opening (not shown in FIG. 6) that aligns with the orifice in the circular plate, the fluid exits the orifice in the circular plate (not shown in FIG. 6), and flows into one of the collection tubes inside the container. The collection tubes are rotated clockwise or counterclockwise to allow for sequential filling. In some embodiments, the housing 6118 has numbers or labels to indicate the position of a collection tube. In some embodiments, the rotating handle 6052 has numbers or labels to indicate the position of a collection tube.

FIG. 7 illustrates a spoke fluid collection system 7058. The spoke fluid collection system 7058 comprises a central hub 7060, which is octagonal in shape. The central hub 7060 includes a first central hub opening 7086*a*, a second central hub opening 7086*b*, a third central hub opening 7086*c*, and a fourth central hub opening 7086*d*. Each central hub opening is located on a side surface of the central hub 7060. For example, FIG. 7 illustrates the third central hub opening 7086*c* is located on the third side surface 7102*c* and the fourth central hub opening 7086*d* is located on the fourth side surface 7102*d*. The first central hub opening 7086*a* and the second central hub opening 7086*b* are also located on side surfaces, however, these side surfaces are not shown in FIG. 7. The first central hub opening 7086*a* is configured to connect to a first collection tube 7010*a*. The second central hub opening 7086*b* is configured to connect to a second collection tube 7010*b*. The third central hub opening 7086*c* is configured to connect to a third collection tube 7010*c*. The fourth central hub opening 7086*d* is configured to connect to a fourth collection tube 7010*d*. Non-limiting examples of configurations to connect the collection tubes to the central hub openings include: threading, snap-fitting into the collection tube's circumference, snap-fitting into a slot, or snug-fitting. The central hub 7060 has a front face 7092 that is planar. A spoke connector 7088 extends outwardly from the front face 7092 and is perpendicular to an imaginary Y-axis vertically traversing the central hub 7060 through the center of the first collection tube 7010*a* and through the center of the third collection tube 7010*c*. The spoke connector 7088 is configured to connect to a needle hub, tubing, or a 3-way valve. The spoke connector 7088 is hollow inside and serves as a channel to transport fluid. The interior (not shown in FIG. 7) of the central hub 7060 is completely sealed except for openings that coincide with the central hub openings. In addition, the central hub 7060 comprises a solid inner ring-like structure (not shown in FIG. 7) located in the interior of the central hub 7060. The solid inner ring-like structure (not shown in FIG. 7) has a single orifice that aligns with the first collection tube 7010*a*. Fluid flowing through the spoke connector 7088 exits the spoke connector 7088 and falls at a 90° angle into the orifice of the solid inner ring-like structure. Thus, any fluid flowing through the spoke connector 7088 only accumulates in a collection tube that is in the position of the first collection tube 7010*a* shown in FIG. 7.

Secured to the back face (not shown in FIG. 7) of the central hub 7060 is a knob (not shown in FIG. 7) that allows for the rotation of the central hub 7060 about an imaginary Z-axis that traverses the central hub 7060 through its center, perpendicular to the first collection tube 7010a and the third collection tube 7010c. The knob (not shown in FIG. 7) is rotated clockwise or counterclockwise. The rotation of the central hub 7060 by the knob (not shown in FIG. 7) enables the collection tubes to be rotated about the imaginary Z-axis when attached to the central hub 7060. In some embodiments, the knob (not shown in FIG. 7) has numbers or labels to indicate the position of a collection tube.

FIG. 8 illustrates a rail fluid collection system 8062. The rail fluid collection system 8062 comprises a sliding rail platform 8064, a first collection tube 8010a, a second collection tube 8010b, a third collection tube 8010c, a fourth collection tube 8010d, and guide rails 8134. The guide rails 8134 receive two longitudinal edges of the sliding rail platform 8064. The sliding rail platform 8064 includes rail platform openings 8132. In some embodiments, the rail platform openings 8132 are circular in shape. The rail platform openings 8132 are configured to hold collection tubes. The lip 8122 of the collection tube projects onto the rail platform 8064. The position of the collection tubes is controlled by a manual sliding motion 8138 of the rail platform 8064 along the guide rails 8134. The collection tubes are positioned directly beneath a 3-way valve 8014 when they are to collect fluid.

The function of the 3-way valve 8014 is to direct fluid from an external needle hub or tubing into a collection tube. The 3-way valve 8014 includes a fluid connector 8068, which protrudes from the bottom surface of the 3-way valve 8014. The 3-way valve also includes a needle hub connector 8100, which protrudes outwardly from the 3-way valve 8014 and is perpendicular to the fluid connector 8100. The needle hub connector 8100 is configured to connect to an external needle hub or tubing. A fluid flowing from an external needle hub or tubing, through the needle hub connector 8100, flows downward at a 90° angle through the fluid connector 8068 when exiting the needle hub connector 8100, and subsequently flows into a first collection tube 8010a. The fluid connector 8068 is configured to connect to tubing. In some embodiments, the fluid connector 8068 is optionally connected to tubing instead of only openly protruding into a collection tube. Another function of the 3-way valve 8014 is to enable a pressure sensor to obtain a pressure measurement of the fluid that is in contact with the 3-way valve 8014. The 3-way valve 8014 includes a pressure gauge port 8108 facing away from the guide rails 8134. The pressure gauge port 8108 is configured to connect to a pressure sensor.

Figure 9A:
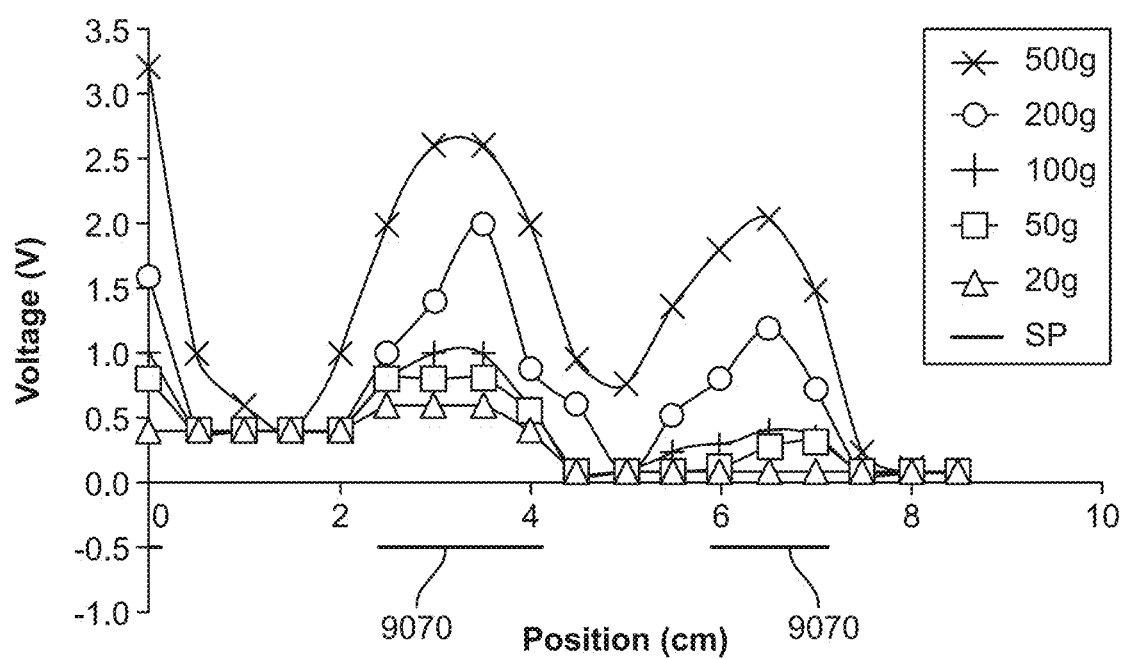
FIGS. 9A-B illustrate voltage signals acquired by a tactile sensing device utilizing an artificial lumbar vertebrae model.
Figure 9B:
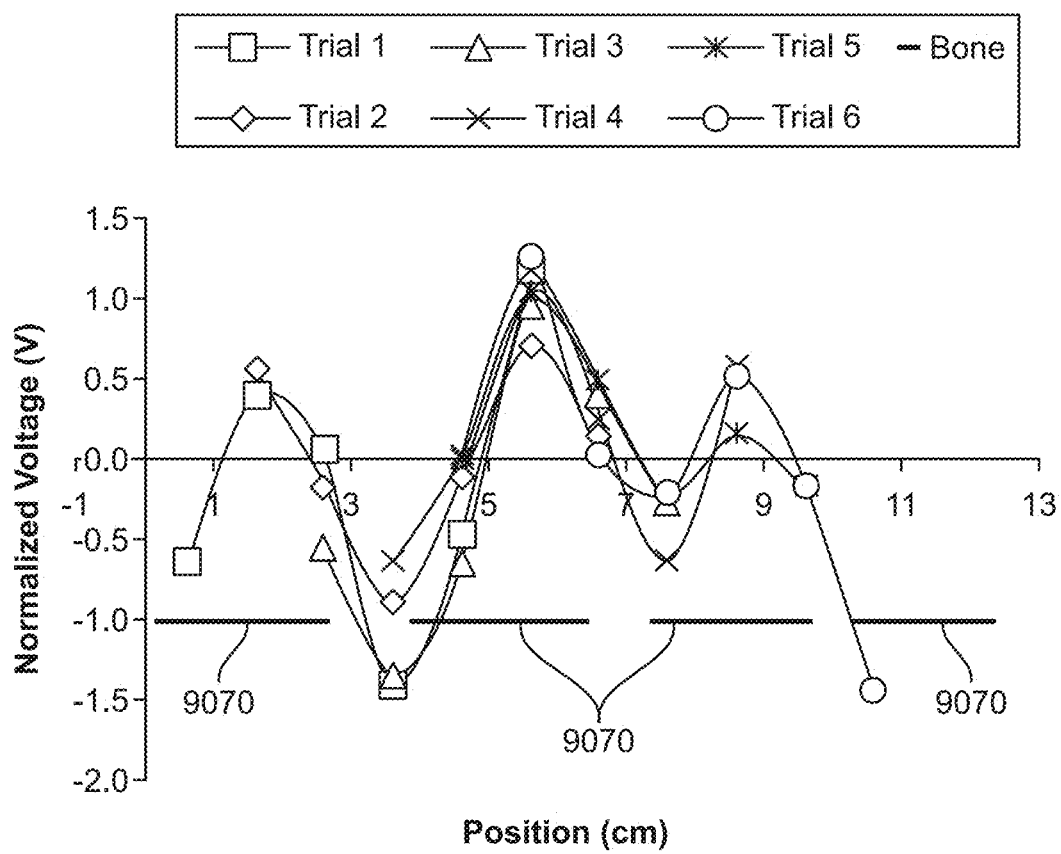

FIGS. 9A and 9B are exemplary data demonstrating the functionality of the tactile sensing device on a lumbar spine model. Recordings are acquired using a combination of signal acquisition and processing executed by a computing device. In some embodiments, the computing device further comprises a non-transitory computer readable storage medium with a computer program including instructions executable by a processor. In some embodiments, the computer program is written in Python code, Arduino code, or a combination thereof. FIG. 9A demonstrates the change in voltage across a single sensor when moved in 1 cm increments, with changes in applied force. The applied force varies based on a mass. FIG. 9A shows the mass, and thus the applied force, varies between 20 g to 500 g. The bolded horizontal lines represent the underlying spinous processes 9070. Voltage increases are apparent for sensors that are situated above these underlying spinous processes 9070. FIG. 9B demonstrates the change in voltage across a tactile sensing device comprising a column of 6 sensors with a 1 cm center-to-center distance. Voltages across each sensor are shown in FIG. 9B for 6 trials. In each trial, the column of 6 sensors is moved 1 cm increments. An increase in voltage is apparent for sensors above the underlying spinous processes 9070 (denoted as "bone" in FIG. 9B) throughout the 6 trials.

FIG. 10 is a flow chart describing the instructions included in a computer program, which are executable by a computing device. In some embodiments, a sensor array comprising at least one sensor is configured to output a signal in response to a change in force applied to its surface; wherein the signal is converted to a pressure map. Step 1 10124 describes the output voltage signals generated by the force-sensitive resistors via a voltage divider are inputted into the computing device via a multiplexer. Step 2 10126 describes the inputted voltage signals are written to a serial monitor. In some embodiments, step 2 10126 further comprises organizing the inputted voltage signals. In some embodiments, a first computer program that includes instructions executable by a processor performs step 2 10126. In some embodiments, the instructions to perform step 2 10126, which are included in the computer program are written in Arduino programming language. In step 3 10128, a second computer program includes instructions to acquire the inputted voltage signals that were written to the serial monitor and generates a 6×3 array of sensor data. In some embodiments, the instructions to perform step 3 10128, which are included in the second computer program are executable by a processor. In step 4 10130, a second computer program includes instructions to process the inputted voltage signals that were written to the serial monitor and rescales the previously generated 6×3 array of sensor data to a 60×30 array of sensor data. In some embodiments, the instructions to perform step 4 10130 use cubic interpolation methods to rescale the array of sensor data. In some embodiments, the instructions to perform step 4 10130, which are included in the second computer program are executable by a processor. In step 5 10132, a second computer program includes instructions to update the display for real-time target tissue visualization. In some embodiments, the instructions to perform step 3 10128, step 4 10130, and step 5 10132, which are included in the second computer program are written in Python programming language. In some embodiments, the display is updated for real-time visualization of a patient's spine. Thus, FIG. 10 illustrates the process of transforming sensor output into a visual display. In some embodiments, the visual display is a pressure map.

In some embodiments, the algorithm shown in FIG. 10 is used to generate a pressure map. In some embodiments, the pressure map is a heat map. In some embodiments, the heat map displays high voltages in a red color. In some embodiments, high voltages are at or near 5V, corresponding to greater applied force. In some embodiments, high voltages in a heat map correspond to a bone. In some embodiments, high voltages in a heat map correspond to spinous processes. In some embodiments, the heat map displays low voltages in a blue color. In some embodiments, low voltages in a heat map correspond to tissue softer than bone. In some embodiments, low voltages in a heat map correspond to inter interspinous ligaments.

Figure 11A:
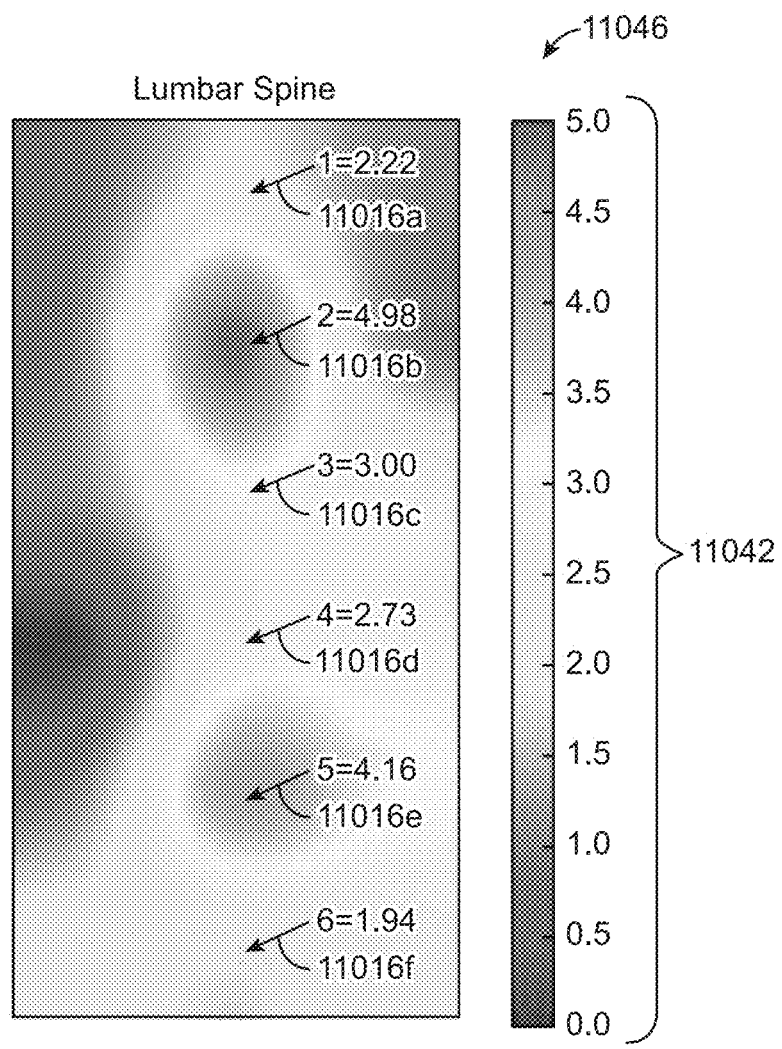
FIGS. 11A-B are exemplary pressure maps generated by the tactile sensing device.

FIG. 11A illustrates a representative image of a pressure-mapping output. In some embodiments, the pressure map 11046 visually represents a target tissue location in an individual. In some embodiments, a pressure map 11046 is generated using the algorithm shown in FIG. 10. In some embodiments, the pressure map 11046 shown in FIG. 11A is generated by using the tactile sensing device on an obese model of the lumbar spine. In some embodiments, a representation of the setup for using the tactile-sensing array applied to an obese model of the lumbar spine is shown in FIG. 3B. In some embodiments, the tactile sensing device, comprising the sensor array, is pressed lightly against the lumbar spine model; the 2nd and 5th midline sensors are positioned directly over the spinous processes. In some embodiments, a third computer program, which includes instructions to display the voltage signals sensed at a 1st midline sensor 11016*a*, a 2nd midline sensor 11016*b*, a 3rd midline sensor 11016*c*, a 4th midline sensor 11016*d*, a 5th midline sensor 11016*e*, and a 6th midline sensor 11016*f* along the midline (column 2 of the sensor array) after interpolation, was added to the algorithm described in FIG. 10. In some embodiments, the pressure map 11046 is generated using the algorithm as described in FIG. 10 and the third computer program described supra. In some embodiments, the voltage values 11042, which are shown in FIG. 11A, range between about 0V and about 5V. In some embodiments, high voltage values are shown in a color red. In some embodiments, low voltage values are shown in a color blue. As shown in FIG. 11A, the greatest force, as evidenced by higher voltages, is found over the 2nd midline sensor 11016*b* and 5th midline sensor 11016*e*, which correspond to bony landmarks. In addition to revealing the gap between spinous processes, this visualization is also useful in providing feedback to the user on the uniformity of their force application. For example, it is clear in this pressure map 11046 that the user's force is slightly biased toward the sensors on the right. Therefore, the pressure map 11046 indicates to the user that the force that they are applying onto the tactile sensing device needs to be better distributed or corrected.

Figure 11B:
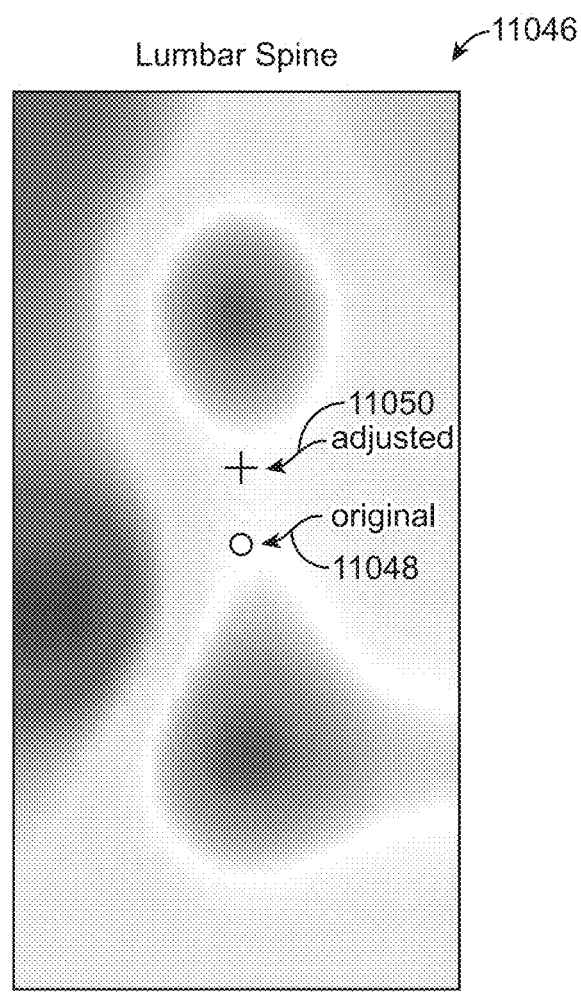

FIG. 11B illustrates a pressure map 11046 showing the needle's position at the skin level ("original"), and its adjusted, projected location, accounting for the remaining depth of the subcutaneous fat. In some embodiments, the pressure map 11046 only displays the needle position at the skin level 11048. In some embodiments, the pressure map 11046 only displays the projected position of the needle 11050, adjusted for the remaining depth of the subcutaneous fat. In some embodiments, the pressure map 11046 shown in FIG. 11B is generated by using the tactile sensing device on a lumbar spine model.

In some embodiments, a trigonometric algorithm, as shown in Equation 2 below, is used to determine the depth level at which the needle will be once it traverses the subcutaneous fat.

$$h = \tan(\theta) * d;$$ Equation 2:

wherein where h is the adjustment level; d refers to the tissue depth; and θ is the cephalad angle at which the needle is inserted.

In some embodiments, the depth used in this equation is experimentally determined to robustly apply to lumbar spine models with a wide spectrum of body mass indexes (BMIs): provided that the user applies significant force to overcome the damping in the underlying fat layers, the remaining depth to the spinous process becomes fairly uniform across cases.

In some embodiments, the depth level at which the needle will be once it traverses the subcutaneous fat is calculated proportionally. In some embodiments, the depth level at which the needle will be once it traverses the subcutaneous fat is calculated based on calculating the ratio between the maximum voltage reading (for example, over a spinous process) and the minimum voltage reading (for example, over an interspinous ligament) for the midline sensors and comparing this ratio to an empirically determined ratio of the maximum voltage reading to the minimum voltage reading. In some embodiments, the empirically determined ratio of the maximum voltage reading to the minimum voltage reading is determined based on a known depth.

In some embodiments, the depth level at which the needle will be once it traverses the subcutaneous fat is calculated based on machine-learning algorithms. In some embodiments, machine-learning algorithms enhance the accuracy of the displayed needle projection.

In some embodiments, the tactile sensing device further comprises a marking tool. The marking tool helps the user identify the tissue target location. In some embodiments, the marking tool enables the user to mark the entry point of a needle on the skin surface of the patient. In some embodiments, the marking tool enables the user to mark or label a tissue target location. In some embodiments, marking or labeling the tissue target location is done subcutaneously, intramuscularly, or on the skin surface. In some embodiments, the marked tissue location is detected by a medical imaging device. In some embodiments, the marking tool enables the user to mark or label a target tissue location in order to be identified by a medical imaging device or system. In some embodiments, the marking tool is a light, an ink, a hydrogel, a nanoparticle. In some embodiments, the light is a laser light or a light emitting diode (LED). In some embodiments, the ink is a permanent ink, a gentian violent ink, a water-based ink, an oil-based in, a liquid ink, or a gel ink. In some embodiments, the hydrogel further comprises a contrast agent. In some embodiments, the nanoparticle further comprises a contrast agent. In some embodiments, the contrast agent includes, but is not limited to: a magnetic contrast agent, a radiocontrast agent, a radioactive contrast agent, a magnetic resonance imaging contrast agent, and a microbubble contrast agent. Non-limiting examples of the magnetic contrast agent include: gadolinium-based agents or nanoparticles, iron oxide-based agents or nanoparticles, iron platinum-based agents or nanoparticles, and manganese-based agents or nanoparticles. Non-limiting examples of the radiocontrast agent include: iodine-based agents or nanoparticles, air, thorium dioxide, carbon dioxide, gastrografin, and barium-based agents or nanoparticles. Non-limiting examples of the radioactive contrast agent include: $^{64}$Cu diacetyl-bis($N^4$-methylthiosemicarbazone), also called ATSM or Copper 64, $^{18}$F-fluorodeoxyglucose (FDG), $^{18}$F-fluoride, 3'-deoxy-3'-[$^{18}$F]fluorothymidine (FLT), $^{18}$F-fluoromisonidazole, gallium, techtenium-99m, and thallium.

EXAMPLES

Example 1

Tactile Sensing Device Prototype Testing in a Lumbar Spine Model

Select data is presented here to demonstrate the functionality of the tactile sensing device 1000 on an artificial lumbar spine model 3028, as shown in FIG. 3B. Recordings were acquired using a combination of signal acquisition and processing in a computing device. FIG. 9A illustrates the change in voltage across a single sensor when moved in 1 centimeter increments, with changes in applied force 9076. The bolded horizontal lines 9070 represent the underlying artificial spinous processes 3030; voltage increases 9072 are apparent for sensors that are situated above these artificial spinous processes. Detected voltage values are the lowest 9074 when there are no artificial spinous processes present below the tactile sensing device 1000. FIG. 9B exemplifies a column of 6 sensors with 1 centimeter center-to-center distance was designed. Voltages across each sensor were recorded for 6 trials, moving the column 1 centimeter each time. Again, an increase in voltage 9072 is apparent for sensors above the artificial spinous processes 3030 (denoted as 'bone' and illustrated by the bolded horizontal lines 9070 on FIG. 9B). Results presented by FIG. 9B demonstrate the detection of artificial bone using the tactile sensing device was accurate and consistent across all six trials.

Example 2

Diagnostic Lumbar Puncture Using a Tactile Sensing Device

A health care worker performing a lumbar puncture on an obese subject places the tactile sensing device on the lumbar region of the subject. A pressure map, viewed as a heat map by the health care worker, appears on the display screen 1032, 2032 of the tactile sensing device 1000, 2000. The heat map indicates bone structures, in this case spinous processes of the lumbar vertebrae, by representing these in red color base and indicates non-bone structures by representing these in a blue color base. The tactile sensing device simultaneously computes a needle projection and displays it on the pressure map. The health care worker adjusts the tactile sensing device's needle guide angle to a cephalad angle degree between −45° and 45°. After identifying a gap between two of the lumbar vertebrae, for example L2 and L3, the health care worker inserts a spinal needle into the tactile sensing device's needle guide. The health care worker uses the needle guide and the needle projection and heat map on the screen to guide the needle into the subarachnoid space. The health care worker then uses the tactile sensing device's 1000 modular fluid collection system 1006 to collect cerebrospinal fluid (CSF). Once all CSF samples are collected, the health care worker uses the tactile sensing device's 1000 electronic pressure sensor, which automatically displays the CSF pressure CSF flow is detected, to readout and record the subject's intracranial pressure.

Example 3

Epidural Administration of a Therapeutic Using a Tactile Sensing Device

A health care worker performing an epidural administration of an anesthetic on a pregnant patient to places the tactile sensing device on the lumbar region of the pregnant patient. A pressure map, viewed as a heat map by the health care worker, appears on the display screen 1032, 2032 of the tactile sensing device 1000, 2000. The heat map indicates bone structures, in this case spinous processes of the lumbar vertebrae, by representing these in red color base and indicates non-bone structures by representing these in a blue color base. The tactile sensing device simultaneously computes a needle projection and displays it on the pressure map. The health care worker adjusts the tactile sensing device's needle guide angle to a cephalad angle degree between −45° and 45°. After identifying a gap between two of the lumbar vertebrae, for example L2 and L3, the health care worker inserts a spinal needle into the tactile sensing device's needle guide. The health care worker uses the needle guide and the needle projection and heat map on the screen to guide the needle into the epidural space and inject the anesthetic.

Example 4

Synovial Cavity Injection Using a Tactile Sensing Device

A health care worker administering a hyaluronan injection, such as Synvisc-One®, to the knee joint of a patient suffering from osteoarthritis uses the tactile sensing device, instead of the traditional palpation and pen marking approach, to correctly localize needle placement. Correct needle placement is crucial in order to avoid accidentally jabbing the knee's cartilage and eliciting further damage. The health care worker places the tactile sensing device 1000, 2000 on the patient's knee. A pressure map, viewed as a heat map by the health care worker, appears on the display screen 1032, 2032 of the tactile sensing device 1000, 2000. The heat map indicates bone structures, in this case the patella, femur and tibia, by representing these in a red color base. The heat map indicates non-bone structures, in this case the bursae of the knee, by representing these in a blue color base. The tactile sensing device 1000, 2000 simultaneously computes a needle projection and displays it on the pressure map. The health care worker adjusts the tactile sensing device's 1000, 2000 needle guide angle to a cephalad angle degree between −45° and 45°. After identifying the suprapatellar bursa, the health care worker inserts a needle into the tactile sensing device's 1000, 2000 needle guide. The health care worker uses the needle guide and the needle projection and heat map on the screen to guide the needle into the suprapatellar bursa and inject hyaluronan.

What is claimed is:

1. A method for imaging a target tissue location and underlying bony landmarks therefrom in an individual in need thereof, comprising:
   a) placing a tactile sensing device on the individual, the tactile sensing device comprising:
      a sensor array comprising a first sensor comprising a first surface and a second sensor comprising a second surface;
      a frame comprising a needle guide having a proximal opening and a distal opening and a track therebetween;
      a display screen coupled to the frame and operatively coupled to the sensor array; and
      a computing device comprising a processor operatively coupled to the sensor array and operatively coupled to the display screen, and a non-transitory computer readable storage medium with a computer program including instructions executable by the processor;
   b) applying a first force to the first surface of the first sensor to generate a first voltage signal;
   c) applying a second force to the second surface of the second sensor to generate a second voltage signal;
   d) viewing a pressure map representing the underlying bony landmarks and the target tissue location in the individual on the display screen;
   e) viewing a projected subcutaneous location of a needle on the display screen; and
   f) guiding the needle towards the individual from the proximal opening of the needle guide to the distal opening of the needle guide, along the track,
   wherein the pressure map is generated by converting the first voltage signal and the second voltage signal received from the sensor array,
wherein the projected subcutaneous location of the needle to be inserted into the individual is calculated based upon a trigonometric algorithm comprising: $h=\tan(\theta)*d$; where h is solved for and is an adjustment level relative to an original location of the needle at a skin level at the distal opening; d refers to a tissue depth; and θ is a cephalad angle at which the needle is inserted and where d is calculated based upon calculating a ratio between a maximum voltage reading of the first voltage signal and the second voltage signal and a minimum voltage reading of the first voltage signal and the second voltage signal and comparing the ratio to an empirically determined ratio based on a known depth.

2. The method of claim 1, wherein the target tissue location is a vertebral column.

3. The method of claim 1, wherein the underlying bony landmarks are spinous processes.

4. The method of claim 1, further comprising:
g) localizing a first spinous process and a second spinous process of the individual on the pressure map;
h) identifying a gap between the first spinous process and the second spinous process; and
i) inserting the needle through the needle guide, between the first spinous process and the second spinous process of the individual.

5. The method of claim 1, wherein the needle is a spinal needle or an epidural needle.

6. The method of claim 1, further comprising advancing the needle into an epidural space of the individual, a subarachnoid space of the individual, or a combination thereof.

7. The method of claim 6, further comprising collecting a cerebrospinal fluid of the individual through the needle.

8. The method of claim 1, wherein a pressure sensor is operatively coupled to the tactile sensing device.

9. The method of claim 8, further comprising measuring a pressure of a fluid at the target tissue location with the pressure sensor.

10. The method of claim 9, wherein the pressure of the fluid is an intracranial pressure of the individual.

11. The method of claim 9, comprising displaying the pressure of the fluid on the display screen.

12. The method of claim 1, further comprising measuring an intracranial pressure of the individual with a manometer.

13. The method of claim 1, further comprising administrating a therapeutic agent to the individual.

14. The method of claim 13, wherein the therapeutic agent is administered into an epidural space of the individual, a subarachnoid space of the individual, or a combination thereof.

15. The method of claim 1, further comprising implanting a catheter in the individual by inserting the catheter through the needle and advancing the catheter into the individual.

16. The method of claim 15, wherein the catheter is implanted into an epidural space of the individual, a subarachnoid space of the individual, or a combination thereof.

17. The method of claim 15, wherein the catheter is used to monitor an intracranial pressure of the individual.

18. The method of claim 15, wherein the catheter is a therapeutic agent delivery port.

19. The method of claim 13, wherein the therapeutic agent is an analgesic, an anesthetic, a chemotherapeutic agent, a contrast agent, or a dye.

20. A method for imaging a target tissue location and underlying bony landmarks therefrom in an individual in need thereof, comprising:
a) in a tactile sensing device comprising:
a sensor array comprising a first sensor comprising a first surface and a second sensor comprising a second surface;
a frame comprising a needle guide having a proximal opening and a distal opening and a track therebetween configured to guide the needle towards the individual from the proximal opening of the needle guide to the distal opening of the needle guide, along the track;
a display screen coupled to the frame and operatively coupled to the sensor array; and
a computing device comprising a processor operatively coupled to the sensor array and operatively coupled to the display screen, and a non-transitory computer readable storage medium with a computer program including instructions executable by the processor,
generating a first voltage signal in response to a first change in a first force applied to the first surface of the first sensor;
b) generating a second voltage signal in response to a second change in a second force applied to the second surface of the second sensor;
c) converting the first voltage signal and the second voltage signal received from the sensor array into a pressure map representing the underlying bony landmarks and the target tissue location in the individual;
d) displaying the pressure map on the display screen e) calculating a projected subcutaneous location of a needle to be inserted into the individual; and
f) displaying the projected subcutaneous location of the needle on the display screen wherein step e) is based upon a trigonometric algorithm comprising: $h = \tan(\theta) * d$; where h is solved for and is an adjustment level relative to an original location of the needle at a skin level at the distal opening; d refers to a tissue depth; and θ is a cephalad angle at which the needle is inserted and where d is calculated based upon calculating a ratio between a maximum voltage reading of the first voltage signal and the second voltage signal and a minimum voltage reading of the first voltage signal and the second voltage signal and comparing the ratio to an empirically determined ratio based on a known depth.

* * * * *